United States Patent [19]

Burgett et al.

[11] Patent Number: 5,945,320
[45] Date of Patent: Aug. 31, 1999

[54] PLATENOLIDE SYNTHASE GENE

[75] Inventors: Stanley G. Burgett; Stuart A. Kuhstoss; Ramachandra N. Rao, all of Indianapolis; Mark A. Richardson, Bloomington; Paul R. Rosteck, Jr., Indianapolis, all of Ind.

[73] Assignee: Eli Lilly and Company, Indianapolis, Ind.

[21] Appl. No.: 08/804,198

[22] Filed: Feb. 21, 1997

Related U.S. Application Data

[60] Provisional application No. 60/012,050, Feb. 22, 1996.
[51] Int. Cl.[6] .............................. C12N 9/00; C12N 15/52; C12N 15/63; C12N 15/76
[52] U.S. Cl. ...................... 435/183; 435/69.1; 435/252.3; 435/252.35; 435/320.1; 530/350; 536/23.2
[58] Field of Search ............................. 435/69.1, 252.3, 435/252.35, 320.1, 183; 530/350; 536/23.2

[56] References Cited

U.S. PATENT DOCUMENTS

| 5,098,837 | 3/1992 | Beckmann et al. ........................... 435/6 |
| 5,252,474 | 10/1993 | Gewain et al. ....................... 435/172.3 |
| 5,614,619 | 3/1997 | Piepersberg et al. ................... 536/23.2 |
| 5,639,949 | 6/1997 | Ligon et al. ............................ 800/20.5 |
| 5,643,774 | 7/1997 | Ligon et al. ............................. 435/183 |
| 5,662,898 | 9/1997 | Ligon et al. ............................ 424/93.2 |

FOREIGN PATENT DOCUMENTS

| 0463707 | 1/1992 | European Pat. Off. . |
| WO 87/03907 | 7/1987 | WIPO . |
| WO 93/13663 | 7/1993 | WIPO . |
| WO93/13663 | 7/1993 | WIPO . |

OTHER PUBLICATIONS

David A. Hopwood and David H. Sherman, "Molecular Genetics of Polyketides and its Comparison to Fatty Acid Biosynthesis," *Annu. Rev. Genet.*, 24:37–66 (1990).

Stefano Donadio and Leonard Katz, "Organization of the enzymatic domains in the multifunctional polyketide synthase involved in erythromycin formation in *Saccharopolyspora erythraea*," *Gene*, 111:51–60 (1992).

Jesus Cortes, et al., "Repositioning of a Domain in Modular Polyketide Synthase to Promote Specific Chain Cleavage," *Science*, 268:1487–1489 (1995).

Stefano Donadio, et al., "Modular Organization of Genes Required for Complex Polyketide Biosynthesis," *Science*, 252:675–679 (1991).

M. A. Richardson, et al., "Cloning of Spiramycin Biosynthetic Genes and Their Use in Constructing *Streptomyces ambofaciens* Mutants Defective in Spiramycin Biosynthesis," *Journal of Bacteriology*, vol. 172, No. 7, 3790–3798 (1990).

Robert J. Beckmann, Karen Cox, and Eugene T. Seno, "A Cluster of Tylosin Biosynthetic Genes Is Interrupted by a Structurally Unstable Segment Containing Four Repeated Sequences," *Genetics and Molecular Biology of Industrial Microorganisms*, 176–186 (1989).

Leonard Katz and Stefano Donadio, "Polyketide Synthesis: Prospects for Hybrid Antibiotics," *Annu. Rev. Microbiol.*, 47:875–912 (1993).

Stefano Donadio, et al., "Biosynthesis of the erythromycin macrolactone and a rational approach for producing hybrid macrolides," *Gene*, 115:97–103 (1992).

Dougals J. MacNeil, et al., "Complex organization of the *Streptomyces avermitilis* genes encoding the avermectin polyketide synthase," *Gene*, 115:119–125 (1992).

(List continued on next page.)

*Primary Examiner*—Robert A. Wax
*Assistant Examiner*—William W. Moore
*Attorney, Agent, or Firm*—Paul R. Cantrell; Guy Kevin Townsend

[57] ABSTRACT

A DNA molecule isolated from *Streptomyces ambofaciens* encodes the multi-functional proteins which direct the synthesis of the polyketide platenolide.

25 Claims, 3 Drawing Sheets

OTHER PUBLICATIONS

Douglas J. MacNeil, et al., "Correlation of the Avermectin Polyketide Synthase Genes to the Avermectin Structure," *Annals New York Academy of Sciences*, 721:123–132 (1994).

C. Richard Hutchinson, "Drug Synthesis by Genetically Engineered Microorganisms," *Bio/Technology*, 12:375–380 (1994).

Omura, S., et al., *Journal of Biochemistry* (Tokyo), vol. 86, Isolation and properties of spiramycin 1 3–hydroxyl acylase from *Streptomyces ambofaciens*:, pp. 1753–1758, (1979).

Richardson, M.A. et al., *Journal of Facteriology*, vol. 172, "cloning of spiramycin biosynthetic genes and their use in constructing *Streptomyces ambofaciens* mutants defective in spiramycin biosynthesis", pp. 3790–3798, (1990).

Geistlch, M., et al., *Molecular Microbiology*, vol. 6, "Characterization of a novel regulatory gene governing the expression of polyketide synthase gene in *Streptomyces ambofaciens*", pp. 2019–2029, (1992).

Kirst, H.A., *Progress in Medicinal Chemistry*, vol. 31, "Semisynthetic derivatives of 16–membered macrolide antibiotics".

Katz, L., et al., in *Genetics and Biochemistry of Antibiotic Production*, Vining, L.C., et al., Eds., Butterworth–Heinemann, Pub., "Macrolides", pp. 385–420, (1995).

Li, T., et al., *Chinese Journal of Biotechnology*, vol. 7, "Cloning and expression of spiramycin polyketide synthase genes from S. spiramyceticus U–941", pp. 33–42, (1996).

Kuhstoss, S., et al., *Gene*, vol. 183, "Production of a novel polyketide through the construction of hybrid polyketide synthase", pp. 231–236, (1996).

Aigle, B., et al.,*Microbiology*, vol. 142, "An amplifiable and deletable locus of *Streptomyces ambofaciens* RP181110 contains a very large gene homologous to polyketide synthase genes", pp. 2815–2824. (1996).

Maezawa, I., et al., "Biological Gycosidation of Macrolide Aglycones. II Isolation and Characterization of Desosaminyl–Platenolide I," *The Journal of Antibiotics*, 31:309–318 (1978).

Furumai, T., et al., "Studies on the Biosynthesis of Basic 15–Membered Macrolide Antibiotics, Platenomycins, III Production, Isolation and Structures of Platenolides I and II," *The Journal of Antibiotics*, 28:783–788 (1975).

Furumai, T., et al., "Studies on the Biosynthesis of Basic 16–Membered Macrolide Antibiotics, Platenomycins, II Production, Isolation and Structures of 3–O–Propionyl–5–Omycaminosyl Platenolides I and II, 9–Dehydro Demycarosyl Platenomycin and Demycarosyl Platenomycin," *The Journal of Antibiotics*, 28:775–782 (1975).

Furumai T., et al., "Studies on the Biosynthesis of Basic 1–Membered Macrolide Antibiotic, Platenomycins. I* Selection of and Cosynthesis by Non–platenomycin–Producing Mutants," *The Journal of Antibiotics*, 28:770–774 (1975).

Grafe, U., et al., Isolation and Structures of Nitrogen–Free Platenolide Glycosides 11. The 5–O–(α–Mycarosyl)–and 5–O(3'–Demethyl–β–Mycarosyl)–Platenolides I and II, *The Journal of Antibiotics*, 33:574–578 (1980).

Grafe, U. et al., Isolation and Structures of Nitrogen–Free Platenolide Glycosides I. The 5–O–(Deoxy–3'–C–acetyl–β–D–Hexopyranosyl)–Platenolides I and II, *The Journal of Antibiotics*, 33:566–573 (1980).

Grafe, U., et al., "The Platenolides I and II as Precursors of Turimycin", *The Journal of Antibiotics*, 33:663–664 (1980).

Rakhit, S., et al., "Structure Activity Relationship in Sixteen Membered Macrolide Antibiotics," *The Journal of Antibiotics*, 27:221–224 (1974).

Omura, S., et al., "Biosynthetic Origin of Carbons 3 and 4 of Leucomycin Aglycone", *The Journal of Antibiotics*, 36:611–613 (1983).

Omura, S., et al., Journal of Biochemistry (Tokyo), vol. 86, "Isolation and properties of spiramycin 1 3–hydroxl acylase from *Streptomyces ambofaciens*", pp. 1753–1758, 1979.

Richardson, M. A., et al., Journal of Bacteriology, vol. 172, "Cloning of spiramycin biosynthetic genes and their use in constructing *Streptomyces ambofaciens* mutants defectve in spiramycin biosynthesis", pp. 3790–3798, 1990.

Kirst, H.A., Progress in Medicinal Chemistry, vol. 31, "Semi–synthetic derivatives of 16–membered macrolide antibiotics", pp. 266–299, 1994.

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 44377 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 350..14002

(ix) FEATURE:
    (A) NAME/KEY: CDS
    (B) LOCATION: 14046..20036

(ix) FEATURE:
    (A) NAME/KEY: CDS
    (B) LOCATION: 20110..31284

(ix) FEATURE:
    (A) NAME/KEY: CDS
    (B) LOCATION: 31329..36071

(ix) FEATURE:
    (A) NAME/KEY: CDS
    (B) LOCATION: 36155..41830

(xi) SEQUENCE DESCRIPTION: SEQ ID NO:1:

```
GACCGCTCGG GGAGACCTGA CATATTCGTC GCGAAGTGGT TGTCCGCGCC GCGAGGTACT      60
GAAATCTTCT CCGCTCGCCC AGGACTCCGC GTGCAGGTCA CCGGAGTGCG CGACCGGCCG     120
GGACGTCGGA GCGCCGACCC TGCGGACCTG GTGCGATGCC GTGTGGTCCC GCATGATCCC     180
GCGCCGTCTC CGGTGACGAG AATCGGTGGA CAATCTCCGA ACTTGACACA ATTGATTGTC     240
GTTCACCGGC CGTTCCTGTC GCCCGGCAGT TCGCCCGCTG TACGCTCGGG AAGATCAAGA     300
AAAGGCAGAA AAGCCACGGC GTGGTACGGC GAACATATGA GGGATGCAGG TGTCTGGAGA     360
ACTCGCGATT TCCCGCAGTG ACGACCGGTC CGACGCCGTT GCCGTGGTCG GAATGGCGTG     420
CCGGTTTCCC GGCGCCCCGG GAATTGCCGA ATTCTGGAAA CTGCTGACCG ACGGAAGGGA     480
CGCGATCGGC CGGGACGCCG ACGGCCGCCG GCGCGGCATG ATCGAGGCGC CCGGCGACTT     540
CGACGCCGCC TTCTTCGGCA TGTCACCCCG CGAGGCCGCC GAGACCGACC CCCAGCAGCG     600
CCTGATGCTC GAACTCGGCT GGGAGGCTCT GGAGGACGCC GGCATCGTCC CCGGCTCCCT     660
GCGCGGCGAG GCGGTCGGCG TCTTCGTCGG GGCCATGCAC GACGACTACG CCACCCTGCT     720
CCACCGCGCC GGCGCGCCGG TCGGCCCCCA CACCGCCACC GGCCTCCAGC GCGCCATGCT     780
CGCCAACCGG CTCTCCTACG TCCTGGGGAC GCGCGGCCCC AGCCTCGCGG TCGACACCGC     840
CCAGTCGTCC TCCCTGGTCG CCGTGGCCCT CGCCGTCGAG AGCCTGCGGG CCGGCACCTC     900
CCGCGTCGCC GTCGCCGGGG GCGTCAACCT GGTCCTCGCC GACGAGGGAA CGGCCGCCAT     960
GGAACGCCTC GGCGCGCTGT CACCCGACGG CCGCTGCCAC ACCTTCGACG CCCGTGCCAA    1020
CGGCTATGTC CGCGGTGAGG GCGGCGCCGC CGTCGTCCTG AAGCCCCTCG CCGACGCCCT    1080
GGCCGACGGG GACCCCGTGT ACTGCGTGGT GCGTGGCGTC GCCGTCGGCA CGACGGCGG     1140
CGGCCCCGGG CTGACCGCTC CCGACCGCGA GGGACAGGAG GCGGTGCTCC GGGCCGCCTG    1200
CGCCCAGGCC CGGGTCGACC CCGCCGAGGT GCGTTTCGTC GAACTGCACG GCACGGGAAC    1260
CCCGGTGGGC GACCCGGTCG AGGCACACGC CCTCGGCGCG GTGCACGGCT CCGGTCGGCC    1320
GGCCGACGAC CCCCTGCTGG TGGGGTCGGT GAAGACCAAC ATCGGCCACC TGGAGGGCGC    1380
CGCCGGCATC GCGGGCCTGG TCAAGGCCGC ACTGTGCCTG CGGGAACGCA CCCTTCCCGG    1440
CTCGCTGAAC TTCGCCACCC CCTCTCCGGC CATCCCGCTG GACCAGCTCC GGCTGAAGGT    1500
GCAGACCGCT GCCGCCGAGC TGCCGCTCGC CCCGGGCGGC GCACCCCTGC TGGCGGGTGT    1560
CAGTTCGTTC GGCATCGGTG GCACCAACTG CCATGTGGTC CTGGAACACC TGCCCTCCCG    1620
GCCCACCCCG GCCGTCTCCG TCGCCGCCTC GCTTCCGGAC GTCCCGCCGC TGTTGTTGTC    1680
CGCGCGGTCG GAGGGGCGT TGCGGGCGCA GGCGGTGCGG TTGGGTGAGT ACGTGGAGCG    1740
GGTGGGCGCG GATCCGCGGG ATGTGGCTTA TTCGCTGGCT TCGACGCGGA CTCTTTTCGA    1800
GCACCGTGCG GTGGTGCCGT GTGGTGGGCG TGGGGAGCTC GTCGCTGCTC TTGGTGGGTT    1860
```

-continued

```
TGCTGCCGGG AGGGTGTCTG GGGGTGTGCG GTCCGGCGG  GCTGTGCCGG GTGGGGTGGG      1920

GGTGTTGTTC ACGGGTCAGG GTGCGCAGTG GGTTGGTATG GGGCGTGGGT TGTATGCGGG      1980

GGGTGGGGTG TTTGCGGAGG TGCTGGATGA GGTGTTGTCG ATGGTGGGGG AGGTGGATGG      2040

TCGGTCGTTG CGGGATGTGA TGTTCGGCGA CGTCGACGTG GACGCGGGTG CCGGGGCTGA      2100

TGCGGGTGCC GGTGCGGGTG CTGGGGTCGG TTCTGGTTCC GGTTCTGTGG GTGGGTTGTT      2160

GGGTCGGACG GAGTTTGCTC AGCCTGCGTT GTTTGCGTTG GAGGTGGCGT TGTTCCGGGC      2220

GTTGGAGGCT CGGGGTGTGG AGGTGTCGGT GGTGTTGGGT CATTCGGTGG GGAGGTGGC      2280

TGCTGCGTAT GTGGCGGGGG TGTTGTCGTT GGGTGATGCG GTGCGGTTGG TGGTGGCGCG      2340

GGGTGGGTTG ATGGGTGGGT TGCCGGTGGG TGGGGGGATG TGGTCGGTGG GGGCGTCGGA     2400

GTCGGTGGTG CGGGGGGTTG TTGAGGGGTT GGGGGAGTGG GTGTCGGTTG CGGCGGTGAA      2460

TGGGCCGCGG TCGGTGGTGT TGTCGGGTGA TGTGGGTGTG CTGGAGTCGG TGGTTGCCTC     2520

GCTGATGGGG GATGGGGTGG AGTGCCGGCG GTTGGATGTG TCGCATGGGT TTCATTCGGT     2580

GTTGATGGAG CCGGTGTTGG GGGAGTTCCG GGGGGTTGTG GAGTCGTTGG AGTTCGGTCG     2640

GGTGCGGCCG GGTGTGGTGG TGGTGTCGGG TGTGTCGGGT GGGGTGGTGG GTTCGGGGGA     2700

GTTGGGGGAT CCGGGGTATT GGGTGCGTCA TGCGCGGGAG GCGGTGCGTT TCGCGGATGG     2760

GGTGGGGGTG GTGCGTGGTC TGGGTGTGGG GACGTTGGTG GAGGTGGGTC CGCATGGGGT    2820

GCTGACGGGG ATGGCGGGTG AGTGCCTGGG GGCCGGTGAT GATGTGGTGG TGGTGCCGGC     2880

GATGCGGCGG GGCCGTGCGG AGCGGGAGGT GTTCGAGGCG GCGCTGGCGA CGGTGTTCAC      2940

CCGGGACGCC GGCCTGGACG CCACGGCACT CCACACCGGG AGCACCGGCC GGCGCATCGA     3000

CCTCCCCACC TACCCCTTCC AACGCCGTAC CCACTGGTCG CCCGCGCTGA GCCGGCCGGT     3060

CACGGCCGAC GCCGGGGCGG GTGTGACCGC CACCGATGCC GTGGGGCACA GCGTCTCCCC     3120

GGACCCGGAG AGCACCGAGG GGACGTCCCA CAGGGACACG GACGACGAGG CGGACTCGGC      3180

GTCACCGGAG CCGATGTCCC CCGAGGATGC CGTCCGCCTG GTCCGCGAGA GCACCGCGGC    3240

CGTCCTGGGC CACGACGATC CCGGCGAGGT CGCGCTCGAC CGCACCTTCA CCTCCCAGGG     3300

CATGGACTCG GTGACCGCGG TCGAGCTGTG CGACCTGCTG AAGGGCGCCT CGGGGCTCCC    3360

CCTCGCCGCC ACGCTGGTCT ACGACCTGCC CACCCCGCGT GCCGTCGCCG AGCACATCGT     3420

GGAAGCCGCG GGCGGGCCGA AGGACTCGGT TGCCGGTGGG CCCGGAGTGC TCTCGTCGGC     3480

CGCGGTAGGG GTGTCGGACG CCCGGGGCGG CAGCCGGGAC GACGACGACC CGATCGCCAT     3540

CGTGGGTGTC GGCTGCCGGC TCCCCGGCGG CGTCGACTCG CGCGCCGCTC TCTGGGAGCT    3600

GCTGGAGTCC GGCGCCGACG CCATCTCGTC CTTCCCCACC GACCGCGGCT GGGACCTCGA     3660

CGGGCTGTAC GACCCCGAGC CCGGGACGCC CGGCAAGACC TATGTGCGGG AGGGCGGGTT     3720

CCTGCACTCG GCGCCGAGT TCGACGCGGA GTTCTTCGGG ATATCGCCGC GCGAGGCCAC      3780

GGCCATGGAC CCGCAGCAGC GCTTGCTGCT GGAAGCGTCG TGGGAGGCCC TCGAGGACGC     3840

CGGAGTGCTC CCCGAGTCAC TGCGCGGCGG CGACGCCGGA GTGTTCGTCG GCGCCACCGC     3900

ACCGGAGTAC GGGCCGAGGC TTCACGAGGG AGCGGACGGA TACGAGGGGT ACCTGCTCAC     3960

CGGCACCACC GCGAGCGTGG CCTCCGGCCG GATCGCCTAC ACCCTCGGCA CCGGCGGACC     4020

GGCGCTCACC GTCGACACCG CGTGCTCCTC GTCCCTGGTG GCGCTGCACC TGGCCGTGCA     4080

GGCGCTGCGC CGGGGCGAGT GCGGGCTGGC TCTGGCGGGC GGCGCCACGG TGATGTCGGG     4140

GCCCGGCATG TTCGTGGAGT TCTCGCGCGCA GCGCGGGCTC GCCCCCGACG GCCGCTGCAT    4200

GCCGTTCTCC GCCGATGCCG ACGGTACGGC CTGGTCCGAG GGTGTCGCCG TACTGGCACT    4260
```

```
GGAGCGGCTC TCCGACGCCC GGCGTGCGGG ACACCGGGTG CTGGGCGTGG TGCGGGGCAG      4320

TGCGGTCAAC CAGGACGGTG CCAGCAACGG CCTGACCGCT CCCAACCGCT CCGCGCAGGA      4380

GGGCGTCATC CGAGCTGCCC TGGCCGACGC CGGCCTCGCG CCGGGTGACG TGGACGCGGT      4440

GGAGGCGCAC GGTACGGGGA CGGCGCTGGG CGATCCGATC GAGGCGAGCG CGCTGCTGGC      4500

CACGTACGGG CGTGAGCGGG TGGGCGACCC CTTGTGGCTC GGGTCGCTGA AGTCCAACGT      4560

CGGTCACACC CAGGCCGCCG CGGGGCCGC GGGTGTGGTC AAGATGCTGC TTGCCCTGGA      4620

GCACGGCACG CTGCCGCGGA CACTTCACGC GGACCGGCCC AGCACGCACG TCGACTGGTC      4680

GTCGGGCACC GTCGCCCTGC TGGCAGAGGC GCGCCGGTGG CCCCGGCGGT CGGACCGCCC      4740

GCGCCGGGCG GCTGTGTCGT CGTTCGGGAT CAGTGGGACG AACGCGCATC TGATCATCGA      4800

GGAGGCGCCG GAGTGGGTCG AGGACATCGA CGGCGTCGCT GCTCCTGACC GCGGTACCGC      4860

GGACGCGGCT GCTCCGTCGC CGCTGTTGTT GTCCGCGCGG TCGGAGGGGG CGTTGCGGGC      4920

GCAGGCGGTG CGGTTGGGTG AGTACGTGGA GCGGGTGGGT GCGGATCCGC GGGATGTGGC      4980

TTATTCGCTG GCTTCGACGC GGACTCTTTT CGAGCACCGT GCGGTGGTGC CGTGTGGTGG      5040

GCGTGGGGAG CTCGTCGCTG CTCTTGGTGG GTTTGCTGCC GGGAGGGTGT CTGGGGGTGT      5100

GCGGTCCGGG CGGGCTGTGC CGGGTGGGGT GGGGGTGTTG TTCACGGGTC AGGGTGCGCA      5160

GTGGGTTGGT ATGGGCGTG GGTTGTATGC GGGGGGTGGG GTGTTTGCGG AGGTGCTGGA      5220

TGAGGTGTTG TCGATGGTGG GGGAGGTGGA TGGTCGGTCG TTGCGGGATG TGATGTTCGG      5280

CGACGTCGAC GTGGACGCGG GTGCCGGGGC TGATGCGGGT GCCGGTGCGG GTGCTGGGGT      5340

CGGTTCTGGT TCCGGTTCTG TGGGTGGGTT GTTGGGTCGG ACGGAGTTTG CTCAGCCTGC      5400

GCTGTTTGCG TTGGAGGTGG CGTTGTTCCG GGCGTTGGAG GCTCGGGGTG TGGAGGTGTC      5460

GGTGGTGTTG GGTCATTCGG TGGGGAGGT GGCTGCTGCG TATGTGGCGG GGGTGTTGTC      5520

GTTGGGTGAT GCGGTGCGGT TGGTGGTGGC GCGGGGTGGG TTGATGGGTG GGTTGCCGGT      5580

GGGTGGGGGG ATGTGGTCGG TGGGGCGTC GGAGTCGGTG GTGCGGGGGG TTGTTGAGGG      5640

GTTGGGGGAG TGGGTGTCGG TTGCGGCGGT GAATGGGCCG CGGTCGGTGG TGTTGTCGGG      5700

TGATGTGGGT GTGCTGGAGT CGGTGGTTGC CTCGCTGATG GGGGATGGGG TGGAGTGCCG      5760

GCGGTTGGAT GTGTCGCATG GGTTTCATTC GGTGTTGATG GAGCCGGTGT TGGGGGAGTT      5820

CCGGGGGGTT GTGGAGTCGT TGGAGTTCGG TCGGGTGCGG CCGGGTGTGG TGGTGGTGTC      5880

GGGTGTGTCG GGTGGGGTGG TGGGTTCGGG GGAGTTGGGG GATCCGGGGT ATTGGGTGCG      5940

TCATGCGCGG GAGGCGGTGC GTTTCGCGGA TGGGGTGGGG GTGGTGCGTG GTCTGGGTGT      6000

GGGGACGTTG GTGGAGGTGG GTCCGCATGG GGTGCTGACG GGGATGGCGG GTGAGTGCCT      6060

GGGGGCCGGT GATGATGTGG TGGTGGTGCC GGCGATGCGG CGGGGCCGTG CGGAGCGGGA      6120

GGTGTTCGAG GCGGCGCTGG CGACGGTGTT CACCCGGGAC GCCGGCCTGG ACGCCACGGC      6180

ACTCCACACC GGGAGCACCG GCCGGCGCAT CGACCTCCCC ACCTACCCCT TCCAACGCGA      6240

CCGCTACTGG CTGGACCCCG TTCGCACCGC CGTGACCGGC GTCGAGCCCG CCGGCTCGCC      6300

GGCGGACGCT CGGGCCACTG AGCGGGGACG GTCGACGACG GCCGGGATCC GCTACCGCGT      6360

CGCTTGGCAG CCGGCCGTCG TCGACCGCGG CAACCCCGGG CCTGCCGGTC ATGTGCTGCT      6420

TCTGGCCCCG GACGAGGACA CGGCCGACTC CGGACTCGCC CCCGCGATCG CACGTGAACT      6480

CGCCGTGCGC GGGGCCGAGG TCCACACCGT CGCCGTGCCG GTCGGTACAG GCCGGGAGGC      6540

AGCCGGGGAC CTGTTGCGGG CCGCCGGTGA CGGTGCCGCC CGCAGCACCC GAGTTCTGTG      6600

GCTCGCCCCG GCCGAGCCGG ACGCGGCCGA CGCCGTCGCC CTCGTCCAGG CGCTGGGCGA      6660
```

```
GGCGGTACCC GAAGCCCCGC TCTGGATCAC CACCCGTGAG GCGGCGGCCG TGCGGCCGGA    6720

CGAGACCCCT TCCGTCGGGG GCGCTCAGCT GTGGGACTC GGACAGGTCG CCGCGCTCGA     6780

ACTGGGGCGG CGCTGGGGCG GCTTGGCGGA CCTGCCCGGG AGTGCGTCGC CCGCGGTGCT    6840

CCGTACGTTC GTCGGGCGC TGCTCGCCGG GGGAGAGAAC CAGTTCGCGG TACGGCCCTC     6900

CGGCGTCCAT GTCCGCCGTG TGGTTCCCGC GCCCGTCCCC GTCCCGGCCT CCGCTCGCAC    6960

CGTCACCACG GCCCCCGCCA CCGCCGTCGG CGAGGACGCA CGGAACGACA CCTCGGACGT    7020

GGTCGTGCCG GACGACCGGT GGTCCTCCGG CACCGTACTG ATCACCGGGG GCACCGGTGC    7080

CCTGGGTGCG CAGGTCGCCC GCAGGCTCGC CCGGTCGGGC GCCGCGCGTC TGCTCCTGGT    7140

GGGCCGGCGC GGCGCGGCCG GCCCCGGAGT GGGCGAACTC GTCGAGGAGC TGACGGCGCT    7200

CGGTTCCGAA GTGGCCGTCG AGGCCTGCGA CGTCGCCGAC CGGGACGCAC TGGCCGCGCT    7260

CCTCGCGGGC CTCCCCGAGG AGCGGCCCCT CGTCGCCGTA CTGCACGCGG CAGGTGTGCT    7320

CGACGACGGT GTGCTCGACT CGCTCACCTC CGACCGGGTG GACGCCGTAC TGCGGGACAA    7380

GGTCACCGCC GCCCGTCACC TGGACGAGCT GACCGCGGAC CTTCCGCTCG ACGCCTTCGT    7440

GCTCTTCTCC TCCATCGTCG GCGTGTGGGG CAACGGAGGG CAGGCCGTCT ACGCGGCCGC    7500

CAACGCCGCG CTCGACGCCC TGGCGCAGCG GCGCCGGGCC AGGGGAGCCC GTGCCGCCTC    7560

GATCGCCTGG GGGCCGTGGG CCGGTGCCGG AATGGCCTCC GGAACGGCGG CGAAGTCCTT    7620

CGAACGGGAC GGCGTCACGG CCCTGGACCC CGAGCGCGCG CTCGACGTCC TCGACGACGT    7680

GGTGGGCGCC GGCGGGACCT CTGCCGCAGG GACGCACGCG GCCGGCGAGA GCTCCCTGCT    7740

CGTCGCCGAC GTGGACTGGG AGACCTTCGT CGGGCGTTCG GTCACCCGCC GTACCTGGTC    7800

GCTCTTCGAC GGCGTCTCCG CCGCCCGTTC GGCGCGTGCC GGCCATGCCG CGGACGACCG    7860

TGCCGCTCTC ACCCCAGGGA CGCGGCCGGG CGACGGCGCA CCGGGCGGGA GCGGACAGGA    7920

CGGGGGCGAG GGCCGGCCGT GGCTCTCCGT CGGCCCCTCG CCGGCGGAAC GCCGTCGTGC    7980

TCTGCTCACG CTTGTGCGCT CGGAGGCCGC CGGGATCCTG CGCCACGCCT CGGCCGACGC    8040

GGTCGACCCG GAGCTGGCCT TCCGGTCCGC CGGGTTCGAC TCCCTCACCG TTCTCGAACT    8100

GCGTAACCGC CTGACCGCTG CCACCGGCCT GAACCTGCCG AACACGCTGC TCTTCGACCA    8160

CCCGACCCCC CTCTCGCTCG CCTCCCACCT GCACGACGAA CTGTTCGGTC CGACAGCGA    8220

GGCGGAGCCG GCAGCGGCCG CCCCCACGCC GGTCATGGCC GACGAGCGTG AGCCGATCGC    8280

GATCGTGGGC ATGGCGTGCC GTTACCCGGG CGGTGTGGCG TCGCCGGACG ACCTGTGGGA    8340

CCTGGTGGCC GGTGACGGGC ACACGCTCTC CCCGTTCCCG GCCGACCGTG GCTGGGACGT    8400

CGAGGGGCTG TACGACCCGG AGCCGGGGGT GCCGGGCAAG AGCTATGTAC GGGAAGGCGG    8460

GTTCCTGCGT TCCGCGGCCG AGTTCGACGC GGAGTTCTTC GGGATATCGC CGCGCGAGGC    8520

CACGGCCATG GACCCGCAGC AGCGGTTGCT GCTGGAGACG TCGTGGGAGG CGCTGGAGCG    8580

GGCCGGCATC GTTCCGGACT CGCTGCGCGG CACCCGGACC GGTGTCTTCA GCGGCATCTC    8640

CCAGCAGGAC TACGCGACCC AGCTGGGGGA CGCCGCCGAC ACCTACGCG GGCATGTGCT     8700

CACGGGGACC CTCGGCAGTG TGATCTCCGG TCGGGTTGCC TATGCGTTGG GGTTGGAGGG    8760

GCCGGCGCTG ACGGTGGACA CGGCGTGTTC GTCGTCGTTG GTGGCGTTGC ATCTGGCGGT    8820

GCAGTCGTTG CGGCGGGGTG AGTGTGATCT GGCGTTGGCC GGTGGGGTGA CGGTGATGGC    8880

GACGCCGACG GTGTTCGTGG AGTTCTCGCG GCAGCGGGGG CTGGCGGCGG ACGGGCGGTG    8940

CAAGGCGTTC GCGGAGGGTG CGGACGGGAC GGCGTGGGCG GAGGGTGTGG GTGTGCTGCT    9000

GGTGGAGCGG CTTTCCGACG CGCGCCGCAA CGGTCATCGG GTGCTGGCGG TGGTGCGGGG    9060
```

-continued

```
CAGTGCGGTC AATCAGGACG GTGCGAGCAA TGGGCTGACG GCGCCGAGTG GTCCGGCGCA    9120

GCAGCGGGTG ATCCGTGAGG CGCTGGCTGA TGCGGGCTG GTGCCCGCCG ACGTGGATGT    9180

GGTGGAGGCG CACGGTACGG GGACGGCGCT GGGTGATCCG ATCGAGGCGG GTGCGCTGCT    9240

GGCCACGTAC GGGCGGAGC GGGTCGGCGA TCCGTTGTGG CTCGGGTCGT TGAAGTCGAA    9300

CATCGGGCAT GCGCAGGCGG CTGCGGGTGT GGGTGGTGTG ATCAAGGTGG TGCAGGGGAT    9360

GCGGCATGGG TCGTTGCCGC GGACGCTGCA TGTGGATGCG CCGTCGTCGA AGGTGGAGTG    9420

GGCTTCGGGT GCGGTGGAGC TGCTGACCGA GACCCGGTCG TGGCCGCGGC GGGTGGAGCG    9480

GGTGCGGCGG GCCGCGGTGT CGGCGTTCGG GGTGAGCGGG ACCAACGCCC ATGTGGTCCT    9540

GGAGGAAGCG CCGGCGGAGG CCGGGAGCGA GCACGGGGAC GGCCCTGAAC CTGAGCGGCC    9600

CGACGCGGTG ACGGGTCCGT TGTCGTGGGT GCTTTCTGCG CGGTCGGAGG GGGCGTTGCG    9660

GGCGCAGGCG GTGCGGTTGC GTGAGTGTGT GGAGCGGGTG GGTGCGGATC CGCGGGATGT    9720

GGCGGGGTCG TTGGTGGTGT CGCGTGCGTC GTTCGGTGAG CGTGCGGTGG TGGTGGGCCG    9780

GGGGCGTGAG GAGTTGCTGG CGGGTCTGGA TGTGGTGGCT GCCGGGGCTC CTGTGGGTGT    9840

GTCTTCGGGG GCCGGTGCTG TGGTGCGGGG GAGTGCGGTG CGGGTCGTG GGGTGGGGGT    9900

GTTGTTCACG GGTCAGGGTG CGCAGTGGGT TGGTATGGGG CGTGGGTTGT ATGCGGGGGG    9960

TGGGGTGTTT GCGGAGGTGC TGGATGAGGT GTTGTCGGTG GTGGGGGAGG TGGATGGTCG   10020

GTCGTTGCGG GATGTGATGT TCGCGGATGC TGACTCGGTT TTGGGTGGGT TGTTGGGTCG   10080

GACGGAGTTT GCTCAGCCTG CGTTGTTTGC GTTGGAGGTG GCGTTGTTCC GGGCGTTGGA   10140

GGCTCGGGGT GTGGAGGTGT CGGTGGTGTT GGGTCATTCG GTGGGGGAGG TGGCTGCTGC   10200

GTATGTGGCG GGGGTGTTGT CGTTGGGTGA TGCGGTGCGG TTGGTGGTGG CGCGGGGTGG   10260

GTTGATGGGT GGGTTGCCGG TGGGTGGGGG GATGTGGTCG GTGGGGCGT CGGAGTCGGT   10320

GGTGCGGGGG GTTGTTGAGG GGTTGGGGGA GTGGGTGTCG GTTGCGGCGG TGAATGGGCC   10380

GCGGTCGGTG GTGTTGTCGG GTGATGTGGG TGTGCTGGAG TCGGTGGTTG TCACGCTGAT   10440

GGGGGATGGG GTGGAGTGCC GGCGGTTGGA TGTGTCGCAT GGGTTTCATT CGGTGTTGAT   10500

GGAGCCGGTG TTGGGGGAGT TCCGGGGGGT TGTGGAGTCG TTGGAGTTCG GTCGGGTGCG   10560

GCCGGGTGTG GTGGTGGTGT CGGGTGTGTC GGGTGGGGTG GTGGGTTCGG GGGAGTTGGG   10620

GGATCCGGGG TATTGGGTGC GTCATGCGCG GGAGGCGGTG CGTTTCGCGG ATGGGGTGGG   10680

GGTGGTGCGT GGTCTGGGTG TGGGGACGTT GGTGGAGGTG GGTCCGCATG GGGTGCTGAC   10740

GGGGATGGCG GGTCAGTGCC TGGAGGCCGG TGATGATGTG GTGGTGGTGC CGGCGATGCG   10800

GCGGGGCCGT CCGGAGCGGG AGGTGTTCGA GGCGGCGCTG GCGACGGTGT TCACCCGGGA   10860

CGCCGGCCTC GACGCCACGA CACTCCACAC CGGGAGCACC GGCCGACGCA TCGACCTCCC   10920

CACCTACCCC TTCCAACACA ACCGCTACTG GGCAACCGGC TCAGTGACCG GTGCGACCGG   10980

CACCTCGGCA GCCGCGCGCT TCGGCCTGGA GTGGAAGGAC CACCCCTTCC TCAGCGGCGC   11040

CACGCCGATA GCCGGCTCCG GCGCGCTGCT CCTCACCGGC AGGGTGGGGC TCGCTGCCCA   11100

CCCGTGGCTG GCCGACCACG CCATCTCCGG CACGGTGCTG CTCCCCGGAA CGGCGATCGC   11160

CGACCTGCTG CTGCGGGCGG TCGAGGAGGT CGGCGCCGGA GGGGTCGAGG AACTGACGCT   11220

CCATGAGCCC CTGCTCCTCC CCGAGCGAGG CGGCCTGCAC GTCCAGGTGC TGGTCGAGGC   11280

GGCCGACGAG CAGGGACGGC GTGCCGTGGC AGTCGCCGCA CGCCCGGAGG GCCCTGGGCG   11340

GGACGGTGAG GAACAGGAGT GGACCCGGCA CGCGGAAGGC GTGCTCACCT CCACCGAGAC   11400

GGCCGTTCCG GACATGGGCT GGGCCGCCGG GGCCTGGCCG CCGCCCGGTG CCGAGCCGAT   11460
```

```
CGACGTCGAG GAGCTGTACG ACGCGTTCGC CGCGGACGGC TACGGCTACG GCCCGGCCTT   11520

CACCGCACTG TCCGGCGTGT GGCGTCTCGG CGACGAACTC TTCGCCGAGG TGCGGCGGCC   11580

CGCGGGGGGC GCGGGCACGA CCGGTGACGG TTTCGGCGTC CACCCCGCAC TCTTCGATGC   11640

GGCCCTCCAC CCGTGGCGCG CCGGCGGGCT GCTGCCCGAC ACGGGCGGCA CCACCTGGGC   11700

GCCGTTCTCC TGGCAGGGCA TCGCGCTCCA CACCACCGGA GCCGAGACGC TCCGCGTCAG   11760

ACTGGCCCCT GCGGCCGGCG GCACCGAGTC GGCCTTCTCC GTACAGGCCG CCGACCCGGC   11820

GGGCACCCCG GTCCTCACCC TCGACGCACT GCTGCTCCGC CCGGTGACCC TGGGGAGGGC   11880

CGACGCGCCG CAACCGCTGT ACCGCGTCGA CTGGCAGCCG GTCGGCCAGG GGACCGAGGC   11940

CTCCGGCGCC CAGGGCTGGA CGGTGCTCGG GCAGGCCGCG GCCGAGACGG TCGCGCAGCC   12000

CGCCGCCCAT GCGGACCTCA CCGCCCTGCG TACGGCTGTG GCCGCGGCGG GAACACCCGT   12060

GCCCCGGCTG GTGGTCGTGT CGCCGGTGGA CACCCGGCTG GACGAGGGGC CGGTGCTGGC   12120

GGACGCCGAG GCTCGGGCCC GTGCGGGTGA CGGCTGGGAC GACGATCCCC TACGTGTCGC   12180

CCTCGGGCGC GGCCTGACCC TGGTCCGGGA GTGGGTCGAG GACGAACGGT TGGCGGACTC   12240

CCGGCTCGTC GTCCTCACCC GTGGCGCGGT GGCGGCCGGT CCCGGCGATG TGCCGGACCT   12300

GACAGGTGCG GCCCTGTGGG GGCTGCTCCG CTCCGCGCAG TCGGAGTATC CGGACCGCTT   12360

CACCCTCATC GACGTGGACG ATTCCCCCGA GTCCCGTGCG GCTCTGCCCC GGGCTCTGGG   12420

ATCGGCCGAG CGACAACTCG CCCTGCGGAC GGGCGACGTG CTGGCGCCGG CCCTGGTCCC   12480

GATGGCCACC CGGCCGGCGG AGACCACTCC AGCGACGGCG GTCGCCTCGG CGACAACACA   12540

GACACAGGTC ACCGCGCCCG CTCCCGACGA CCCGGCTGCG GATGCCGTGT TCGACCCGGC   12600

GGGCACCGTA CTGATCACCG GCGGCACCGG CGCCCTGGGA CGGCGTGTCG CCTCGCACCT   12660

CGCGCGCCGG TACGGCGTAC GCCACATGCT TCTGGTCAGC AGGCGTGGAC CGGACGCCCC   12720

CGAGGCCGGT CCCCTGGAAC GGGAACTCGC CGGTCTCGGA GTCACCGCCA CCTTCCTGGC   12780

ATGCGACCTC ACCGACATCG AGGCCGTACG GAAGGCCGTC GCCGCGGTGC CGTCGGACCA   12840

CCCGCTGACC GGTGTGGTGC ACACCGCCGG CGTGCTGGAC GACGGCGCCC TGACCGGCCT   12900

GACCCGGCAA CGCCTCGACA CCGTGCTGCG GCCCAAGGCC GACGCCGTGC GGAACCTCCA   12960

CGAGGCGACC CTCGACCGGC CGCTGCGCGC GTTCGTCCTG TTCTCCGCCG CCGCCGGACT   13020

CCTGGGCCGC CCCGGGCAGG CCTCCTACGC CGCCGCCAAC GCGGTCCTCG ACGCGCTCGC   13080

GGGAGCCCGC CGCGCGGCCG GACTGCCCGC AGTGTCCCTG GCGTGGGGCC TGTGGGACGA   13140

GCAGACGGGC ATGGCAGGAG GCCTCGACGA GATGGCCCTG CGCGTGCTGC GCCGGGACGG   13200

CATCGCCGCG ATGCCTCCGG AGCAGGGGCT CGAACTGCTC GACCTGGCCC TGACCGGACA   13260

CCGGGACGGA CCCGCCGTCC TCGTCCCCCT CCTCCTCGAC GGCGCGGCCC TGCGCCGCAC   13320

GGCGAAGGAG CGCGGCGCGG CCACGATGTC CCCCTTGCTG CGCGCCCTGC TGCCCGCCGC   13380

CCTGCGCCGC AGCGGTGGAG CCGGCGCCCC CGCGGCGGCC GACCGGCACG GCAAGGAGGC   13440

GGACCCCGGT GCGGGACGCC TCGCAGGGAT GGTGGCACTC GAAGCGGCGG AGCGTTCCGC   13500

GGCCGTCCTT GAGCTGGTCA CCGAACAGGT CGCCGAGGTC CTCGGCTACG CGTCGGCCGC   13560

GGAGATCGAG CCCGAACGAC CCTTCCGGGA GATCGGCGTC GACTCCCTGG CGGCGGTGGA   13620

GCTGCGCAAC CGGCTCAGCC GTCTGGTCGG CCTGCGCGTTG CCGACCACGC TGTCCTTCGA   13680

CCACCCCACG CCGAAGGACA TGGCGCAGCA CATCGACGGG CAGCTCCCCC GCCCGGCCGG   13740

AGCCTCGCCC GCGGACGCAG CGCTGGAAGG GATCGGCGAC CTCGCGCGGG CGGTCGCCCT   13800

GCTGGGCACG GGCGACGCCC GCCGGGCCGA GGTACGAGAG CAGCTCGTCG GACTGCTGGC   13860
```

```
CGCGCTCGAC CCACCTGGGC GGACGGGCAC CGCCGCACCC GGCGTCCCCT CCGGTGCCGA    13920

TGGCGCGGAA CCGACCGTGA CGGACCGGCT CGACGAGGCG ACCGACGACG AGATCTTCGC    13980

CTTCCTGGAC GAGCAGCTGT GACCACACCG TGGACCGACC GCATGCCGAG GAGTTGGTGG    14040

CAGCAATGAC CGCCGAGAAC GACAAGATCC GCAGCTACCT GAAGCGTGCC ACCGCCGAAC    14100

TGCACCGGAC CAAGTCCCGC CTGGCCGAGG TCGAGTCGGC GAGCCGCGAG CCGATCGCGA    14160

TCGTGGGCAT GGCGTGCCGT TACCCGGGCG GTGTGGCGTC GCCGGACGAC CTGTGGGACC    14220

TGGTGGCAGC CGGTACGGAC GCGGTCTCCG CGTTCCCCGT CGACCGTGGC TGGGACGTCG    14280

AGGGGCTGTA CGACCCCGAT CCGGAGGCGG TGGGGCGTAG TTACGTGCGG GAGGGCGGGT    14340

TCCTGCACTC GGCGGCCGAG TTCGACGCGG AGTTCTTCGG GATCTCGCCC CGTGAGGCGG    14400

CGGCGATGGA TCCGCAGCAG CGGTTGCTGC TGGAGACGTC GTGGGAGGCG CTGGAGCGGG    14460

CGGGGATCGT CCCCGCGTCG CTGCGCGGCA CCCGTACCGG CGTCTTCACC GGCGTCATGT    14520

ACGACGACTA CGGGTCGCGG TTCGACTCGG CTCCGCCGGA GTACGAGGGC TACCTCGTGA    14580

ACGGCAGCGC CGGCAGCATC GCGTCCGGTC GGGTTGCCTA TGCGTTGGGG TTGGAGGGGC    14640

CGGCGCTGAC GGTGGACACG GCGTGTTCGT CGTCGTTGGT GGCGTTGCAT CTGGCGGTGC    14700

AGTCGTTGCG GCGGGGTGAG TGTGATCTGG CGTTGGCCGG TGGGGTGACG GTGATGGCGA    14760

CGCCGACGGT GCTCGTGGAG TTCTCGCGGC AGCGGGGCT GGCGGCGGAC GGGCGGTGCA    14820

AGGCGTTCGC GGAGGGTGCG GACGGGACGG CGTGGGCCGA GGGTGTGGGC GTGCTGCTGG    14880

TGGAGCGGCT CTCCGACGCC CGCCGCAATG GCCATCGGGT GCTGGCGGTG GTGCGGGCA    14940

GTGCGGTCAA TCAGGACGGT GCGAGCAACG GGCTGACGGC GCCGAGTGGT CCTGCGCAGC    15000

AGCGGGTGAT CCGTGAGGCG CTGGCCGACG CGGGGCTGAC GCCCGCCGAC GTCGACGCGG    15060

TCGAGGCGCA CGGCACCGGC ACACCCTGG GCGACCCCAT CGAGGCGGGT GCGTTGCTGG    15120

CCACCTATGG CAGTGAGCGC CAGGGCCAAG GTCCGTTGTG GTTGGGGTCG TTGAAGTCGA    15180

ACATCGGGCA TGCGCAGGCG GCTGCGGGTG TGGGTGGCGT GATCAAGGTG GTGCAGGCGA    15240

TGCGGCATGG GTCGTTGCCG CGGACGCTGC ATGTGGATGC GCCGTCGTCG AAGGTGGAGT    15300

GGGCTTCGGG TGCGGTGGAG CTGCTGACCG AGACCCGGTC GTGGCCGCGG CGGGTGGAGC    15360

GGGTGCGGCG GGCCGCGGTG TCGGCGTTCG GGGTGAGCGG GACCAACGCC CATGTGGTCC    15420

TGGAGGAAGC GCCGGCGGAG GCCGGGAGCG AGCACGGGGA CGGCCCTGAA CCCGAGCGGC    15480

CCGACGCGGT GACGGGTCCG TTGTCGTGGG TGCTTTCTGC GCGGTCGGAG GGGGCGTTGC    15540

GGGCGCAGGC GGTGCGGTTG CGTGAGTGTG TGGAGCGGGT GGGTGCGGAT CCGCGGGATG    15600

TGGCGGGGTC GTTGGTGGTG TCGCGTGCGT CGTTCGGTGA GCGTGCGGTG GTGGTGGGCC    15660

GGGGGCGTGA GGAGTTGCTG GCGGGTCTGG ATGTGGTGGC TGCCGGGGCT CCTGTGGGTG    15720

TGTCCGGGGG CGTGTCTTCG GGGGCCGGTG CTGTGGTGCG GGGGAGTGCG GTGCGGGGTC    15780

GTGGGGTGGG GGTGTTGTTC ACGGGTCAGG GTGCGCAGTG GGTTGGTATG GGGCGTGGGT    15840

TGTATGCGGG GGGTGGGGTG TTTGCGGAGG TGCTGGATGA GGTGTTGTCG GTGGTGGGGG    15900

AGGTGGGGGG TTGGTCGTTG CGGGATGTGA TGTTCGGCGA CGTCGACGTG GACGCGGGTG    15960

CCGGGGCTGA TGCGGGTGTC GGTTCGGGTG TTGGTGTGGG TGGGTTGTTG GGTCGGACGG    16020

AGTTTGCTCA GCCTGCGTTG TTTGCGTTGG AGGTGGCGTT GTTCCGGGCG TTGGAGGCTC    16080

GGGGTGTGGA GGTGTCGGTG GTGTTGGGTC ATTCGGTGGG GGAGGTGGCT GCTGCGTATG    16140

TGGCGGGGGT GTTGTCGTTG GGTGATGCGG TGCGGTTGGT GGTGGCGCGG GGTGGGTTGA    16200

TGGGTGGGTT GCCGGTGGGT GGGGGGATGT GGTCGGTGGG GGCGTCGGAG TCGGTGGTGC    16260
```

-continued

```
GGGGGGTTGT TGAGGGGTTG GGGGAGTGGG TGTCGGTTGC GGCGGTGAAT GGGCCGCGGT    16320

CGGTGGTGTT GTCGGGTGAT GTGGGTGTGC TGGAGTCGGT GGTTGCCTCG CTGATGGGGG    16380

ATGGGGTGGA GTGCCGGCGG TTGGATGTGT CGCATGGGTT TCATTCGGTG TTGATGGAGC    16440

CGGTGTTGGG GGAGTTCCGG GGGGTTGTGG AGTCGTTGGA GTTCGGTCGG GTGCGGCCGG    16500

GTGTGGTGGT GGTGTCGAGT GTGTCGGGTG GGGTGGTGGG TTCGGGGGAG TTGGGGGATC    16560

CGGGGTATTG GGTGCGTCAT GCGCGGGAGG CGGTGCGTTT CGCGGATGGG GTGGGGGTGG    16620

TGCGTGGTCT GGGTGTGGGG ACGTTGGTGG AGGTGGGTCC GCATGGGGTG CTGACGGGGA    16680

TGGCGGGTGA GTGCCTGGGG GCCGGTGATG ATGTGGTGGT GGTGCCGGCG ATGCGGCGGG    16740

GCCGTGCGGA GCGGGAGGTG TTCGAGGCGG CGCTGGCGAC GGTGTTCACC CGGGACGCCG    16800

GCCTGGACGC CACGACACTC CACACCGGGA GCACCGGCCG ACGCATCGAC CTCCCCACCT    16860

ACCCCTTCCA ACACGACCGC TACTGGCTGG CCGCCCCGTC CCGGCCCAGG ACGGACGGGC    16920

TGTCGGCGGC GGGTCTGCGC GAGGTGGAGC ACCCCCTGCT CACCGCCGCC GTGGAACTGC    16980

CCGGCACCGA CACCGAGGTG TGGACCGGCC GCATATCCGC TGCCGACCTG CCCTGGCTCG    17040

CCGACCACCT GGTGTGGGAC CGAGGCGTGG TGCCGGGGAC CGCGCTGCTG GAGACGGTGC    17100

TCCAGGTGGG AAGCCGGATC GGTCTGCCGC GCGTCGCCGA ACTGGTCCTG GAGACGCCGC    17160

TGACCTGGAC GTCGGACCGC CCGCTCCAGG TCCGGATCGT CGTGACCGCT GCCGCCACCG    17220

CCCCCGGGGG CGCGCGTGAG CTGACCCTCC ACTCGCGGCC CGAGCCCGTG GCCGCCTCCT    17280

CGTCCTCCCC GAGTCCCGCC TCTCCCCGGC ACCTCACGGC GCAGGAGAGC GACGACGACT    17340

GGACCCGGCA TGCCTCAGGG CTGCTCGCCC CGGCTGCCGG CCTCGCCGAC GACTTCGCCG    17400

AGCTCACCGG CGCCTGGCCC CCCGTCGGCG CCGAGCCCCT CGACCTCGCC GGTCAGTACC    17460

CGCTCTTCGC AGCCGCCGGA GTGCGCTACG AAGGCGCCTT CCGAGGGCTG CGCGCGGCAT    17520

GGCGTCGAGG CGACGAGGTC TTCGCCGACG TACGGCTGCC CGACGCGCAC GCGGTCGACG    17580

CTGATCGTTA CGGGGTGCAC CCCGCCCTGC TCGACGCGGT GCTCCACCCG ATCGCGTCGC    17640

TGGACCCGCT GGGCGACGGC GGGCACGGTC TGCTGCCGTT CTCCTGGACC GACGTACAGG    17700

GACACGGCGC CGGCGGACAC GCCCTCCGGG TACGGGTGGC GGCCGTCGAC GGCGGCGCGG    17760

TGTCGGTCAC CGCGGCCGAC CACGCGGGCA ACCCGGTGTT ATCCGCCCGG TCCCTGGCAC    17820

TGCGTCGTAT CACCGCGGAC CGGCTTCCCG CCGCGCCCGT CGCCCCTCTC TACCGCGTGG    17880

ACTGGCTGCC GTTCCCGGGT CCGGTGCCCG TATCCGCGGG CGGCCGCTGG GCGGTCGTCG    17940

GACCCGAGGC CGAAGCCACG GCTGCCGGAC TGCGTGCGGT GGGCCTCGAC GTGCGTACCC    18000

ATGCGCTCCC CCTCGGAGAG CCCCTGCCTC CGCAGGCCGG TACCGACGCG GAGGTGATCA    18060

TCCTCGACCT GACCACCACC GCAGCCGGCC GTACGGCGTC GGACGGGGGG CGGCTCAGTC    18120

TCCTCGACGA GGTGCGTGCG ACGGTGCGCC GGACCCTCGA AGCCGTACAG GCCCGCCTCG    18180

CCGACACCGA AACGGCCCCC GACGTCGACG TCCGTACGGC CGCGCGCCCC CGCACAGCCG    18240

CCCGTACAAG CCCCCGCGTG GACACCCGCA CGGGAGCCCG CACCGCTGAC GGCCCCCGGC    18300

TCGTCGTCCT GACCCGGGGC GCGGCCGGAC CCGAGGGAGG CGCGGCCGAT CCCGCGGGTG    18360

CCGCTGTCTG GGGGCTCGTC CGGGTCGCCC AGGCCGAACA GCCCGGCCGC TTCACCCTGG    18420

TGGACGTCGA CGGCACCCAG GCGTCGCTGC GGGCCCTGCC CGGTCTGCTG GCCACGGATG    18480

CCGGCCAGTC GGCCGTGCGC GACGGACGTG TCACCGTCCC GCGCCTCGTC CCGGTGGCCG    18540

ACCCCGTCCC CCACGGCGGC GGCACGGCGG CCGACGGGAC GGGTGCCGGC GAGCCGTCCG    18600

CGACCCTGGA CCCCGAAGGC ACCGTGCTGA TCACCGGCGG CACCGGAGCA CTGGCCGCGG    18660
```

```
AAACCGCCCG GCACCTGGTC GACCGGCACA AGGTGCGCCA TCTCCTGCTG GTGGGCAGGC  18720

GCGGTCCCGA CGCACCCGGC GTCGATCGAC TGGTCGCCGA GTTGACCGAG TCGGGTGCCG  18780

AGGTCGCCGT ACGGGCCTGT GACGTCACGG ACCGCGACGC CCTGCGCCGC CTGCTCGACG  18840

CACTCCCCGA CGAACACCCG CTGACCTGCG TGGTGCACAC CGCCGGGGTG CTCGACGACG  18900

GCGTGCTCTC CGCCCAGACG GCCGAGCGGA TCGACACGGT GCTCCGGCCC AAGGCCGACG  18960

CCGCCGTCCA CCTGGACGAG CTGACCCGGG AGATCGGACG GGTGCCCCTG GTGCTGTACT  19020

CCTCGGTCTC GGCCACCCTG GGCAGCGCGG GGCAGGCCGG GTACGCGGCG CCAACGCCT   19080

TCATGGACGC GCTGGCCGCC CGGCGGTGCG CCGCCGGGCA CCCCGCGCTG TCGCTCGGCT  19140

GGGGCTGGTG GTCCGGGGTG GGTCTCGCCA CCGGACTGGA CGGAGCGGAC GCGGCGCGGG  19200

TCAGGCGCTC GGGTCTCGCC CCGCTCGACG CCGGCGCCGC ACTGGACCTG CTCGACCGGG  19260

CGCTGACCCG GCCCGAGCCG GCCCTGCTGC CCGTGCGGCT CGACCTGCGC GCCGCGGCCG  19320

GTGCCACCGC TCTCCCGGAG GTCCTGCGTG ACCTGGCCGG CGTACCGGCG GACGCCCGCA  19380

GCACGCCCGG GGCCGCGGCG GGCACCGGGG ACGAGGACGG TGCCGTGCGC CCTGCCCCCG  19440

CCCCGGCCGA CGCCGCCGGG ACGCTGGCCG CGCGGCTCGC GGGACGTTCC GCACCCGAGC  19500

GTACGGCTCT CCTGCTCGAC CTGGTGCGGA CCGAGGTCGC GGCGGTGCTC GGACACGGCG  19560

ACCCCGCCGC GATCGGCGCC GCCCGCACCT TCAAGGACGC CGGATTCGAC TCCCTCACCG  19620

CTGTCGACCT CCGCAACCGG CTGAACACAC GCACCGGACT GCGGCTGCCC GCGACCCTCG  19680

TCTTCGACCA CCCCACACCG CTCGCCCTCG CCGAACTCCT GCTCGACGGG CTGGAGGCGG  19740

CCGGTCCAGC GGAACCGGCC GCTGAGGTCC CGGACGAAGC GGCCGGTGCC GAGACCCTGT  19800

CCGGCGTGAT CGACCGGCTG GAACGCAGCC TCGCCGCGAC CGACGACGGC GACGCCCGGG  19860

TCCGCGCGGC ACGGCGGCTG CGCGGCCTGC TGGACGCGCT CCCCGCCGGT CCCGGTGCCG  19920

CGTCCGGTCC GGATGCCGGA GAGCACGCCC CCGGTCGCGG CGACGTGGTG ATCGACCGGC  19980

TCAGGTCGGC CTCCGACGAC GACTTGTTCG ACCTGCTCGA CAGCGACTTC CAGTGAGCCG  20040

GACCGCGCCG CGCGCCGACC GCTGAACCGC TCTTCACCCA GACCCACGAG ACCACGCCTG  20100

AGGAGAACCG TGTCTGCGAC CAACGAGGAG AAGTTGCGGG AGTACCTGCG GCGCGCGATG  20160

GCCGACCTGC ACAGCGCACG AGAGCGGTTG CGCGAGGTCG AGTCGGCGAG CCGTGAGCCG  20220

ATCGCGATCG TGGGCATGGC GTGCCGTTAC CCGGGCGGTG TGGCGTCGCC GGAGGAGCTG  20280

TGGGACCTGG TGGCCGCCGG TACGGACGCG ATCTCCCCGT TCCCCGTCGA CCGCGGCTGG  20340

GACGCCGAGG GTCTGTACGA CCCGGAGCCG GGGGTGCCGG GCAAGAGCTA CGTGCGCGAG  20400

GGCGGGTTCC TGCACTCGGC GGCCGAGTTC GACGCGGAGT TCTTCGGGAT CTCGCCGCGT  20460

GAGGCGGCGG CGATGGATCC GCAGCAGCGG TTGCTGCTGG AGACGTCGTG GGAGGCGCTG  20520

GAGCGGGCCG GGATCGTCCC CGCGTCGCTG CGCGGCACCC GTACCGGCGT CTTCACCGGC  20580

GTCATGTACC ACGACTACGG CAGCCACCAG GTCGGCACCG CCGCCGATCC CAGTGGACAG  20640

CTCGGCCTCG GCACCGCGGG GAGCGTCGCC TCGGGCCGGG TGGCGTACAC CCTCGGTCTA  20700

CAGGGGCCGG CCGTGACCAT GGACACGGCA TGCTCGTCCT CGCTGGTGGC GTTGCACCTG  20760

GCGGTGCAGT CGTTGCGGCG GGGCGAGTGC GATCTCGCGT TGGCCGGCGG GGCGACGGTC  20820

TTGGCGACGC CCACGGTGTT CGTGGAGTTC TCGCGGCAAC GGGGGCTGGC GGCGGACGGA  20880

CGGTGCAAGG CGTTCGCGGA GGGCGCCGAC GGCACGGCGT GGGCCGAGGG CGCCGGTGTG  20940

CTGCTGGTGG AGCGGCTCTC CGACGCCCGC CGCAACGGCC ATCGGGTGCT CGCGGTGGTG  21000

CGGGGCAGCG CGGTCAACCA GGACGGTGCC AGCAACGGCC TCACCGCACC CAGCGGGCCC  21060
```

```
GCCCAGCAGC GGGTGATCCG TGACGCGCTG GCCGACGCGG GGCTGACGCC CGCCGACGTG   21120

GACGCGGTCG AGGCGCACGG CACCGGCACA CCGCTCGGCG ACCCGATCGA GGCCGGCGCG   21180

CTGATGGCCA CCTACGGCAG TGAACGGGTG GGCGACCCGC TGTGGCTGGG TTCGCTGAAG   21240

TCGAACATCG GACACACCCA GGCCGCCGCC GGAGCCGCCG GCGTCATCAA GATGGTGCAG   21300

GCGTTACGGC AGTCCGAGCT GCCGCGCACC CTGCACGTCG ACGCGCCCTC GGCCAAGGTC   21360

GAATGGGACG CGGGCGCCGT GCAACTGCTC ACCGGCGTCC GGCCATGGCC CCGGCGCGAG   21420

CACAGGCCCC GGCGGGCCGC GGTCTCCGCC TTCGGCGTCA GCGGCACCAA CGCCCACGTC   21480

ATCATCGAGG AACCGCCCGC GGCCGGTGAC ACCTCGCCCG CCGGCGACAC CCCTGAGCCG   21540

GGCGAGGCGA CCGCGTCCCC CTCCACCGCG GCCGGGCCGT CGTCCCCCTC CGCGGTGGCC   21600

GGGCCGCTGT CCCCCTCCTC CCCGGCCGTG GTCTGGCCCC TGTCCGCCGA GACCGCCCCC   21660

GCCCTGCGCG CCCAGGCCGC CCGCCTGCGG GCGCACCTCG AACGCCTCCC CGGCACCTCG   21720

CCGACCGACA TCGGCCACGC CCTGGCCGCC GAACGCGCCG CCCTCACCCG ACGCGTCGTG   21780

CTGCTCGGCG ACGACGGAGC CCCGGTCGAC GCACTCGCCG CCCTCGCCGC CGGCGAGACC   21840

ACCCCCGACG CCGTCCACGG CACCGCGGCG GACATCCGCC GGGTCGCCTT CGTGTTCCCC   21900

GGCCAGGGTT CCCAGTGGGC CGGGATGGGC GCCGAACTGC TGGACACGGC CCCGGCCTTC   21960

GCCGCCGAAC TGGACCGCTG CCAGGGCGCG CTCTCCCCGT ACGTGGACTG GAACCTCGCG   22020

GACGTGCTGC GCGGCGCGCC CGCGGCGCCC GGCCTCGACC GGGTCGACGT CGTCCAGCCG   22080

GCCACCTTCG CCGTCATGGT GGGACTCGCC GCGCTGTGGC GCTCCCTCGG GGTCGAACCC   22140

GCCGCCGTCA TCGGCCACTC CCAGGGCGAG ATCGCCGCGG CCTGCGTGGC GGGCGCGCTC   22200

TCCCTGGAGG ACGCCGCCCG GATCGTGGCC CTGCGCTCCC AGGTCATCGC CCGCGAACTG   22260

GCCGGGCGGG GCGGCATGGC CTCGGTGGCC CTGCCCGCGG CGGAGGTCGA GGCCCGCCTG   22320

GCCGGCGGCG TCGAGATCGC CGCCGTCAAC GGCCCCGGCT CGACCGTCGT CTGCGGAGAG   22380

CCCGGCGCCC TGGAGGCGTT GCTCGTCACG CTGGAGAGCG AAGGCACCCG GGTCCGCCGC   22440

ATCGACGTCG ACTACGCGTC CCACTCCCAC TACGTCGAGA GCATCCGGGC GGAACTCGCC   22500

ACCGTCCTCG GCCCCGTCCG GCCGCGGAGG GGCGACGTGC CCTTCTACTC CACCGTCGAG   22560

GCGGCGCTCC TCGACACCGC CACCCTGGAC GCCGACTACT GGTACCGCAA CCTGCGCCTC   22620

CCGGTGCGCT TCGAGCCGAC CGTACGCGCC ATGCTCGACG ACGGCGTCGA CGCGTTCGTG   22680

GAGTGCTCCG CGCATCCCGT CCTGACCGTC GGCGTGCGCC AGACCGTGGA GAGCGCCGGC   22740

GGCGCGGTCC CGGCCCTCGC TTCGCTGCGC CGCGACGAGG GCGGGCTGCG GCGCTTCCTC   22800

ACCTCCGCCG CCGAGGCCCA GGTCGTCGGC GTCCCCGTGG ACTGGGCGAC GCTCCGCCCA   22860

GGCGCCGGCC GGGTGGACCT GCCGACCTAC GCCTTCCAGC GCGAACGCCA CTGGGTCGGC   22920

CCCGCCGGC CCGACTCCGC GGCGACGGCC GCCACGACCG GTGACGACGC CCCGGAGCCC   22980

GGAGACCGGC TCGGCTACCA CGTCGCGTGG AAGGGACTGC GCTCCACCAC CGGCGGCTGG   23040

CGCCCCGGCC TGCGCCTGCT GATCGTGCCC ACCGGGGACC AGTACACCGC CCTCGCCGAC   23100

ACCCTGGAAC AGGCGGTCGC CTCCTTCGGC GGAACGGTCC GCCGCGTCGC CTTCGACCCG   23160

GCACGCACCG GACGCGCCGA GCTGTTCGGC CTGCTCGAGA CGGAGATCAA CGGCGACACC   23220

GCCGTCACCG GCGTCGTCTC GCTGCTCGGA CTGTGCACCG ACGGCAGGCC GGACCACCCC   23280

GCCGTGCCCG TCGCCGTCAC CGCCACCCTC GCCCTCGTCC AGGCCCTGGC CGACCTCGGC   23340

AGCACCGCAC CGCTGTGGAC CGTCACCTGC GGCGCGGTCG CCACCGCCCC CGACGAACTG   23400

CCGTGCACCG CCGGTGCCCA GCTGTGGGGC CTGGGCCGGG TGGCCGCGCT GGAGCTGCCC   23460
```

```
GAGGTGTGGG GCGGCCTCAT CGACCTTCCC GCGCGGCCCG ACGCCCGGGT CCTGGACCGT    23520

CTCGCCGGCG TCCTCGCCGA ACCCGGCGGC GAGGACCAGA TCGCCGTACG GATGGCGGGC    23580

GTCTTCGGCC GCCGGGTCCT GCGGAACCCG GCCGACTCCC GGCCCCCGGC CTGGCGCGCC    23640

CGGGGCACCG TCCTCATCGC CGGCGACCTC ACGACGGTGC CCGGCCGACT GGTCCGGTCC    23700

CTCCTCGAGG ACGGCGCGGA CCGCGTGGTG CTGGCCGGAC CCGACGCCCC CGCACAGGCC    23760

GCCGCCGCCG GACTGACCGG CGTCTCCCTC GTCCCCGTGC GCTGCGACGT CACCGACCGC    23820

GCCGCACTGG CCGCGCTGCT CGACGAGCAC GCGCCCACCG TCGCCGTGCA CGCCCCGCCC    23880

CTGGTGCCCC TGGCGCCGCT GCGGGAGACG GCACCCGGCG ACATCGCCGC CGCCCTCGCC    23940

GCCAAGACCA CGGCCGCCGG CCACCTGGTC GACCTGGCGC CGGCCGCGGG CCTCGACGCG    24000

CTGGTGCTGT TCTCCTCGGT CTCCGGAGTG TGGGGCGGCG CGGCCCAGGG CGGCTACGCG    24060

GCCGCCAGCG CGCACCTCGA CGCGCTGGCC GAACGCGCCC GCGCCGCGGG GGTGCCCGCG    24120

TTCTCCGTGG CCTGGAGCCC CTGGGCCGGA GGCACGCCCG CCGACGGTGC CGAGGCGGAG    24180

TTCCTCAGCC GGCGCGGGCT GGCTCCCCTC GACCCCGACC AGGCGGTGCG GACCCTGCGC    24240

CGCATGCTGG AGCGCGGCAG CGCCTGCGGT GCGGTCGCCG ACGTCGAGTG GAGCCGGTTC    24300

GCCGCCTCCT ACACCTGGGT GCGTCCCGCC GTACTCTTCG ACGACATCCC GGACGTGCAG    24360

CGGCTGCGCG CGGCCGAACT CGCCCCGAGC ACCGGAGACT CGACCACCTC CGAACTCGTC    24420

CGCGAGCTGA CCGCGCAGTC CGGCCACAAG CGGCACGCCA CCCTGCTGCG GCTGGTGCGC    24480

GCACACGCCG CCGCCGTCCT CGGACAGTCC TCCGGCGACG CGGTGAGCAG CGCCCGCGCC    24540

TTCCGCGACC TCGGCTTCGA CTCGCTGACC GCCCTCGAAC TGCGCGACCG GCTCAGCACC    24600

AGCACCGGGC TCAAACTGCC CACCTCCCTG GTCTTCGACC ACTCCAGCCC GGCCGCGCTC    24660

GCCCGGCACC TCGGTGAGGA ACTCCTCGGC CGGAACGACA CCGCCGACCG GGCCGGCCCC    24720

GACACCCCGG TACGGACGGA CGAGCCCATC GCCATCATCG GCATGGCCTG CCGGCTGCCC    24780

GGCGGGGTGC AGTCCCCCGA GGACCTGTGG GACCTGCTGA CCGGTGGGAC CGACGCCATC    24840

ACCCCCTTCC CGACCAACCG GGGATGGGAC AACGAGACCC TCTACGACCC CGACCCCGAC    24900

TCGCCCGGGC ACCACACCTA CGTGCGCGAG GGCGGGTTCC TGCACGACGC GGCCGAGTTC    24960

GACCCCGGCT TCTTCGGCAT CAGCCCCCGC GAGGCCCTGG CCATGGACCC GCAGCAGCGG    25020

CTGATCCTGG AGACGTCCTG GGAGTCCTTC GAACGGGCCG GCATCGACCC GGTCGAACTG    25080

CGCGGCAGCC GCACCGGGGT CTTCGTCGGC ACCAACGGAC AGCACTACGT GCCGCTCCTC    25140

CAGGACGGCG ACGAGAACTT CGACGGCTAC ATCGCCACCG GCAACTCCGC CAGCGTGATG    25200

TCCGGCCGGC TCTCCTACGT CTTCGGACTG GAGGGCCCCG CCGTCACCGT CGACACCGCC    25260

TGCTCGGCCT CCCTGGCCGC ACTGCACCTG GCGGTGCAGT CACTGCGCCG CGGCGAATGC    25320

GACTACGCCC TCGCCGGCGG GGCCACGGTG ATGTCCACCC CCGAGATGCT GGTGGAGTTC    25380

GCCCGTCAGC GAGCGGTGTC GCCGGACGGC CGCAGCAAGG CGTTCGCGGA GGCGGCCGAC    25440

GGGGTCGGTC TCGCCGAGGG AGCCGGGATG CTGCTCGTGG AGCGGCTGTC GGAGGCGCAG    25500

AAGAAGGGCC ATCCGGTACT GGCGGTGGTG CGGGGCAGTG CCGTCAACCA GGACGGTGCC    25560

AGCAACGGCC TCACCGCACC CAGCGGGCCC GCCCAGCAGC GGGTGATACG GGAGGCGCTG    25620

GCCGACGCGG GGCTGACGCC CGCCGACGTG GACGCGGTCG AGGCGCACGG CACCGGCACG    25680

CCGCTCGGCG ACCCCATCGA GGCCGGCGCG CTGCTCGCCA CGTACGGCCG GGACCGGCGC    25740

GACGGCCCGC TGTGGCTGGG TTCGCTGAAG TCGAACATCG GCACACCCA GGCCGCCGCC     25800

GGCGTGGCCG GGGTGATCAA GATGGTGCTG GCGCTGCGCC ACGGCGAGCT GCCGCGCACC    25860
```

-continued

```
CTGCACGCGT CGACGGCGTC GTCCAGGATC GATTGGGACG CGGGCGCCGT GGAGTTGCTG    25920

GACGAGGCCA GGCCCTGGCT CCAGCGGGCC GAGGGGCCGC GCCGGGCGGG CATCTCCTCG    25980

TTCGGCATCA GCGGCACCAA CGCGCACCTC GTCATCGAGG AGCCGCCGGA GCCCACCGCG    26040

CCCGAACTGC TCGCGCCCGA ACCGGCCGCC GACGGCGACG TCTGGTCCGA GGAGTGGTGG    26100

CACGAGGTGA CCGTGCCCCT GATGATGTCC GCGCACAACG AAGCCGCCCT GCGCGACCAG    26160

GCGCGGCGCC TGCGCGCCGA CCTGCTCGCC CACCCCGAGC TGCACCCGGC CGACGTCGGC    26220

TACACCCTCA TCACCACCCG CACCCGGTTC GAGCAGCGGG CCGCCGTCGT CGGCGAGAAC    26280

TTCACGGAGC TGATCGCGGC CCTCGACGAC CTCGTCGAAG GCCGACCGCA CCCGCTCGTG    26340

CTGCGGGGCA CCGCCGGCAC CTCCGACCAG GTCGTGTTCG TCTTCCCCGG CCAGGGCTCG    26400

CAGTGGCCCG AGATGGCCGA CGGGCTGCTG GCCCGCTCCA GCGGCTCCGG CTCCTTCCTG    26460

GAGACCGCCC GCGCCTGCGA CCTCGCGCTC CGGCCCCACC TCGGCTGGTC CGTCCTGGAC    26520

GTACTGCGCC GGGAACCCGG CGCGCCCTCG CTCGACCGGG TCGACGTGGT GCAGCCCGTG    26580

CTGTTCACCA TGATGGTCTC GCTCGCCGAG ACGTGGCGTT CGCTGGGCGT CGAACCGGCC    26640

GCGGTCGTCG GTCACTCCCA GGGCGAGATC GCCGCCGCCT ACGTCGCCGG CGCCCTGACG    26700

CTGGACGACG CGGCGCGCAT CGTCGCCCTG CGCAGCCAGG CGTGGCTGCG GCTGGCCGGC    26760

AAGGGCGGCA TGGTCGCCGT GACCCTGTCC GAACGCGACC TGCGTCCCCG CCTGGAGCCC    26820

TGGAGCGACC GGCTCGCCGT CGCCGCCGTC AACGGCCCCG AGACCTGCGC CGTCTCCGGG    26880

GACCCGGACG CCCTGGCGGA GCTGGTCGCC GAACTCGGTG CGGAGGGCGT GCACGCCCGC    26940

CCCATCCCCG GCGTCGACAC CGCCGGGCAC TCGCCGCAGG TCGACACGCT GGAGGCCCAC    27000

CTGCGGAAGG TGCTCGCGCC CGTCGCGCCC CGCACCTCCG ACATCCCGTT CTACTCGACG    27060

GTCACCGGAG GACTGATCGA CACCGCCGAG CTGGACGCCG ACTACTGGTA CCGCAACATG    27120

CGCGAGCCGG TGGAGTTCGA GCAGGCCACC CGCGCCCTGA TCGCCGACGG CCACGACGTG    27180

TTCCTGGAGT CGAGCCCGCA CCCCATGCTG GCCGTCTCCC TCCAGGAGAC GATCAGCGAC    27240

GCCGGTTCCC CGGCGGCCGT CCTCGGCACC CTGCGGCGCG GCCAGGGCGG CCCCCGCTGG    27300

CTGGGCGTCG CCCTCTGCCG CGCCTACACC CACGGCCTGG AGATCGACGC CGAGGCCATC    27360

TTCGGCCCCG ACTCACGCCA GGTGGAACTG CCCACGTACC CCTTCCAGCG CGAGCGCTAC    27420

TGGTACAGCC CCGGCCACCG CGGTGACGAC CCCGCCTCCC TCGGTCTGGA CGCCGTCGAC    27480

CACCCGCTGC TGGGCAGCGG CGTCGAACTG CCGGAGTCCG GTGACCGGAT GTACACCGCA    27540

CGGCTGGGCG CCGACACCAC CCCGTGGCTG GCCGACCACG CGCTGCTGGG GTCGCCGCTG    27600

CTGCCCGGCG CCGCCTTCGC CGACCTGGCG CTCTGGGCCG GCCGCAGGC CGGCACCGGC    27660

CGCGTCGAGG AGCTCACCCT GGCCGCGCCC CTGGTGCTGC CCGGCTCCGG GGGTGTCCGG    27720

CTGCGGCTGA ACGTCGGCGC CCCGGGCACC GACGACGCCC GCCGCTTCGC CGTGCACGCC    27780

CGCGCCGAGG GCGCCACGGA CTGGACCCTG CACGCCGAGG GGCTGCTCAC CGCGCAGGAC    27840

ACGGCCGACG CGCCGGACGC CTCGGCGGCC ACCCCGCCCC CCGGCGCCGA CAACTGGAC    27900

ATCGGCGACT TCTACCAGCG CTTCTCCGAA CTCGGTTACG GCTACGGCCC GTTCTTCCGG    27960

GGACTGGTGA GCGCCCACCG CTGCGGCCCC GACATCCACG CGGAGGTCGC GCTGCCCGTC    28020

CAGGCGCAGG GCGACGCGGC CCGCTTCGGC ATCCATCCCG CGCTGCTGGA CGCGGCGCTG    28080

CAGACCATGA GCCTCGGGGG CTTCTTCCCC GAGGACGGCC GCGTCCGCAT GCCGTTCGCC    28140

CTGCGCGGCG TTCGGCTGTA CCGCGCCGGA GCCGACCGGC TGCACGTGCG CGTCTCGCCC    28200

GTCTCCGAGG ACGCGGTCCG CATCAGGTGC GCCGACGGCG AGGGACGGCC GGTCGCCGAG    28260
```

```
ATCGAGTCCT TCATCATGCG GCCGGTCGAC CCGGGACAGC TCCTGGGCGG CCGCCCGGTC   28320

GGCGCCGACG CGCTCTTCCG CATCGCCTGG CGGGAACTCG CCGCCGGCCC GGGCACCCGT   28380

ACCGGCGACG GCACCCCTCC CCCGGTGCGC TGGGTGCTGG CGGGACCCGA CGCGCTGGGC   28440

CTGGCCGAGG CGGCCGACGC CCACCTGCCC GCCGTTCCCG GCCCGGACGG CGCACTGCCG   28500

TCCCCGACGG GACGCCCGGC GCCGGACGCC GTCGTGTTCG CGGTCCGTGC CGGGACCGGC   28560

GACGTCGCCG CCGACGCGCA CACCGTGGCC TGCCGGGTGC TGGACCTCGT CCAGCGCCGG   28620

CTCGCGGCCC CGGAGGGCCC GGACGGCGCC CGCCTGGTGG TGGCCACCCG CGGCGCGGTC   28680

GCCGTACGCG ACGACGCCGA GGTGGACGAC CCGGCCGCGG CCGCCGCGTG GGGCCTGCTG   28740

CGCTCCGCGC AGGCCGAGGA GCCCGGCCGG TTCCTGCTCG TGGACCTGGA CGACGACCCG   28800

GCGTCCGCCC GGGCGCTGAC CGACGCCCTC GCCTCCGGCG AACCGCAGAC CGCGGTCCGG   28860

GCCGGGACGG TGTACGTGCC CCGGCTGGAG CGGGCCGCCG ACCGCACGGA CGGGCCGCTC   28920

ACCCCGCCCG ACGACGGTGC CTGGCGGCTG GGCCGGGGCA CCGACCTCAC CCTCGACGGC   28980

CTCGCCCTGG TGCCCGCCCC GGACGCCGAG GCGCCGCTGG AGCCCGGCCA GGTGCGCGTC   29040

GCCGTACGCG CCGCGGGCGT CAACTTCCGC GACGCCCTCA TCGCCCTCGG CATGTACCCG   29100

GGCGAGGCGG AGATGGGAAC GGAGGGCGCC GGCACCGTCG TCGAGGTCGG CCCCGGCGTC   29160

ACCGGTGTCG CCGTCGGCGA CCGCGTGCTC GGCCTGTGGG ACGGCGGCCT GGGCCCGCTG   29220

TGCGTGGCCG ACCACCGGCT GCTCGCCCCC GTCCCGGACG GCTGGTCCTA CGCCCAGGCC   29280

GCCTCGGTCC CCGCGGTGTT CCTCAGCGCC TACTACGGTC TGGTCACCCT GGCCGGCCTC   29340

AGGCCGGGGG AGCGGGTGCT CGTGCACGCC GCCGCCGGGG GCGTCGGCAT GGCCGCGGTG   29400

CAGATCGCCC GCCACCTCGG CGCGGAGGTG CTGGCCACCG CGAGCCCCGG CAAGTGGGAC   29460

GCCCTGCGCG CCATGGGCAT CACCGACGAC CACCTCGCCT CCTCCCGCAC CCTCGACTTC   29520

GCGACCGCCT TCACCGGAGC GGACGGCACG TCCCGCGCGG ACGTCGTCCT GAACTCGCTC   29580

ACCAAGGAGT TCGTGGACGC CTCCCTCGGG CTGCTCCGTC CGGGCGGCCG GTTCCTGGAG   29640

CTGGGCAAGA CCGACGTCCG GGACCCCGAG CGGATCGCCG CCGAACACCC CGGGGTGCGC   29700

TACCGGGCGT TCGACCTCAA CGAGGCCGGA CCCGACGCAC TCGGCCGGCT GCTGCGGGAA   29760

CTGATGGACC TGTTCGCCGC CGGCGTGCTG CACCCGCTGC CCGTCGTCAC CCACGACGTG   29820

CGCCGGGCCG CGGACGCCCT GCGCACCATC AGCCAGGCCC GGCACACCGG AAAGCTCGTC   29880

CTGACCATGC CGCCCGCCTG GCACCCGTAC GGCACGGTCC TGGTCACCGG TGGCACCGGC   29940

GCCCTCGGCA GCCGCATCGC CCGCCACCTG GCGAGCCGGC ACGGCGTCCG CCGGCTGCTG   30000

ATCGCCGCCC GCCGGGGCCC GGACGGCGAG GGCGCCGCGG AGCTGGTCGC CGACCTCGCC   30060

GCCCTGGGCG CGTCGGCCAC CGTGGTCGCC TGCGACGTCT CCGACGCGGA CGCCGTCCGC   30120

GGACTGCTCG CCGGCATACC GGCCGATCAC CCGCTGACGG CGGTGGTGCA CAGCACCGGC   30180

GTCCTCGACG ACGGCGTGCT GCCCGGGCTC ACCCCCGAGC GGATGCGGCG CGTGCTGCGG   30240

CCCAAGGTGG AGGCCGCCGT CCACCTGGAC GAACTCACCC GCGACCTCGA CCTGTCGGCG   30300

TTCGTCCTCT TCTCCTCCAG CGCCGGTCTG CTGGGCAGCC CGGCCCAGGG CAACTACGCG   30360

GCGGCCAACG CCACCCTCGA CGCCCTCGCC GCCCGGCGCC GGTCCCTCGG CCTCCCGTCG   30420

GTGTCACTCG CCTGGGGTCT GTGGTCCGAC ACCAGCCGGA TGGCACACGC ACTGGACCAG   30480

GAGAGCCTCC AGCGGCGCTT CGCCCCGCAG GGCTTCCCGC CCTGTCCGC CACGCTGGGC    30540

GCCGCGCTGT TCGACGCCGC CCTGCGGGTC GACGAGGCCG TGCAGGTCCC CATGCGGTTC   30600

GACCCGGCCG CGCTGCGCGC CACCGGAAGC GTCCCCGCCC TGCTGTCGGA CCTCGTCGGG   30660
```

```
TCCGCCCCGG CGACCGGGTC CGCGGCCCCG GCGTCCGGCC CCCTTCCGGC TCCGGACGCC   30720

GGGACCGTCG GCGAGCCGCT CGCCGAGCGG TTGGCCGGAC TCTCCGCCGA GGAACGCCAC   30780

GACCGGCTGC TCGGCCTGGT CGGCGAACAC GTGGCCGCGG TACTGGGCCA CGGCTCCGCC   30840

GCCGAGGTCC GGCCCGACCG GCCGTTCCGC GAGGTCGGGT CGACTCGCT  CACGGCCGTG   30900

GAACTGCGCA ACCGGATGGC GGCGGTCACC GGGGTCAGGC TCCCCGCCAC CCTGGTCTTC   30960

GACCACCCCA CCCCCGCCGC GCTGTCCTCG CACCTCGACG GCCTGCTGGC CCCGGCACAG   31020

CCGGTCACCA CCACACCGCT GCTGTCCGAA CTGGACCGCA TCGAGGAGGC CCTGCCGCC   31080

CTCACCCCCG AGCACCTCGC GGAGCTCGCC CCCGCCCCCG ACGACCGGGC CGAGGTCGCC   31140

CTGCGCCTGG ACGCCCTGGC CGACCGCTGG CGCGCCCTGC ACGACGGCGC GCCCGGCGCC   31200

GACGACGACA TCACCGACGT GCTGAGCAGC GCCGACGACG ACGAGATCTT CGCGTTCATC   31260

GACGAGCGGT ACGGCACGTC GTGACCGCCG GCCCGGAGCC CCGCCCGTCA TCGAAAGGAA   31320

GCACCACCAT GGCGAACGAA GAGAAGCTGC GCGCCTACCT CAAGCGCGTG ACGGGTGAGC   31380

TGCACCGGGC CACCGAGCAG CTGCGTGCCC TGGACCGGCG GGCCCACGAG CCGATCGCGA   31440

TCGTCGGGGC GGCCTGCCGA CTCCCCGGCG GCGTCGAGAG TCCGGACGAC CTGTGGGAGC   31500

TGCTGCACGC CGGTGCCGAC GCGGTCGGCC CGGCCCCCGC CGACCGCGGC TGGGACGTGG   31560

AGGGAAGGTA CTCGCCCGAC CCCGACACGC CCGGCACCTC GTACTGCCGC GAGGGCGGCT   31620

TCGTGCAGGG GGCCGACCGG TTCGACCCCG CCCTCTTCGG CATCTCGCCC AACGAGGCGC   31680

TCACCATGGA CCCCCAGCAG CGGCTGCTGC TGGAGACCTC CTGGGAGGCG CTGGAGCGAG   31740

CCGGTCTGGA CCCCCAGTCC CTGGCGGGCA GCCGGACCGG CGTGTTCGCC GGGGCGTGGG   31800

AGAGCGGCTA CCAGAAGGGC GTCGAAGGGC TCGAAGCCGA TCTGGAGGCC CAACTCCTGG   31860

CCGGCATCGT CAGCTTCACC GCCGGCCGCG TCGCCTACGC CCTGGGCCTG GAGGGCCCGG   31920

CGCTGACGAT CGACACGGCC TGCTCCTCGT CGCTGGTGGC ACTGCACCTG GCGGTGCAGT   31980

CACTGCGCCG GGGCGAGTGC GACCTCGCAC TGGCGGGCGG CGCCACGGTC ATCGCCGACT   32040

TCGCGCTCTT CACCCAGTTC TCCCGGCAGC GCGGGCTCGC CCCCGACGGG CGGTGCAAGG   32100

CCTTCGGTGA GACGGCCGAC GGCTTCGGCC CCGCCGAGGG CGCGGGGATG CTGCTGGTCG   32160

AGCGGCTGTC GGACGCCCGC CGCAACGGGC ACCCGGTGCT GGCGGTGGTG CGGGGCAGTG   32220

CCGTCAACCA GGACGGTGCG AGCAATGGGC TGACGGCGCC GAGTGGTCCT GCGCAGCAGC   32280

GGGTGATCCG TGAGGCGCTG GCCGACGCGG GGCTGACGCC CGCCGACGTG GACGCGGTCG   32340

AGGCGCACGG CACCGGCACG CCGCTCGGCG ACCCCATCGA GGCCGGCGCG CTCATGGCGA   32400

CGTACGGGCA CGAACGGACG GGCGACCCGC TGTGGCTGGG TTCGCTGAAG TCGAACATCG   32460

GGCACACCCA GGCCGCCGCC GGCGTGGCCG GGGTGATCAA GATGGTGCTG GCGCTGCGCC   32520

ACGGTGAGCT GCCGCGCACC CTGCACGCGT CGACGGCGTC CTCCAGGATC GAATGGGACG   32580

CGGGCGCCGT GGAGTTGCTG GACGAGGCCA GGCCCTGGCC CCGGCGTGCC GAGGGGCCGC   32640

GCCGGGCGGG CATCTCCTCG TTCGGCATCA GCGGCACCAA CGCGCACCTC GTCATCGAGG   32700

AGGAGCCGCC CGCCCGGCCG GAGCCCGAGG AGGCCGCGCA GCCGCCCGCC CCGGCCACCA   32760

CCGTCCTCCC GCTGTCGGCC GCCGGCGCGC GATCCCTGCG CGAGCAGGCC CGCAGGCTCG   32820

CCGCGCACCT GGCCGGCCAC GAGGAGATCA CCGCCGCCGA CGCCGCCCGC TCCGCCGCCA   32880

CCACCCGTGC CGCGCTCTCG CACCGGGCCT CGGTCCTGGC CGACGACCGG CGGGCGCTGA   32940

TCGACAGGCT GACCGCGCTG GCGGAGGACA GGAAGGACCC CGGCGTCACC GTCGGCGAGG   33000

CGGGCAGCGG CCGGCCCCCC GTCTTCGTCT TCCCGGGACA GGGCTCCCAG TGGACGGGCA   33060
```

```
TGGGCGCCGA ACTCCTGGAC AGGGCACCGG TCTTCCGCGC CAAGGCCGAG GAGTGCGCGC    33120

GGGCCCTCGC GGCCCACCTC GACTGGTCGG TGCTCGACGT CCTGCGCGAC GCGCCCGGCG    33180

CCCCGCCGAT CGACCGCGCG GACGTCGTCC AGCCGACCCT GTTCACCATG ATGGTCTCCC    33240

TCGCGGCGCT GTGGGAGTCC CACGGTGTAC GGCCCGCCGC CGTGGTCGGC CACTCCCAAG    33300

GCGAGATCGC CGCCGCCCAC GCGGCCGGTG CCCTGTCCCT CGACGACGCG GCCCGCGTGA    33360

TCGCCGAGCG CAGCAGGCTC TGGAAGCGGC TGGCCGGAAA CGGCGGCATG CTCTCCGTGA    33420

TGGCCCCGGC CGACCGGGTC CGCGAACTGA TGGAGCCCTG GCGGAGCGG ATGTCCGTGG     33480

CCGCCGTCAA CGGCCCCGCC TCGGTCACCG TGGCCGGTGA CGCGCGGGCG CTGGAGGAGT    33540

TCGGCGGCCG GCTCTCCGCC GCCGGGGTGC TGCGCTGGCC CCTCGCCGGC GTCGACTTCG    33600

CCGGACACTC ACCCCAGGTG GAGCAGTTCC GCGCCGAGCT CCTCGACACG CTGGGCACCG    33660

TCCGCCCGAC CGCCGCCCGG CTGCCCTTCT TCTCCACCGT GACCGCCGCG GCGCACGAGC    33720

CCGAAGGCCT GGACGCCGCG TACTGGTACC GGAACATGCG CGAACCCGTG GAGTTCGCGT    33780

CCACCCTGCG GACGCTGCTG CGCGAGGGCC ACCGCACCTT CGTCGAGATG GGCCCGCACC    33840

CCCTGCTGGG CGCCGCGATC GACGAGGTCG CCGAGGCCGA GGGCGTGCAC GCCACCGCCC    33900

TCGCCACCCT CCACCGCGGC TCCGGCGGCC TGGACCGGTT CCGCTCCTCG GTGGGCGCCG    33960

CGTTCGCCCA CGGAGTACGG GTCGACTGGG ACGCCCTCTT CGAGGGCTCC GGCGCCCGCC    34020

GGGTCCCGCT GCCCACCTAC GCCTTCAGCC GGGACCGGTA CTGGCTGCCC ACCGCCATCG    34080

GCCGGCGCGC CGTCGAGGCG GCCCCCGTCG ACGCGTCCGC CCCCGGGCGC TACCGCGTCA    34140

CCTGGACACC CGTGGCATCC GACGACTCCG GCCGGCCCTC CGGGCGCTGG CTGCTGGTGC    34200

AGACCCCCGG CACCGCGCCG GACGAGGCGG ACACCGCGGC GTCGGCCCTC GGTGCGGCCG    34260

GGGTGGTCGT GGAGCGCTGC CTGCTGGATC CCACCGAGGC CGCGCGCGTC ACGCTCACCG    34320

AGCGACTGGC CGAACTGGAC GCGCAGCCGG AGGGCCTGGC CGGCGTGCTG GTGCTGCCCG    34380

GCCGTCCGCA GAGCACCGCA CCGGCCGACG CCTCCCCGCT CGACCCGGGG ACGGCCGCCG    34440

TCCTGCTCGT GGTCCAGGCC GTGCCGGACG CCGCTCCGAA GGCCCGGATC TGGGTGGTGA    34500

CGCGGGGTGC GGTGGCGGTG GGGTCGGGTG AGGTGCCGTG TGCGGTGGGT GCGCGGGTGT    34560

GGGGTCTGGG GCGGGTGGCT GCGTTGGAGG TGCCGGTGCA GTGGGGTGGG TTGGTGGATG    34620

TGGCGGTGGG GGCGGGTGTG CGTGAGTGGC GTCGTGTGGT GGGTGTGGTT GCGGGGGTG     34680

GTGAGGATCA GGTGGCGGTG CGTGGTGGGG GTGTGTTCGG TCGTCGTCTG GTGGGTGTGG    34740

GGGTGCGGGG TGGTTCGGGG GTGTGGCGTG CGCGGGGGTG TGTGGTGGTG ACGGGTGGGT    34800

TGGGTGGTGT GGGGGGTCAT GTGGCGCGGT GGTTGGCGCG TTCGGGTGCG GAGCATGTGG    34860

TGTTGGCGGG GCGTCGGGGT GGTGGGGTTG TGGGGCGGT GGAGTTGGAG CGGGAGTTGG     34920

TGGGGTTGGG GGCGAAGGTG ACGTTCGTTT CGTGTGATGT GGGGGATCGG GCGTCGATGG    34980

TGGGGTTGTT GGGTGTGGTG GAGGGGTTGG GGGTGCCGTT GCGTGGTGTG TTTCATGCGG    35040

CGGGGGTGGC TCAGGTGTCG GGGTTGGGTG AGGTGTCGTT GGCGGAGGCG GGTGGTGTGT    35100

TGGGGGGTAA GGCGGTGGGG GCTGAGTTGT TGGACGAGTT GACGGCGGGT GTGGAGCTGG    35160

ATGCGTTCGT GTTGTTCTCG TCGGGTGCTG GGGTGTGGGG GAGTGGGGGG CAGTCGGTGT    35220

ATGCGGCGGC CAATGCGCAT CTGGATGCGT TGGCGGAGCC TCGTCGTGCG CAGGGGCGTC    35280

CCGCGACCTC CGTCGCCTGG GGCCTGTGGG GCGGCGAGGG CATGGGAGCG GACGAAGGCG    35340

TCACGGAGTT CTACGCCGAG CGCGGCCTCG CCCCCATGCG GCCCGAGTCG GGCATCGAGG    35400

CACTGCACAC GGCACTGAAC GAGGGCGACA CCTGCGTCAC GGTCGCCGAC ATCGACTGGG    35460
```

```
AACACTTCGT CACCGGGTTC ACCGCCTACC GGCCCAGCCC GCTGATCTCC GACATCCCCC  35520

AGGTCCGCGC GTTGCGCACG CCCGAACCCA CCGTGGACGC CTCGGACGGA CTGCGCCGGC  35580

GCGTCGACGC CGCCCTCACC CCGCGCGAGC GCACCAAGGT CCTGGTCGAC CTGGTCCGCA  35640

CGGTGGCGGC GGAGGTCCTC GGTCACGACG GGATCGGCGG CATCGGCCAC GACGTGGCCT  35700

TCCGGGACCT CGGCTTCGAC TCGCTGGCCG CGGTGCGGAT GCGCGGCCGG CTGGCCGAGG  35760

CGACCGGACT CGTACTGCCC GCGACGGTCA TCTTCGACCA CCCCACCGTG GACCGGCTCG  35820

GCGGCGCGCT GCTGGAGCGG CTGTCCGCGG ACGAACCCGC GCCCGGCGGG GCGCCGGAGC  35880

CCGCCGGGGG GAGGCCCGCG ACCCCACCGC CCGCACCGGA GCCGGCCGTC CACGACGCCG  35940

ACATCGACGA ACTCGACGCG GACGCCCTGA TCCGGCTGGC CACGGGAACC GCCGGACCGG  36000

CCGACGGCAC GCCGGCCGAC GGCGGGCCCG ACGCGGCGGC GACCGCCCCC GACGGAGCAC  36060

CGGAGCAGTA GCGCGCCCTC ACCGGCGCGC CGACCGGCGG AGCGCCGTAC CGCCGACGCC  36120

CCCCACAGCC AGCGAGCAGA CGAGGAAGCC GAAGATGTCA CCGTCCATGG ACGAAGTGCT  36180

GGGTGCGCTG CGCACCTCCG TCAAGGAGAC CGAGCGGCTG CGCCGGCACA ACCGGGAGCT  36240

CCTGGCCGGC GCGCACGAGC CGGTCGCCAT CGTGGGCATG GCCTGCCGCT ACCCCGGTGG  36300

CGTGAGCACC CCGGACGACC TGTGGGAGCT CGCCGCGGAC GGCGTCGACG CGATCACCCC  36360

CTTCCCGGCC GACCGGGGCT GGGACGAGGA CGCCGTCTAC TCGCCCGACC CCGACACCCC  36420

CGGCACCACC TACTGCCGTG AGGGCGGCTT CCTCACCGGC GCCGGGGACT TCGACGCGGC  36480

CTTCTTCGGC ATCTCGCCGA ACGAGGCGCT GGTGATGGAC CCGCAGCAGC GGCTGTTGCT  36540

GGAGACGTCG TGGGAGACGT TGGAGCGGGC CGGCATCGTC CCCGCGTCGC TGCGCGGCAG  36600

CCGTACCGGT GTCTTCGTCG GAGCCGCGCA CACGGGATAC GTCACCGACA CCGCGCGAGC  36660

GCCCGAGGGC ACCGAGGGCT ATCTGCTGAC GGGCAACGCC GATGCCGTCA TGTCCGGCCG  36720

GATCGCCTAC TCCCTGGGTC TGGAGGGGCC GGCGCTGACG ATCGGGACGG CCTGCTCGTC  36780

GTCGTTGGTG GCGTTGCATC TGGCGGTGCA GTCGTTGCGG CGGGGCGAGT GCGACCTGGC  36840

GTTGGCCGGC GGCGTCGCGG TCATGCCCGA CCCGACGGTG TTCGTGGAGT CTCGCGGCA  36900

GCGGGGGCTG GCGGTGGACG GCGGTGCAA GGCGTTCGCG GAGGGTGCGG ACGGGACGGC  36960

GTGGGCGGAG GGAGTGGGTG TGCTGCTGGT GGAGCGGCTT TCCGACGCGC GCCGCAATGG  37020

CCATCGGGTG CTGGCGGTGG TGCGGGGCAG TGCGGTCAAT CAGGACGGGG CGAGCAATGG  37080

GCTGACGGCG CCGAGTGGTC CTGCGCAGCA GCGGGTGATC CGTGAGGCGC TGGCTGATGC  37140

GGGGCTGACG CCCGCCGACG TGGATGTGGT GGAGGCGCAC GGTACGGGGA CGGCGTTGGG  37200

TGATCCGATC GAGGCGGGTG CGTTGCTGGC CACGTACGGG CGGGAGCGGG TCGGTGATCC  37260

TTTGTGGTTG GGGTCGTTGA AGTCGAACAT CGGGCATGCG CAGGCGGCTG CGGGTGTGGG  37320

TGGTGTGATC AAGGTGGTGC AGGCGATGCG GCATGGGTCG TTGCCGCGGA CGCTGCATGT  37380

GGATGCGCCG TCGTCGAAGG TGGAGTGGGC TTCGGGTGCG GTGGAGCTGC TGACCGAGGG  37440

CCGGTCGTGG CCGCGGCGGG TGGAGCGGGT GCGGCGGGCC GCGGTGTCGG CGTTCGGGGT  37500

GAGCGGGACC AACGCCCATG TGGTCCTGGA GGAAGCACCG GTCGAGGCCG GGAGCGAGCA  37560

CGGGGACGGC CCCGGACCCG ACCGGCCCGA CGCCGTGACG GGTCCGCTCC CCTGGGTGCT  37620

CTCGGCACGC TCGCGGAGG CGCTGCGCGG CCAGGCCGGA CGACTCGCCG CTCTCGCCCG  37680

CCAGGGGCGC ACGGAGGGCA CCGGCGGCGG CAGCGGACTC GTCGTCCCCG CGGCCGACAT  37740

CGGATACTCC CTGCCACCA CCAGGGAGAC CCTGGAGCAC CGGGCGGTGG CGCTGGTGCA  37800

GGAGAACCGG ACGGCCGGGG AGGACCTCGC CGCGCTGGCC GCCGGCCGCA CACCGGAGAG  37860
```

```
CGTGGTCACG GGTGTCGCGC GACGTGGCCG CGGGATCGCC TTCCTCTGCT CGGGGCAGGG    37920

CGCCCAGCGG CTCGGCGCCG GTCGGGAGCT CCGCGGCAGG TTCCCCGTCT TCGCCGACGC    37980

CCTCGACGAG ATCGCGGCGG AGTTCGACGC CCACCTCGAA CGCCCTCTCC TGTCGGTGAT    38040

GTTCGCCGAG CCCGCCACGC CGGACGCCGC ACTCCTCGAC CGCACCGACT ACACCCAGCC    38100

GGCCCTCTTC GCGGTGGAGA CCGCGCTCTT CCGGCTCCTG GAGAGCTGGG GCCTGGTCCC    38160

GGACGTCCTC GTGGGCCACT CGATCGGCGG TCTGGTGGCG GCTCACGTGG CGGGCGTCTT    38220

CTCTGCGGCC GACGCGGCCC GGCTGGTCTC CGCACGCGGC CGGCTCATGC GGGCCCTGCC    38280

CGAGGGCGGC GCGATGGCGG CCGTGCAGGC CACCGAGCGG GAGGCCGCCG CGCTGGAGCC    38340

CGTCGCCGCC GGCGGCGCGG TGGTCGCCGC GGTCAACGGC CCGCAGGCCC TCGTGCTCTC    38400

CGGGGACGAG GCGGCCGTAC TGGCGGCGGC CGGTGAACTG GCCGCCCGCG GACGCCGCAC    38460

CAAGCGCCTG AGGGTGAGCC ACGCCTTCCA CTCACCCCGT ATGGACGCCA TGCTCGCCGA    38520

CTTCCGCGCG GTGGCGGACA CGGTCGACTA CCACGCCCCC CGGCTGCCGG TCGTCTCCGA    38580

AGTGACCGGC GACCTCGCCG ACGCCGCCCA GCTGACCGAC CCCGGCTACT GGACCCGCCA    38640

GGTGCGGCAG CCGGTGCGCT TCGCCGACGC CGTGCGCACC GCGAGCGCCC GGGACGCCGC    38700

GACCTTCATC GAGCTCGGGC CCGACGCCGT CCTGTGCGGC ATGGCGGAGG AGTCCCTGGC    38760

CGCGGAGGCC GACGTCGTGT TCGCCCCGGC ACTGCGCCGC GGGCGCCCGG AGGGCGACAC    38820

CGTGCTCCGG GCCGCCGCGA GCGCGTACGT CCGCGGCGCG GGCCTCGACT GGGCCGCGCT    38880

CTACGGCGGC ACGGGAGCCC GCCGCACCGA CCTGCCCACC TACGCCTTCC AGCACAGCCG    38940

CTACTGGCTC GCCCCCGCCT CGGCCGCGGT CGCCCCGCG ACGGCCGCCC CCTCCGTCCG    39000

ATCCGTGCCG GAAGCCGAGC AGGACGGGGC GCTGTGGGCC GCCGTGCACG CCGGTGACGT    39060

CGCCTCGGCC GCGGCGCGAC TGGGCGCCGA CGACGCCGGT ATCGAACACG AACTGCGCGC    39120

GGTCCTGCCG CACCTGGCCG CCTGGCACGA CCGCGACCGC GCGACCGCGC GGACCGCGGG    39180

CCTGCACTAC CGCGTCACCT GGCAGGCGAT CGAGGCAGAC GCTGTCAGGT TCAGCCCCTC    39240

GGATCGCTGG CTGATGGTCG AGCATGGGCA GCACACGGAA TGCGCGGACG CCGCGGAACG    39300

GGCGCTGCGC GCGGCCGGCG CGGAGGTCAC CCGCCTGGTG TGGCCGCTGG AGCAGCACAC    39360

CGGATCACCG CGGACGGAGA CCCCGGACCG CGGCACCCTG GCGGCCCGGC TGGCCGAGCT    39420

CGCACGGAGC CCGGAGGGCC TGGCCGGCGT GCTGCTGCTC CCCGACTCGG GCGGTGCCGC    39480

GGTCGCCGGG CACCCCGGGC TGGACCAGGG AACGGCGGCG GTGCTGCTGA CGATCCAGGC    39540

ACTGACCGAC GCCGCGGTGC GGGCACCGCT GTGGGTGGTG ACGCGGGGTG CGGTGGCGGT    39600

GGGGTCGGGT GAGGTGCCGT GTGCGGTGGG TGCGCGGGTG TGGGGTCTGG GGCGGGTGGC    39660

TGCGTTGGAG GTGCCGGTGC AGTGGGGTGG GTTGGTGGAT GTGGCGGTGG GGGCGGGTGT    39720

GCGTGAGTGG CGTCGTGTGG TGGGTGTGGT TGCGGGGGGT GGTGAGGATC AGGTGGCGGT    39780

GCGTGGTGGG GGTGTGTTCG GTCGTCGTCT GGTGGGTGTG GGGGTGCGGG GTGGTTCGGG    39840

GGTGTGGCGT GCGCGGGGGT GTGTGGTGGT GACGGGTGGG TTGGGTGGTG TGGGGGGTCA    39900

TGTGGCGCGG TGGTTGGCGC GTTCGGGTGC GGAGCATGTG GTGTTGGCGG GGCGTCGGGG    39960

TGGTGGGGTT GTGGGGCGG TGGAGTTGGA GCGGGAGTTG GTGGGGTTGG GGGCGAAGGT    40020

GACGTTCGTT TCGTGTGATG TGGGGGATCG GGCGTCGGTG GTGGGGTTGT TGGGTGTGGT    40080

GGAGGGGTTG GGGGTGCCGT TGCGTGGTGT GTTTCATGCG GCGGGGGTGG CTCAGGTGTC    40140

GGGGTTGGGT GAGGTGTCGT TGGCGGAGGC GGGTGGTGTG TTGGGGGGTA AGGCGGTGGG    40200

GGCTGAGTTG TTGGACGAGT TGACGGCGGG TGTGGAGCTG GATGCGTTCG TGTTGTTCTC    40260
```

```
GTCGGGTGCT GGGGTGTGGG GGAGTGGGGG GCAGTCGGTG TATGCGGCGG CCAATGCGCA   40320

TCTGGATGCG TTGGCGGAGC GTCGTCGTGC GCAGGGGCGT CCCGCGACCT CCGTCGCCTG   40380

GGGCCCGTGG GACGGCGACG GCATGGGCGA GATGGCGCCC GAGGGCTACT TCGCCCGCCA   40440

CGGCGTGGCC CCGCTCCACC CCGAGACGGC GCTCACCGCC CTGCACCAGG CCATCGACGG   40500

CGGCGAAGCC ACGGTCACCG TGGCGGACAT CGACTGGGAA CGGTTCGCCC CCGGCTTCAC   40560

CGCCTTCCGT CCCAGCCCCC TGATCGCCGG CATCCCCGCG GCCCGTACGG CGCCCGCCGC   40620

CGGCCGGCCC GCCGAGGACA CCCCCACCGC CCCCGGCCTC CTGCGGGCGC GGCCCGAGGA   40680

CCGGCCGCGG CTCGCCCTGG ACCTGGTGCT CCGCCACGTC GCGGCGGTCC TCGGCCACTC   40740

CGAGGACGCC CGGGTCGACG CCCGGGCCCC CTTCCGGGAC CTCGGCTTCG ACTCGCTCGC   40800

CGCGGTGCGG CTGCGCCGCC GGCTGGCCGA GGACACCGGG CTCGACCTGC CCGGCACCCT   40860

CGTCTTCGAC CACGAGGACC CCACCGCGCT GGCCCACCAC CTGGCCGGCC TCGCCGACGC   40920

GGGGACCCCC GGCCCCCAGG AGGGCACGGC TCGGCCGAG AGCGGGCTGT TCGCCTCCTT   40980

CCGCGCCGCC GTCGAACAGC GCAGGTCGAG CGAGGTCGTG GAGCTGATGG CCGACCTGGC   41040

GGCGTTCCGG CCCGCCTACT CCCGGCAGCA CCCCGGCTCC GGCCGCCCCG CGCCCGTACC   41100

CCTCGCGACC GGACCGGCGA CGCGTCCCAC GCTGTACTGC TGCGCCGGCA CCGCGGTCGG   41160

CTCCGGGCCC GCCGAGTACG TCCCGTTCGC CGAAGGACTG CGCGGCGTCC GGGAGACGGT   41220

CGCCCTTCCC CTGTCCGGCT TCGGCGACCC CGCGGAACCG ATGCCCGCAT CGCTCGACGC   41280

GCTGATCGAG GTCCAGGCCG ACGTCCTCCT GGAGCACACC GCGGGCAAGC CCTTCGCCCT   41340

CGCCGGCCAC TCCGCCGGCG CGAACATCGC CCACGCCCTG GCCGCCCGGC TGGAGGAACG   41400

CGGCTCGGGC CCCGCAGCCG TCGTACTGAT GGACGTCTAC CGTCCCGAGG ACCCCGGTGC   41460

GATGGGCGAG TGGCGCGACG ACCTGCTCAG CTGGGCGCTC GAACGCAGCA CGGTGCCCCT   41520

GGAGGACCAC CGGCTCACCG CCATGGCCGG CTATCAGCGG CTGGTGCTCG GAACCCGGCT   41580

CACCGCCCTC GAAGCCCCCG TCCTGCTGGC CCGGGCGTCC GAACCCCTGT GCGCGTGGCC   41640

GCCCGCGGGC GGGGCGCGGG GCGACTGGCG GTCCCAGGTC CCGTTCGCAC GGACCGTCGC   41700

CGACGTGCCC GGCAACCACT TCACCATGCT CACCGAACAC GCCCGGCACA CCGCGTCCCT   41760

GGTGCACGAA TGGCTGGACA GCCTCCCGCA CCAGCCCGGT CCCGCCCCGC TCACCGGAGG   41820

GAAACACTGA TGTACGCCGA CGACATCGCG GCCGTCTACG ACCTGGTCCA CGAGGGGAAG   41880

GGGAAGGACT ACCGGCAGGA GGCCGAGGAG ATCGCCGCAC TCGTGCGCGT CCACCGGCCG   41940

GGCGCCCGGA CCCTGCTCGA CGTGGCCTGC GGCACCGGCC AGCACCTGCA CCACCTGGAC   42000

GGCCTCTTCG ACCACGTCGA GGGCCTGGAA CTCTCCGCCG ACATGCTGGC CCTCGCGACC   42060

GGCCGGAACC CCGGTGTCAC CTTCCACCAA GGGGACATGC GCTCGTTCTC CCTGGGACGC   42120

CGGTTCGACG CGGTGACCTG CATGTTCAGC TCCATAGGCC ACCTGCGGAC CACCGACGAA   42180

CTCGACAGCA CGCTGCGGGC CTTCACCGAC CACCTCGAAC CGTCCGGCGT CATCGTCGTC   42240

GAACCCTGGT GGTTCCCCGA GTCCTTCACC CCCGGTTACG TCGGCGCCAG CATCACGGAG   42300

GCGGGCGAGC GCACCGTCTG CCGGGTCTCG CACTCCGTAC GGGAGGGGAA CGCCACCCGC   42360

ATCGAGGTGC ACTACCTCCT CGCCGGACCC GGCGGCGTCC GTCACCTGAC CGAGGACCAC   42420

ACCATCACCC TGTTCCCGCG CGCCGACTAC GAGGCGGCCT TCGAGCGCGC CGGCTGCGAC   42480

GTGGTCTACC AGGAAGGCGG CCCGTCCGGT CGCGGGCTGT TCATCGGCAC CCGCCGCTGA   42540

CCCGGTGCCG ACGCGGACCG CCGCGGCCCG GAGGCGGGTT GCCCCGACCC ACCCGGCACA   42600

CCCGGGTCCC CCGATCGTGC GAGCGCCCCC ATCGACCCGA GAAGAAAGGC AGGGCAGCCA   42660
```

```
TGCCCACCCT TGCCACGGAA ACGGCCCCCG CGAGCACGAG CACGAGCGCG GGCACGAGCA    42720

CGGGCGTCCG TGCGCTCGGC CGTCGGCTCC AGCTGACCCG GGCCGCACAC TGGTGCGCCG    42780

GCAACCAGGG CGACCCGTAC GCGCTGATCC TGCGCGCCGT CGCCGACCCC GAGCCGTTCG    42840

AACGGGAGAT CCGGGCCCGC GGACCGTGGT TCCGCAGCGA ACAGCTGGAC GCCTGGGTGA    42900

CCGCGGACCC CGAGGTGGCG GCGGCCGTCC TGGCCGACCC GCGCTTCGGC ACGCTGGACC    42960

GGGCCGGACG CCGCCCGGAC GAGGAACTGC TGCCCCTCGC CGAGGCGTTC CCCCACCACG    43020

AACGCGCGGA GCTCGTACGC CTGCGGGCGC TGGCCGCCCC GGTGCTCAGC CGGTACGCCC    43080

CGGCCCAGGC GCCCTGCGCG GCGCGCACCA CCGCCCGCAG AGTGCTCGGC CGCCTGCTGC    43140

CCACCGGTGA CGCCGGGTTC GACCTTGTCG GCGAGGTCGC CCGGCCCTAC GCCGTCGAGC    43200

TGATGCTCAG GCTCCTCGGA GTGCCGGGCC GCGACCGCGC CACCGCCGCG CGGGCACTCG    43260

CCGCCTGCGG CCCCCAGCTC GACGCCCGGA TGGCCCCGCA ACTGCTGACC GTGGCCCGGG    43320

AGTCCGCCGA CGCCGTCCGC ACACTGGCCG ACCTGGTCCC CGAGCTCGTC GCGGAGAAGT    43380

CCCGGGGCCT CGGGAACGCC GAGCCCCGGC CCGACGACGT GCTCGCCCTC CTCCTGCACG    43440

ACGGCGTCGC CCCCGGCGAC GTCGAGCGCA TCGCGCTGCT CCTCGCGGTC GGCGCACCCG    43500

AACCCGTCGT CACCGCCGTC GCGCACACGG TCCACCGGCT GCTCGGCCGG CCGGGGGAGT    43560

GGGAGAGGGC CCGCCGGACG CCGGCCGCGG CGAACGCCGT CGACCAGGTG CTGCGCGAGC    43620

GCCCCCCGGC CCGGCTGGAG AACCGGGTCG CGCACACCGG CCTCGAACTC GGCGGCCGCC    43680

GGATCACCGC CGACGAGCAC GTCGTGGTGC TGGCCGCCGC CGGACGGGAG ATCCCCGGGC    43740

CGGAGCCGCT CGGGGGCGCC GACGGACCGC ACCTGGCGCT CGCCCTCCCG CTGATCCGCC    43800

TGGCCGCCAC CACCGCGGTC CAGGTCACGG CCGGCCGCCT GCCGGCCTG CGGGCCGAGG     43860

GACCGCCCCT GACCCGGCCG CGGTCACCGG TCCTGGGCGC CTGCGCCCGC CTCCGGGTCC    43920

ACCCGGGATG ACCCCGCCGT CCGTACGCCC CCTCCCAGAC CGGAGCCGCT GTGCGCGTCC    43980

TGCTGACATC CCTCGCCCAC AACACCCACT ACTACAGTCT GGTGCCCCTC GCCTGGGCGC    44040

TGCGCGCCGC CGGGCACGAG GTACGGGTGG CGAGCCCGCC CTCCCTCACC GACGTCATCA    44100

CCTCCACCGG TCTGACCGCC GTACCGGTGG GCGACGACCG ACCGGCCGCG GAGCTGCTCG    44160

CCGAGATGGG CAGAGACCTC GTCCCCTACC AGAGGGGCTT CGAGTTCGGT GAGGTGGAGA    44220

GCGAGGAGGA GACCACCTGG GAGTACCTGC TCGGCCAGCA GAGCATGATG GCCGCCCTGT    44280

GCTTCGCCCC GTTCAACGGC GCCGCCACGA TGGACGAGAT CGTCGACTTC GCCCGTGGCT    44340

GGCGGCCCGA CCTGGTCGTG TGGGAACCCT GGACCTA                             44377
```

(2) INFORMATION FOR SEQ ID NO:2:

(i) SEQUENCE CHARACTERISTICS:
        (A) LENGTH: 4550 amino acids
        (B) TYPE: amino acid
        (D) TOPOLOGY: unknown (ii) MOLECULE TYPE: peptide (xi) SEQUENCE DESCRIPTION: SEQ ID NO:2:

```
Met Ser Gly Glu Leu Ala Ile Ser Arg Ser Asp Asp Arg Ser Asp Ala
1               5                   10                  15

Val Ala Val Val Gly Met Ala Cys Arg Phe Pro Gly Ala Pro Gly Ile
                20                  25                  30

Ala Glu Phe Trp Lys Leu Leu Thr Asp Gly Arg Asp Ala Ile Gly Arg
            35                  40                  45

Asp Ala Asp Gly Arg Arg Arg Gly Met Ile Glu Ala Pro Gly Asp Phe
```

```
                    50                      55                      60
Asp Ala Ala Phe Phe Gly Met Ser Pro Arg Glu Ala Glu Thr Asp
 65                      70                      75                      80

Pro Gln Gln Arg Leu Met Leu Glu Leu Gly Trp Glu Ala Leu Glu Asp
                         85                      90                      95

Ala Gly Ile Val Pro Gly Ser Leu Arg Gly Glu Ala Val Gly Val Phe
                    100                     105                     110

Val Gly Ala Met His Asp Asp Tyr Ala Thr Leu Leu His Arg Ala Gly
                    115                     120                     125

Ala Pro Val Gly Pro His Thr Ala Thr Gly Leu Gln Arg Ala Met Leu
130                     135                     140

Ala Asn Arg Leu Ser Tyr Val Leu Gly Thr Arg Gly Pro Ser Leu Ala
145                     150                     155                     160

Val Asp Thr Ala Gln Ser Ser Leu Val Ala Val Ala Leu Ala Val
                    165                     170                     175

Glu Ser Leu Arg Ala Gly Thr Ser Arg Val Ala Val Ala Gly Gly Val
                    180                     185                     190

Asn Leu Val Leu Ala Asp Glu Gly Thr Ala Ala Met Glu Arg Leu Gly
                    195                     200                     205

Ala Leu Ser Pro Asp Gly Arg Cys His Thr Phe Asp Ala Arg Ala Asn
210                     215                     220

Gly Tyr Val Arg Gly Glu Gly Gly Ala Ala Val Val Leu Lys Pro Leu
225                     230                     235                     240

Ala Asp Ala Leu Ala Asp Gly Asp Pro Val Tyr Cys Val Val Arg Gly
                    245                     250                     255

Val Ala Val Gly Asn Asp Gly Gly Pro Gly Leu Thr Ala Pro Asp
                    260                     265                     270

Arg Glu Gly Gln Glu Ala Val Leu Arg Ala Ala Cys Ala Gln Ala Arg
                    275                     280                     285

Val Asp Pro Ala Glu Val Arg Phe Val Glu Leu His Gly Thr Gly Thr
290                     295                     300

Pro Val Gly Asp Pro Val Glu Ala His Ala Leu Gly Ala Val His Gly
305                     310                     315                     320

Ser Gly Arg Pro Ala Asp Asp Pro Leu Leu Val Gly Ser Val Lys Thr
                    325                     330                     335

Asn Ile Gly His Leu Glu Gly Ala Ala Gly Ile Ala Gly Leu Val Lys
                    340                     345                     350

Ala Ala Leu Cys Leu Arg Glu Arg Thr Leu Pro Gly Ser Leu Asn Phe
                    355                     360                     365

Ala Thr Pro Ser Pro Ala Ile Pro Leu Asp Gln Leu Arg Leu Lys Val
                    370                     375                     380

Gln Thr Ala Ala Ala Glu Leu Pro Leu Ala Pro Gly Ala Pro Leu
385                     390                     395                     400

Leu Ala Gly Val Ser Ser Phe Gly Ile Gly Gly Thr Asn Cys His Val
                    405                     410                     415

Val Leu Glu His Leu Pro Ser Arg Pro Thr Pro Ala Val Ser Val Ala
                    420                     425                     430

Ala Ser Leu Pro Asp Val Pro Pro Leu Leu Ser Ala Arg Ser Glu
                    435                     440                     445

Gly Ala Leu Arg Ala Gln Ala Val Arg Leu Gly Glu Tyr Val Glu Arg
                    450                     455                     460

Val Gly Ala Asp Pro Arg Asp Val Ala Tyr Ser Leu Ala Ser Thr Arg
465                     470                     475                     480
```

-continued

```
Thr Leu Phe Glu His Arg Ala Val Val Pro Cys Gly Gly Arg Gly Glu
            485                 490                 495

Leu Val Ala Ala Leu Gly Gly Phe Ala Ala Gly Arg Val Ser Gly Gly
        500                 505                 510

Val Arg Ser Gly Arg Ala Val Pro Gly Gly Val Gly Val Leu Phe Thr
    515                 520                 525

Gly Gln Gly Ala Gln Trp Val Gly Met Gly Arg Gly Leu Tyr Ala Gly
530                 535                 540

Gly Gly Val Phe Ala Glu Val Leu Asp Glu Val Leu Ser Met Val Gly
545                 550                 555                 560

Glu Val Asp Gly Arg Ser Leu Arg Asp Val Met Phe Gly Asp Val Asp
                565                 570                 575

Val Asp Ala Gly Ala Gly Ala Asp Ala Gly Ala Gly Ala Gly Ala Gly
            580                 585                 590

Val Gly Ser Gly Ser Gly Ser Val Gly Gly Leu Leu Gly Arg Thr Glu
        595                 600                 605

Phe Ala Gln Pro Ala Leu Phe Ala Leu Glu Val Ala Leu Phe Arg Ala
    610                 615                 620

Leu Glu Ala Arg Gly Val Glu Val Ser Val Val Leu Gly His Ser Val
625                 630                 635                 640

Gly Glu Val Ala Ala Ala Tyr Val Ala Gly Val Leu Ser Leu Gly Asp
                645                 650                 655

Ala Val Arg Leu Val Val Ala Arg Gly Gly Leu Met Gly Gly Leu Pro
            660                 665                 670

Val Gly Gly Gly Met Trp Ser Val Gly Ala Ser Glu Ser Val Val Arg
        675                 680                 685

Gly Val Val Glu Gly Leu Gly Glu Trp Val Ser Val Ala Ala Val Asn
    690                 695                 700

Gly Pro Arg Ser Val Val Leu Ser Gly Asp Val Gly Val Leu Glu Ser
705                 710                 715                 720

Val Val Ala Ser Leu Met Gly Asp Gly Val Glu Cys Arg Arg Leu Asp
                725                 730                 735

Val Ser His Gly Phe His Ser Val Leu Met Glu Pro Val Leu Gly Glu
            740                 745                 750

Phe Arg Gly Val Val Glu Ser Leu Glu Phe Gly Arg Val Arg Pro Gly
        755                 760                 765

Val Val Val Val Ser Gly Val Ser Gly Gly Val Val Gly Ser Gly Glu
    770                 775                 780

Leu Gly Asp Pro Gly Tyr Trp Val Arg His Ala Arg Glu Ala Val Arg
785                 790                 795                 800

Phe Ala Asp Gly Val Gly Val Val Arg Gly Leu Gly Val Gly Thr Leu
                805                 810                 815

Val Glu Val Gly Pro His Gly Val Leu Thr Gly Met Ala Gly Glu Cys
            820                 825                 830

Leu Gly Ala Gly Asp Asp Val Val Val Pro Ala Met Arg Arg Gly
        835                 840                 845

Arg Ala Glu Arg Glu Val Phe Glu Ala Ala Leu Ala Thr Val Phe Thr
    850                 855                 860

Arg Asp Ala Gly Leu Asp Ala Thr Ala Leu His Thr Gly Ser Thr Gly
865                 870                 875                 880

Arg Arg Ile Asp Leu Pro Thr Tyr Pro Phe Gln Arg Arg Thr His Trp
                885                 890                 895

Ser Pro Ala Leu Ser Arg Pro Val Thr Ala Asp Ala Gly Ala Gly Val
            900                 905                 910
```

```
Thr Ala Thr Asp Ala Val Gly His Ser Val Ser Pro Asp Pro Glu Ser
        915                 920                 925

Thr Glu Gly Thr Ser His Arg Asp Thr Asp Glu Ala Asp Ser Ala
    930                 935                 940

Ser Pro Glu Pro Met Ser Pro Glu Asp Ala Val Arg Leu Val Arg Glu
945                 950                 955                 960

Ser Thr Ala Ala Val Leu Gly His Asp Pro Gly Glu Val Ala Leu
        965                 970                 975

Asp Arg Thr Phe Thr Ser Gln Gly Met Asp Ser Val Thr Ala Val Glu
        980                 985                 990

Leu Cys Asp Leu Leu Lys Gly Ala Ser Gly Leu Pro Leu Ala Ala Thr
        995                 1000                1005

Leu Val Tyr Asp Leu Pro Thr Pro Arg Ala Val Ala Glu His Ile Val
        1010                1015                1020

Glu Ala Ala Gly Gly Pro Lys Asp Ser Val Ala Gly Pro Gly Val
1025                1030                1035                1040

Leu Ser Ser Ala Ala Val Gly Val Ser Asp Ala Arg Gly Gly Ser Arg
        1045                1050                1055

Asp Asp Asp Asp Pro Ile Ala Ile Val Gly Val Gly Cys Arg Leu Pro
        1060                1065                1070

Gly Gly Val Asp Ser Arg Ala Ala Leu Trp Glu Leu Leu Glu Ser Gly
        1075                1080                1085

Ala Asp Ala Ile Ser Ser Phe Pro Thr Asp Arg Gly Trp Asp Leu Asp
        1090                1095                1100

Gly Leu Tyr Asp Pro Glu Pro Gly Thr Pro Gly Lys Thr Tyr Val Arg
1105                1110                1115                1120

Glu Gly Gly Phe Leu His Ser Ala Ala Glu Phe Asp Ala Glu Phe Phe
        1125                1130                1135

Gly Ile Ser Pro Arg Glu Ala Thr Ala Met Asp Pro Gln Gln Arg Leu
        1140                1145                1150

Leu Leu Glu Ala Ser Trp Glu Ala Leu Glu Asp Ala Gly Val Leu Pro
        1155                1160                1165

Glu Ser Leu Arg Gly Gly Asp Ala Gly Val Phe Val Gly Ala Thr Ala
        1170                1175                1180

Pro Glu Tyr Gly Pro Arg Leu His Glu Gly Ala Asp Gly Tyr Glu Gly
1185                1190                1195                1200

Tyr Leu Leu Thr Gly Thr Thr Ala Ser Val Ala Ser Gly Arg Ile Ala
                1205                1210                1215

Tyr Thr Leu Gly Thr Gly Gly Pro Ala Leu Thr Val Asp Thr Ala Cys
                1220                1225                1230

Ser Ser Ser Leu Val Ala Leu His Leu Ala Val Gln Ala Leu Arg Arg
        1235                1240                1245

Gly Glu Cys Gly Leu Ala Leu Ala Gly Gly Ala Thr Val Met Ser Gly
        1250                1255                1260

Pro Gly Met Phe Val Glu Phe Ser Arg Gln Arg Gly Leu Ala Pro Asp
1265                1270                1275                1280

Gly Arg Cys Met Pro Phe Ser Ala Asp Ala Asp Gly Thr Ala Trp Ser
                1285                1290                1295

Glu Gly Val Ala Val Leu Ala Leu Glu Arg Leu Ser Asp Ala Arg Arg
        1300                1305                1310

Ala Gly His Arg Val Leu Gly Val Val Arg Gly Ser Ala Val Asn Gln
        1315                1320                1325

Asp Gly Ala Ser Asn Gly Leu Thr Ala Pro Asn Arg Ser Ala Gln Glu
```

```
                 1330                1335                1340
Gly Val Ile Arg Ala Ala Leu Ala Asp Ala Gly Leu Ala Pro Gly Asp
1345                1350                1355                1360

Val Asp Ala Val Glu Ala His Gly Thr Gly Thr Ala Leu Gly Asp Pro
                1365                1370                1375

Ile Glu Ala Ser Ala Leu Leu Ala Thr Tyr Gly Arg Glu Arg Val Gly
            1380                1385                1390

Asp Pro Leu Trp Leu Gly Ser Leu Lys Ser Asn Val Gly His Thr Gln
        1395                1400                1405

Ala Ala Ala Gly Ala Ala Gly Val Val Lys Met Leu Leu Ala Leu Glu
    1410                1415                1420

His Gly Thr Leu Pro Arg Thr Leu His Ala Asp Arg Pro Ser Thr His
1425                1430                1435                1440

Val Asp Trp Ser Ser Gly Thr Val Ala Leu Leu Ala Glu Ala Arg Arg
                1445                1450                1455

Trp Pro Arg Arg Ser Asp Arg Pro Arg Arg Ala Ala Val Ser Ser Phe
            1460                1465                1470

Gly Ile Ser Gly Thr Asn Ala His Leu Ile Ile Glu Glu Ala Pro Glu
        1475                1480                1485

Trp Val Glu Asp Ile Asp Gly Val Ala Ala Pro Asp Arg Gly Thr Ala
    1490                1495                1500

Asp Ala Ala Pro Ser Pro Leu Leu Leu Ser Ala Arg Ser Glu Gly
1505                1510                1515                1520

Ala Leu Arg Ala Gln Ala Val Arg Leu Gly Glu Tyr Val Glu Arg Val
                1525                1530                1535

Gly Ala Asp Pro Arg Asp Val Ala Tyr Ser Leu Ala Ser Thr Arg Thr
            1540                1545                1550

Leu Phe Glu His Arg Ala Val Val Pro Cys Gly Gly Arg Gly Glu Leu
        1555                1560                1565

Val Ala Ala Leu Gly Gly Phe Ala Ala Gly Arg Val Ser Gly Gly Val
    1570                1575                1580

Arg Ser Gly Arg Ala Val Pro Gly Gly Val Gly Val Leu Phe Thr Gly
1585                1590                1595                1600

Gln Gly Ala Gln Trp Val Gly Met Gly Arg Gly Leu Tyr Ala Gly Gly
                1605                1610                1615

Gly Val Phe Ala Glu Val Leu Asp Glu Val Leu Ser Met Val Gly Glu
            1620                1625                1630

Val Asp Gly Arg Ser Leu Arg Asp Val Met Phe Gly Asp Val Asp Val
        1635                1640                1645

Asp Ala Gly Ala Gly Ala Asp Ala Gly Ala Gly Ala Gly Ala Gly Val
    1650                1655                1660

Gly Ser Gly Ser Gly Ser Val Gly Gly Leu Leu Gly Arg Thr Glu Phe
1665                1670                1675                1680

Ala Gln Pro Ala Leu Phe Ala Leu Glu Val Ala Leu Phe Arg Ala Leu
                1685                1690                1695

Glu Ala Arg Gly Val Glu Val Ser Val Val Leu Gly His Ser Val Gly
            1700                1705                1710

Glu Val Ala Ala Ala Tyr Val Ala Gly Val Leu Ser Leu Gly Asp Ala
        1715                1720                1725

Val Arg Leu Val Val Ala Arg Gly Gly Leu Met Gly Gly Leu Pro Val
    1730                1735                1740

Gly Gly Gly Met Trp Ser Val Gly Ala Ser Glu Ser Val Val Arg Gly
1745                1750                1755                1760
```

-continued

Val Val Glu Gly Leu Gly Glu Trp Val Ser Val Ala Ala Val Asn Gly
                1765                1770                1775

Pro Arg Ser Val Val Leu Ser Gly Asp Val Gly Val Leu Glu Ser Val
                1780                1785                1790

Val Ala Ser Leu Met Gly Asp Gly Val Glu Cys Arg Arg Leu Asp Val
                1795                1800                1805

Ser His Gly Phe His Ser Val Leu Met Glu Pro Val Leu Gly Glu Phe
                1810                1815                1820

Arg Gly Val Val Glu Ser Leu Glu Phe Gly Arg Val Arg Pro Gly Val
1825                1830                1835                1840

Val Val Val Ser Gly Val Ser Gly Gly Val Val Gly Ser Gly Glu Leu
                1845                1850                1855

Gly Asp Pro Gly Tyr Trp Val Arg His Ala Arg Glu Ala Val Arg Phe
                1860                1865                1870

Ala Asp Gly Val Gly Val Arg Gly Leu Gly Val Gly Thr Leu Val
                1875                1880                1885

Glu Val Gly Pro His Gly Val Leu Thr Gly Met Ala Gly Glu Cys Leu
                1890                1895                1900

Gly Ala Gly Asp Asp Val Val Val Pro Ala Met Arg Arg Gly Arg
1905                1910                1915                1920

Ala Glu Arg Glu Val Phe Glu Ala Ala Leu Ala Thr Val Phe Thr Arg
                1925                1930                1935

Asp Ala Gly Leu Asp Ala Thr Ala Leu His Thr Gly Ser Thr Gly Arg
                1940                1945                1950

Arg Ile Asp Leu Pro Thr Tyr Pro Phe Gln Arg Asp Arg Tyr Trp Leu
                1955                1960                1965

Asp Pro Val Arg Thr Ala Val Thr Gly Val Glu Pro Ala Gly Ser Pro
                1970                1975                1980

Ala Asp Ala Arg Ala Thr Glu Arg Gly Arg Ser Thr Thr Ala Gly Ile
1985                1990                1995                2000

Arg Tyr Arg Val Ala Trp Gln Pro Ala Val Asp Arg Gly Asn Pro
                2005                2010                2015

Gly Pro Ala Gly His Val Leu Leu Ala Pro Asp Glu Asp Thr Ala
                2020                2025                2030

Asp Ser Gly Leu Ala Pro Ala Ile Ala Arg Glu Leu Ala Val Arg Gly
                2035                2040                2045

Ala Glu Val His Thr Val Ala Val Pro Val Gly Thr Gly Arg Glu Ala
                2050                2055                2060

Ala Gly Asp Leu Leu Arg Ala Ala Gly Asp Gly Ala Ala Arg Ser Thr
2065                2070                2075                2080

Arg Val Leu Trp Leu Ala Pro Ala Glu Pro Asp Ala Ala Asp Ala Val
                2085                2090                2095

Ala Leu Val Gln Ala Leu Gly Glu Ala Val Pro Glu Ala Pro Leu Trp
                2100                2105                2110

Ile Thr Thr Arg Glu Ala Ala Val Arg Pro Asp Glu Thr Pro Ser
                2115                2120                2125

Val Gly Gly Ala Gln Leu Trp Gly Leu Gly Gln Val Ala Ala Leu Glu
                2130                2135                2140

Leu Gly Arg Arg Trp Gly Gly Leu Ala Asp Leu Pro Gly Ser Ala Ser
2145                2150                2155                2160

Pro Ala Val Leu Arg Thr Phe Val Gly Ala Leu Leu Ala Gly Gly Glu
                2165                2170                2175

Asn Gln Phe Ala Val Arg Pro Ser Gly Val His Val Arg Arg Val Val
                2180                2185                2190

-continued

```
Pro Ala Pro Val Pro Val Pro Ala Ser Ala Arg Thr Val Thr Thr Ala
    2195                2200                2205

Pro Ala Thr Ala Val Gly Glu Asp Ala Arg Asn Asp Thr Ser Asp Val
    2210                2215                2220

Val Val Pro Asp Asp Arg Trp Ser Ser Gly Thr Val Leu Ile Thr Gly
2225                2230                2235                2240

Gly Thr Gly Ala Leu Gly Ala Gln Val Ala Arg Arg Leu Ala Arg Ser
                2245                2250                2255

Gly Ala Ala Arg Leu Leu Leu Val Gly Arg Arg Gly Ala Ala Gly Pro
            2260                2265                2270

Gly Val Gly Glu Leu Val Glu Glu Leu Thr Ala Leu Gly Ser Glu Val
            2275                2280                2285

Ala Val Glu Ala Cys Asp Val Ala Asp Arg Asp Ala Leu Ala Ala Leu
            2290                2295                2300

Leu Ala Gly Leu Pro Glu Glu Arg Pro Leu Val Ala Val Leu His Ala
2305                2310                2315                2320

Ala Gly Val Leu Asp Asp Gly Val Leu Asp Ser Leu Thr Ser Asp Arg
                2325                2330                2335

Val Asp Ala Val Leu Arg Asp Lys Val Thr Ala Ala Arg His Leu Asp
            2340                2345                2350

Glu Leu Thr Ala Asp Leu Pro Leu Asp Ala Phe Val Leu Phe Ser Ser
            2355                2360                2365

Ile Val Gly Val Trp Gly Asn Gly Gly Gln Ala Val Tyr Ala Ala Ala
    2370                2375                2380

Asn Ala Ala Leu Asp Ala Leu Ala Gln Arg Arg Arg Ala Arg Gly Ala
2385                2390                2395                2400

Arg Ala Ala Ser Ile Ala Trp Gly Pro Trp Ala Gly Ala Gly Met Ala
                2405                2410                2415

Ser Gly Thr Ala Ala Lys Ser Phe Glu Arg Asp Gly Val Thr Ala Leu
            2420                2425                2430

Asp Pro Glu Arg Ala Leu Asp Val Leu Asp Asp Val Val Gly Ala Gly
            2435                2440                2445

Gly Thr Ser Ala Ala Gly Thr His Ala Ala Gly Glu Ser Ser Leu Leu
            2450                2455                2460

Val Ala Asp Val Asp Trp Glu Thr Phe Val Gly Arg Ser Val Thr Arg
2465                2470                2475                2480

Arg Thr Trp Ser Leu Phe Asp Gly Val Ser Ala Ala Arg Ser Ala Arg
                2485                2490                2495

Ala Gly His Ala Ala Asp Asp Arg Ala Ala Leu Thr Pro Gly Thr Arg
            2500                2505                2510

Pro Gly Asp Gly Ala Pro Gly Gly Ser Gly Gln Asp Gly Gly Glu Gly
            2515                2520                2525

Arg Pro Trp Leu Ser Val Gly Pro Ser Pro Ala Glu Arg Arg Arg Ala
    2530                2535                2540

Leu Leu Thr Leu Val Arg Ser Glu Ala Ala Gly Ile Leu Arg His Ala
2545                2550                2555                2560

Ser Ala Asp Ala Val Asp Pro Glu Leu Ala Phe Arg Ser Ala Gly Phe
                2565                2570                2575

Asp Ser Leu Thr Val Leu Glu Leu Arg Asn Arg Leu Thr Ala Ala Thr
            2580                2585                2590

Gly Leu Asn Leu Pro Asn Thr Leu Leu Phe Asp His Pro Thr Pro Leu
            2595                2600                2605

Ser Leu Ala Ser His Leu His Asp Glu Leu Phe Gly Pro Asp Ser Glu
```

```
             2610                2615                2620
Ala Glu Pro Ala Ala Ala Pro Thr Pro Val Met Ala Asp Glu Arg
2625                2630                2635                2640
Glu Pro Ile Ala Ile Val Gly Met Ala Cys Arg Tyr Pro Gly Gly Val
                2645                2650                2655
Ala Ser Pro Asp Asp Leu Trp Asp Leu Val Ala Gly Asp Gly His Thr
                2660                2665                2670
Leu Ser Pro Phe Pro Ala Asp Arg Gly Trp Asp Val Glu Gly Leu Tyr
            2675                2680                2685
Asp Pro Glu Pro Gly Val Pro Gly Lys Ser Tyr Val Arg Glu Gly Gly
            2690                2695                2700
Phe Leu Arg Ser Ala Ala Glu Phe Asp Ala Glu Phe Phe Gly Ile Ser
2705                2710                2715                2720
Pro Arg Glu Ala Thr Ala Met Asp Pro Gln Gln Arg Leu Leu Leu Glu
                2725                2730                2735
Thr Ser Trp Glu Ala Leu Glu Arg Ala Gly Ile Val Pro Asp Ser Leu
                2740                2745                2750
Arg Gly Thr Arg Thr Gly Val Phe Ser Gly Ile Ser Gln Gln Asp Tyr
                2755                2760                2765
Ala Thr Gln Leu Gly Asp Ala Ala Asp Thr Tyr Gly Gly His Val Leu
            2770                2775                2780
Thr Gly Thr Leu Gly Ser Val Ile Ser Gly Arg Val Ala Tyr Ala Leu
2785                2790                2795                2800
Gly Leu Glu Gly Pro Ala Leu Thr Val Asp Thr Ala Cys Ser Ser Ser
                2805                2810                2815
Leu Val Ala Leu His Leu Ala Val Gln Ser Leu Arg Arg Gly Glu Cys
            2820                2825                2830
Asp Leu Ala Leu Ala Gly Gly Val Thr Val Met Ala Thr Pro Thr Val
            2835                2840                2845
Phe Val Glu Phe Ser Arg Gln Arg Gly Leu Ala Ala Asp Gly Arg Cys
            2850                2855                2860
Lys Ala Phe Ala Glu Gly Ala Asp Gly Thr Ala Trp Ala Glu Gly Val
2865                2870                2875                2880
Gly Val Leu Leu Val Glu Arg Leu Ser Asp Ala Arg Arg Asn Gly His
                2885                2890                2895
Arg Val Leu Ala Val Val Arg Gly Ser Ala Val Asn Gln Asp Gly Ala
                2900                2905                2910
Ser Asn Gly Leu Thr Ala Pro Ser Gly Pro Ala Gln Gln Arg Val Ile
            2915                2920                2925
Arg Glu Ala Leu Ala Asp Ala Gly Leu Val Pro Ala Asp Val Asp Val
            2930                2935                2940
Val Glu Ala His Gly Thr Gly Thr Ala Leu Gly Asp Pro Ile Glu Ala
2945                2950                2955                2960
Gly Ala Leu Leu Ala Thr Tyr Gly Arg Glu Arg Val Gly Asp Pro Leu
                2965                2970                2975
Trp Leu Gly Ser Leu Lys Ser Asn Ile Gly His Ala Gln Ala Ala Ala
                2980                2985                2990
Gly Val Gly Gly Val Ile Lys Val Val Gln Gly Met Arg His Gly Ser
            2995                3000                3005
Leu Pro Arg Thr Leu His Val Asp Ala Pro Ser Ser Lys Val Glu Trp
            3010                3015                3020
Ala Ser Gly Ala Val Glu Leu Leu Thr Glu Thr Arg Ser Trp Pro Arg
3025                3030                3035                3040
```

-continued

Arg Val Glu Arg Val Arg Arg Ala Ala Val Ser Ala Phe Gly Val Ser
            3045                3050                3055

Gly Thr Asn Ala His Val Val Leu Glu Glu Ala Pro Ala Glu Ala Gly
            3060                3065                3070

Ser Glu His Gly Asp Gly Pro Glu Pro Glu Arg Pro Asp Ala Val Thr
            3075                3080                3085

Gly Pro Leu Ser Trp Val Leu Ser Ala Arg Ser Glu Gly Ala Leu Arg
            3090                3095                3100

Ala Gln Ala Val Arg Leu Arg Glu Cys Val Glu Arg Val Gly Ala Asp
3105                3110                3115                3120

Pro Arg Asp Val Ala Gly Ser Leu Val Val Ser Arg Ala Ser Phe Gly
            3125                3130                3135

Glu Arg Ala Val Val Val Gly Arg Gly Arg Glu Glu Leu Leu Ala Gly
            3140                3145                3150

Leu Asp Val Val Ala Ala Gly Ala Pro Val Gly Val Ser Ser Gly Ala
            3155                3160                3165

Gly Ala Val Val Arg Gly Ser Ala Val Arg Gly Arg Gly Val Gly Val
            3170                3175                3180

Leu Phe Thr Gly Gln Gly Ala Gln Trp Val Gly Met Gly Arg Gly Leu
3185                3190                3195                3200

Tyr Ala Gly Gly Gly Val Phe Ala Glu Val Leu Asp Glu Val Leu Ser
            3205                3210                3215

Val Val Gly Glu Val Asp Gly Arg Ser Leu Arg Asp Val Met Phe Ala
            3220                3225                3230

Asp Ala Asp Ser Val Leu Gly Gly Leu Leu Gly Arg Thr Glu Phe Ala
            3235                3240                3245

Gln Pro Ala Leu Phe Ala Leu Glu Val Ala Leu Phe Arg Ala Leu Glu
            3250                3255                3260

Ala Arg Gly Val Glu Val Ser Val Val Leu Gly His Ser Val Gly Glu
3265                3270                3275                3280

Val Ala Ala Ala Tyr Val Ala Gly Val Leu Ser Leu Gly Asp Ala Val
            3285                3290                3295

Arg Leu Val Val Ala Arg Gly Gly Leu Met Gly Gly Leu Pro Val Gly
            3300                3305                3310

Gly Gly Met Trp Ser Val Gly Ala Ser Glu Ser Val Val Arg Gly Val
            3315                3320                3325

Val Glu Gly Leu Gly Glu Trp Val Ser Val Ala Ala Val Asn Gly Pro
            3330                3335                3340

Arg Ser Val Val Leu Ser Gly Asp Val Gly Val Leu Glu Ser Val Val
3345                3350                3355                3360

Val Thr Leu Met Gly Asp Gly Val Glu Cys Arg Arg Leu Asp Val Ser
            3365                3370                3375

His Gly Phe His Ser Val Leu Met Glu Pro Val Leu Gly Glu Phe Arg
            3380                3385                3390

Gly Val Val Glu Ser Leu Glu Phe Gly Arg Val Arg Pro Gly Val Val
            3395                3400                3405

Val Val Ser Gly Val Ser Gly Gly Val Val Gly Ser Gly Glu Leu Gly
            3410                3415                3420

Asp Pro Gly Tyr Trp Val Arg His Ala Arg Glu Ala Val Arg Phe Ala
3425                3430                3435                3440

Asp Gly Val Gly Val Val Arg Gly Leu Gly Val Gly Thr Leu Val Glu
            3445                3450                3455

Val Gly Pro His Gly Val Leu Thr Gly Met Ala Gly Gln Cys Leu Glu
            3460                3465                3470

```
Ala Gly Asp Asp Val Val Val Pro Ala Met Arg Arg Gly Arg Pro
        3475                3480                3485
Glu Arg Glu Val Phe Glu Ala Ala Leu Ala Thr Val Phe Thr Arg Asp
        3490                3495                3500
Ala Gly Leu Asp Ala Thr Thr Leu His Thr Gly Ser Thr Gly Arg Arg
3505                3510                3515                3520
Ile Asp Leu Pro Thr Tyr Pro Phe Gln His Asn Arg Tyr Trp Ala Thr
            3525                3530                3535
Gly Ser Val Thr Gly Ala Thr Gly Thr Ser Ala Ala Arg Phe Gly
        3540                3545                3550
Leu Glu Trp Lys Asp His Pro Phe Leu Ser Gly Ala Thr Pro Ile Ala
            3555                3560                3565
Gly Ser Gly Ala Leu Leu Leu Thr Gly Arg Val Gly Leu Ala Ala His
        3570                3575                3580
Pro Trp Leu Ala Asp His Ala Ile Ser Gly Thr Val Leu Leu Pro Gly
3585                3590                3595                3600
Thr Ala Ile Ala Asp Leu Leu Leu Arg Ala Val Glu Glu Val Gly Ala
            3605                3610                3615
Gly Gly Val Glu Glu Leu Thr Leu His Glu Pro Leu Leu Pro Glu
        3620                3625                3630
Arg Gly Gly Leu His Val Gln Val Leu Val Glu Ala Ala Asp Glu Gln
            3635                3640                3645
Gly Arg Arg Ala Val Ala Val Ala Ala Arg Pro Glu Gly Pro Gly Arg
        3650                3655                3660
Asp Gly Glu Glu Gln Glu Trp Thr Arg His Ala Glu Gly Val Leu Thr
3665                3670                3675                3680
Ser Thr Glu Thr Ala Val Pro Asp Met Gly Trp Ala Ala Gly Ala Trp
            3685                3690                3695
Pro Pro Pro Gly Ala Glu Pro Ile Asp Val Glu Glu Leu Tyr Asp Ala
        3700                3705                3710
Phe Ala Ala Asp Gly Tyr Gly Tyr Gly Pro Ala Phe Thr Ala Leu Ser
            3715                3720                3725
Gly Val Trp Arg Leu Gly Asp Glu Leu Phe Ala Glu Val Arg Arg Pro
        3730                3735                3740
Ala Gly Gly Ala Gly Thr Thr Gly Asp Gly Phe Gly Val His Pro Ala
3745                3750                3755                3760
Leu Phe Asp Ala Ala Leu His Pro Trp Arg Ala Gly Gly Leu Leu Pro
            3765                3770                3775
Asp Thr Gly Gly Thr Thr Trp Ala Pro Phe Ser Trp Gln Gly Ile Ala
            3780                3785                3790
Leu His Thr Thr Gly Ala Glu Thr Leu Arg Val Arg Leu Ala Pro Ala
            3795                3800                3805
Ala Gly Gly Thr Glu Ser Ala Phe Ser Val Gln Ala Ala Asp Pro Ala
            3810                3815                3820
Gly Thr Pro Val Leu Thr Leu Asp Ala Leu Leu Leu Arg Pro Val Thr
3825                3830                3835                3840
Leu Gly Arg Ala Asp Ala Pro Gln Pro Leu Tyr Arg Val Asp Trp Gln
            3845                3850                3855
Pro Val Gly Gln Gly Thr Glu Ala Ser Gly Ala Gln Gly Trp Thr Val
            3860                3865                3870
Leu Gly Gln Ala Ala Ala Glu Thr Val Ala Gln Pro Ala Ala His Ala
            3875                3880                3885
Asp Leu Thr Ala Leu Arg Thr Ala Val Ala Ala Ala Gly Thr Pro Val
```

-continued

```
                3890                3895                3900
Pro Arg Leu Val Val Ser Pro Val Asp Thr Arg Leu Asp Glu Gly
3905                3910                3915                3920

Pro Val Leu Ala Asp Ala Glu Ala Arg Ala Arg Ala Gly Asp Gly Trp
        3925                3930                3935

Asp Asp Asp Pro Leu Arg Val Ala Leu Gly Arg Gly Leu Thr Leu Val
            3940                3945                3950

Arg Glu Trp Val Glu Asp Glu Arg Leu Ala Asp Ser Arg Leu Val Val
        3955                3960                3965

Leu Thr Arg Gly Ala Val Ala Ala Gly Pro Gly Asp Val Pro Asp Leu
        3970                3975                3980

Thr Gly Ala Ala Leu Trp Gly Leu Leu Arg Ser Ala Gln Ser Glu Tyr
3985                3990                3995                4000

Pro Asp Arg Phe Thr Leu Ile Asp Val Asp Asp Ser Pro Glu Ser Arg
            4005                4010                4015

Ala Ala Leu Pro Arg Ala Leu Gly Ser Ala Glu Arg Gln Leu Ala Leu
            4020                4025                4030

Arg Thr Gly Asp Val Leu Ala Pro Ala Leu Val Pro Met Ala Thr Arg
            4035                4040                4045

Pro Ala Glu Thr Thr Pro Ala Thr Ala Val Ala Ser Ala Thr Thr Gln
4050                4055                4060

Thr Gln Val Thr Ala Pro Ala Pro Asp Asp Pro Ala Ala Asp Ala Val
4065                4070                4075                4080

Phe Asp Pro Ala Gly Thr Val Leu Ile Thr Gly Gly Thr Gly Ala Leu
            4085                4090                4095

Gly Arg Arg Val Ala Ser His Leu Ala Arg Arg Tyr Gly Val Arg His
            4100                4105                4110

Met Leu Leu Val Ser Arg Arg Gly Pro Asp Ala Pro Glu Ala Gly Pro
            4115                4120                4125

Leu Glu Arg Glu Leu Ala Gly Leu Gly Val Thr Ala Thr Phe Leu Ala
            4130                4135                4140

Cys Asp Leu Thr Asp Ile Glu Ala Val Arg Lys Ala Val Ala Ala Val
4145                4150                4155                4160

Pro Ser Asp His Pro Leu Thr Gly Val Val His Thr Ala Gly Val Leu
            4165                4170                4175

Asp Asp Gly Ala Leu Thr Gly Leu Thr Arg Gln Arg Leu Asp Thr Val
            4180                4185                4190

Leu Arg Pro Lys Ala Asp Ala Val Arg Asn Leu His Glu Ala Thr Leu
            4195                4200                4205

Asp Arg Pro Leu Arg Ala Phe Val Leu Phe Ser Ala Ala Ala Gly Leu
            4210                4215                4220

Leu Gly Arg Pro Gly Gln Ala Ser Tyr Ala Ala Ala Asn Ala Val Leu
4225                4230                4235                4240

Asp Ala Leu Ala Gly Ala Arg Arg Ala Ala Gly Leu Pro Ala Val Ser
            4245                4250                4255

Leu Ala Trp Gly Leu Trp Asp Glu Gln Thr Gly Met Ala Gly Gly Leu
            4260                4265                4270

Asp Glu Met Ala Leu Arg Val Leu Arg Arg Asp Gly Ile Ala Ala Met
            4275                4280                4285

Pro Pro Glu Gln Gly Leu Glu Leu Leu Asp Leu Ala Leu Thr Gly His
            4290                4295                4300

Arg Asp Gly Pro Ala Val Leu Val Pro Leu Leu Leu Asp Gly Ala Ala
4305                4310                4315                4320
```

-continued

```
Leu Arg Arg Thr Ala Lys Glu Arg Gly Ala Ala Thr Met Ser Pro Leu
            4325                4330                4335

Leu Arg Ala Leu Leu Pro Ala Ala Leu Arg Arg Ser Gly Gly Ala Gly
            4340                4345                4350

Ala Pro Ala Ala Ala Asp Arg His Gly Lys Glu Ala Asp Pro Gly Ala
            4355                4360                4365

Gly Arg Leu Ala Gly Met Val Ala Leu Glu Ala Ala Glu Arg Ser Ala
            4370                4375                4380

Ala Val Leu Glu Leu Val Thr Glu Gln Val Ala Glu Val Leu Gly Tyr
4385                4390                4395                4400

Ala Ser Ala Ala Glu Ile Glu Pro Glu Arg Pro Phe Arg Glu Ile Gly
            4405                4410                4415

Val Asp Ser Leu Ala Ala Val Glu Leu Arg Asn Arg Leu Ser Arg Leu
            4420                4425                4430

Val Gly Leu Arg Leu Pro Thr Thr Leu Ser Phe Asp His Pro Thr Pro
            4435                4440                4445

Lys Asp Met Ala Gln His Ile Asp Gly Gln Leu Pro Arg Pro Ala Gly
            4450                4455                4460

Ala Ser Pro Ala Asp Ala Ala Leu Glu Gly Ile Gly Asp Leu Ala Arg
4465                4470                4475                4480

Ala Val Ala Leu Leu Gly Thr Gly Asp Ala Arg Arg Ala Glu Val Arg
            4485                4490                4495

Glu Gln Leu Val Gly Leu Leu Ala Ala Leu Asp Pro Pro Gly Arg Thr
            4500                4505                4510

Gly Thr Ala Ala Pro Gly Val Pro Ser Gly Ala Asp Gly Ala Glu Pro
            4515                4520                4525

Thr Val Thr Asp Arg Leu Asp Glu Ala Thr Asp Glu Ile Phe Ala
            4530                4535                4540

Phe Leu Asp Glu Gln Leu
4545                4550
```

(2) INFORMATION FOR SEQ ID NO:3:

(i) SEQUENCE CHARACTERISTICS:
        (A) LENGTH: 1996 amino acids
        (B) TYPE: amino acid
        (D) TOPOLOGY: unknown (ii) MOLECULE TYPE: peptide (xi) SEQUENCE DESCRIPTION: SEQ ID NO:3:

```
Met Thr Ala Glu Asn Asp Lys Ile Arg Ser Tyr Leu Lys Arg Ala Thr
1               5                   10                  15

Ala Glu Leu His Arg Thr Lys Ser Arg Leu Ala Glu Val Glu Ser Ala
                20                  25                  30

Ser Arg Glu Pro Ile Ala Ile Val Gly Met Ala Cys Arg Tyr Pro Gly
            35                  40                  45

Gly Val Ala Ser Pro Asp Asp Leu Trp Asp Leu Val Ala Ala Gly Thr
50                  55                  60

Asp Ala Val Ser Ala Phe Pro Val Asp Arg Gly Trp Asp Val Glu Gly
65                  70                  75                  80

Leu Tyr Asp Pro Asp Pro Glu Ala Val Gly Arg Ser Tyr Val Arg Glu
                85                  90                  95

Gly Gly Phe Leu His Ser Ala Ala Glu Phe Asp Ala Glu Phe Phe Gly
            100                 105                 110

Ile Ser Pro Arg Glu Ala Ala Ala Met Asp Pro Gln Gln Arg Leu Leu
        115                 120                 125
```

-continued

```
Leu Glu Thr Ser Trp Glu Ala Leu Glu Arg Ala Gly Ile Val Pro Ala
    130                 135                 140
Ser Leu Arg Gly Thr Arg Thr Gly Val Phe Thr Gly Val Met Tyr Asp
145                 150                 155                 160
Asp Tyr Gly Ser Arg Phe Asp Ser Ala Pro Pro Glu Tyr Glu Gly Tyr
                165                 170                 175
Leu Val Asn Gly Ser Ala Gly Ser Ile Ala Ser Gly Arg Val Ala Tyr
            180                 185                 190
Ala Leu Gly Leu Glu Gly Pro Ala Leu Thr Val Asp Thr Ala Cys Ser
        195                 200                 205
Ser Ser Leu Val Ala Leu His Leu Ala Val Gln Ser Leu Arg Arg Gly
    210                 215                 220
Glu Cys Asp Leu Ala Leu Ala Gly Gly Val Thr Val Met Ala Thr Pro
225                 230                 235                 240
Thr Val Leu Val Glu Phe Ser Arg Gln Arg Gly Leu Ala Ala Asp Gly
                245                 250                 255
Arg Cys Lys Ala Phe Ala Glu Gly Ala Asp Gly Thr Ala Trp Ala Glu
            260                 265                 270
Gly Val Gly Val Leu Leu Val Glu Arg Leu Ser Asp Ala Arg Arg Asn
        275                 280                 285
Gly His Arg Val Leu Ala Val Arg Gly Ser Ala Val Asn Gln Asp
    290                 295                 300
Gly Ala Ser Asn Gly Leu Thr Ala Pro Ser Gly Pro Ala Gln Gln Arg
305                 310                 315                 320
Val Ile Arg Glu Ala Leu Ala Asp Ala Gly Leu Thr Pro Ala Asp Val
                325                 330                 335
Asp Ala Val Glu Ala His Gly Thr Gly Thr Pro Leu Gly Asp Pro Ile
            340                 345                 350
Glu Ala Gly Ala Leu Leu Ala Thr Tyr Gly Ser Glu Arg Gln Gly Gln
        355                 360                 365
Gly Pro Leu Trp Leu Gly Ser Leu Lys Ser Asn Ile Gly His Ala Gln
    370                 375                 380
Ala Ala Ala Gly Val Gly Gly Val Ile Lys Val Val Gln Ala Met Arg
385                 390                 395                 400
His Gly Ser Leu Pro Arg Thr Leu His Val Asp Ala Pro Ser Ser Lys
                405                 410                 415
Val Glu Trp Ala Ser Gly Ala Val Glu Leu Leu Thr Glu Thr Arg Ser
            420                 425                 430
Trp Pro Arg Arg Val Glu Arg Val Arg Ala Ala Val Ser Ala Phe
        435                 440                 445
Gly Val Ser Gly Thr Asn Ala His Val Val Leu Glu Glu Ala Pro Ala
    450                 455                 460
Glu Ala Gly Ser Glu His Gly Asp Gly Pro Glu Pro Glu Arg Pro Asp
465                 470                 475                 480
Ala Val Thr Gly Pro Leu Ser Trp Val Leu Ser Ala Arg Ser Glu Gly
                485                 490                 495
Ala Leu Arg Ala Gln Ala Val Arg Leu Arg Glu Cys Val Glu Arg Val
            500                 505                 510
Gly Ala Asp Pro Arg Asp Val Ala Gly Ser Leu Val Val Ser Arg Ala
        515                 520                 525
Ser Phe Gly Glu Arg Ala Val Val Gly Arg Gly Arg Glu Glu Leu
    530                 535                 540
Leu Ala Gly Leu Asp Val Val Ala Ala Gly Ala Pro Val Gly Val Ser
```

```
            545                 550                 555                 560
Gly Gly Val Ser Ser Gly Ala Gly Ala Val Arg Gly Ser Ala Val
                565                 570                 575
Arg Gly Arg Gly Val Gly Val Leu Phe Thr Gly Gln Gly Ala Gln Trp
            580                 585                 590
Val Gly Met Gly Arg Gly Leu Tyr Ala Gly Gly Val Phe Ala Glu
            595                 600                 605
Val Leu Asp Glu Val Leu Ser Val Gly Glu Val Gly Gly Trp Ser
            610                 615                 620
Leu Arg Asp Val Met Phe Gly Asp Val Asp Val Asp Ala Gly Ala Gly
625                 630                 635                 640
Ala Asp Ala Gly Val Gly Ser Gly Val Gly Val Gly Gly Leu Leu Gly
                645                 650                 655
Arg Thr Glu Phe Ala Gln Pro Ala Leu Phe Ala Leu Glu Val Ala Leu
            660                 665                 670
Phe Arg Ala Leu Glu Ala Arg Gly Val Glu Val Ser Val Val Leu Gly
            675                 680                 685
His Ser Val Gly Glu Val Ala Ala Ala Tyr Val Ala Gly Val Leu Ser
            690                 695                 700
Leu Gly Asp Ala Val Arg Leu Val Val Ala Arg Gly Gly Leu Met Gly
705                 710                 715                 720
Gly Leu Pro Val Gly Gly Gly Met Trp Ser Val Gly Ala Ser Glu Ser
                725                 730                 735
Val Val Arg Gly Val Val Glu Gly Leu Gly Glu Trp Val Ser Val Ala
                740                 745                 750
Ala Val Asn Gly Pro Arg Ser Val Val Leu Ser Gly Asp Val Gly Val
                755                 760                 765
Leu Glu Ser Val Val Ala Ser Leu Met Gly Asp Gly Val Glu Cys Arg
            770                 775                 780
Arg Leu Asp Val Ser His Gly Phe His Ser Val Leu Met Glu Pro Val
785                 790                 795                 800
Leu Gly Glu Phe Arg Gly Val Val Glu Ser Leu Glu Phe Gly Arg Val
            805                 810                 815
Arg Pro Gly Val Val Val Ser Ser Val Ser Gly Gly Val Val Gly
            820                 825                 830
Ser Gly Glu Leu Gly Asp Pro Gly Tyr Trp Val Arg His Ala Arg Glu
            835                 840                 845
Ala Val Arg Phe Ala Asp Gly Val Gly Val Val Arg Gly Leu Gly Val
            850                 855                 860
Gly Thr Leu Val Glu Val Gly Pro His Gly Val Leu Thr Gly Met Ala
865                 870                 875                 880
Gly Glu Cys Leu Gly Ala Gly Asp Asp Val Val Val Val Pro Ala Met
                885                 890                 895
Arg Arg Gly Arg Ala Glu Arg Glu Val Phe Glu Ala Ala Leu Ala Thr
                900                 905                 910
Val Phe Thr Arg Asp Ala Gly Leu Asp Ala Thr Thr Leu His Thr Gly
            915                 920                 925
Ser Thr Gly Arg Arg Ile Asp Leu Pro Thr Tyr Pro Phe Gln His Asp
            930                 935                 940
Arg Tyr Trp Leu Ala Ala Pro Ser Arg Pro Arg Thr Asp Gly Leu Ser
945                 950                 955                 960
Ala Ala Gly Leu Arg Glu Val Glu His Pro Leu Leu Thr Ala Ala Val
                965                 970                 975
```

-continued

Glu Leu Pro Gly Thr Asp Thr Glu Val Trp Thr Gly Arg Ile Ser Ala
        980                 985                 990

Ala Asp Leu Pro Trp Leu Ala Asp His Leu Val Trp Asp Arg Gly Val
        995                 1000                1005

Val Pro Gly Thr Ala Leu Leu Glu Thr Val Leu Gln Val Gly Ser Arg
        1010                1015                1020

Ile Gly Leu Pro Arg Val Ala Glu Leu Val Leu Glu Thr Pro Leu Thr
1025                1030                1035                1040

Trp Thr Ser Asp Arg Pro Leu Gln Val Arg Ile Val Val Thr Ala Ala
                1045                1050                1055

Ala Thr Ala Pro Gly Gly Ala Arg Glu Leu Thr Leu His Ser Arg Pro
                1060                1065                1070

Glu Pro Val Ala Ala Ser Ser Ser Pro Ser Pro Ala Ser Pro Arg
        1075                1080                1085

His Leu Thr Ala Gln Glu Ser Asp Asp Asp Trp Thr Arg His Ala Ser
        1090                1095                1100

Gly Leu Leu Ala Pro Ala Ala Gly Leu Ala Asp Asp Phe Ala Glu Leu
1105                1110                1115                1120

Thr Gly Ala Trp Pro Pro Val Gly Ala Glu Pro Leu Asp Leu Ala Gly
                1125                1130                1135

Gln Tyr Pro Leu Phe Ala Ala Ala Gly Val Arg Tyr Glu Gly Ala Phe
        1140                1145                1150

Arg Gly Leu Arg Ala Ala Trp Arg Arg Gly Asp Glu Val Phe Ala Asp
        1155                1160                1165

Val Arg Leu Pro Asp Ala His Ala Val Asp Ala Asp Arg Tyr Gly Val
        1170                1175                1180

His Pro Ala Leu Leu Asp Ala Val Leu His Pro Ile Ala Ser Leu Asp
1185                1190                1195                1200

Pro Leu Gly Asp Gly Gly His Gly Leu Leu Pro Phe Ser Trp Thr Asp
                1205                1210                1215

Val Gln Gly His Gly Ala Gly Gly His Ala Leu Arg Val Arg Val Ala
        1220                1225                1230

Ala Val Asp Gly Gly Ala Val Ser Val Thr Ala Ala Asp His Ala Gly
        1235                1240                1245

Asn Pro Val Leu Ser Ala Arg Ser Leu Ala Leu Arg Arg Ile Thr Ala
        1250                1255                1260

Asp Arg Leu Pro Ala Ala Pro Val Ala Pro Leu Tyr Arg Val Asp Trp
1265                1270                1275                1280

Leu Pro Phe Pro Gly Pro Val Pro Val Ser Ala Gly Gly Arg Trp Ala
                1285                1290                1295

Val Val Gly Pro Glu Ala Glu Ala Thr Ala Ala Gly Leu Arg Ala Val
        1300                1305                1310

Gly Leu Asp Val Arg Thr His Ala Leu Pro Leu Gly Glu Pro Leu Pro
        1315                1320                1325

Pro Gln Ala Gly Thr Asp Ala Glu Val Ile Ile Leu Asp Leu Thr Thr
        1330                1335                1340

Thr Ala Ala Gly Arg Thr Ala Ser Asp Gly Gly Arg Leu Ser Leu Leu
1345                1350                1355                1360

Asp Glu Val Arg Ala Thr Val Arg Arg Thr Leu Glu Ala Val Gln Ala
                1365                1370                1375

Arg Leu Ala Asp Thr Glu Thr Ala Pro Asp Val Asp Val Arg Thr Ala
                1380                1385                1390

Ala Arg Pro Arg Thr Ala Ala Arg Thr Ser Pro Arg Val Asp Thr Arg
                1395                1400                1405

-continued

```
Thr Gly Ala Arg Thr Ala Asp Gly Pro Arg Leu Val Val Leu Thr Arg
    1410                1415                1420

Gly Ala Ala Gly Pro Glu Gly Gly Ala Ala Asp Pro Ala Gly Ala Ala
1425                1430                1435                1440

Val Trp Gly Leu Val Arg Val Ala Gln Ala Glu Gln Pro Gly Arg Phe
                1445                1450                1455

Thr Leu Val Asp Val Asp Gly Thr Gln Ala Ser Leu Arg Ala Leu Pro
        1460                1465                1470

Gly Leu Leu Ala Thr Asp Ala Gly Gln Ser Ala Val Arg Asp Gly Arg
            1475                1480                1485

Val Thr Val Pro Arg Leu Val Pro Val Ala Asp Pro Val Pro His Gly
        1490                1495                1500

Gly Gly Thr Ala Ala Asp Gly Thr Gly Ala Gly Glu Pro Ser Ala Thr
1505                1510                1515                1520

Leu Asp Pro Glu Gly Thr Val Leu Ile Thr Gly Gly Thr Gly Ala Leu
                1525                1530                1535

Ala Ala Glu Thr Ala Arg His Leu Val Asp Arg His Lys Val Arg His
            1540                1545                1550

Leu Leu Leu Val Gly Arg Arg Gly Pro Asp Ala Pro Gly Val Asp Arg
            1555                1560                1565

Leu Val Ala Glu Leu Thr Glu Ser Gly Ala Glu Val Ala Val Arg Ala
        1570                1575                1580

Cys Asp Val Thr Asp Arg Asp Ala Leu Arg Arg Leu Leu Asp Ala Leu
1585                1590                1595                1600

Pro Asp Glu His Pro Leu Thr Cys Val His Thr Ala Gly Val Leu
                1605                1610                1615

Asp Asp Gly Val Leu Ser Ala Gln Thr Ala Glu Arg Ile Asp Thr Val
            1620                1625                1630

Leu Arg Pro Lys Ala Asp Ala Ala Val His Leu Asp Glu Leu Thr Arg
        1635                1640                1645

Glu Ile Gly Arg Val Pro Leu Val Leu Tyr Ser Ser Val Ser Ala Thr
        1650                1655                1660

Leu Gly Ser Ala Gly Gln Ala Gly Tyr Ala Ala Ala Asn Ala Phe Met
1665                1670                1675                1680

Asp Ala Leu Ala Ala Arg Arg Cys Ala Ala Gly His Pro Ala Leu Ser
            1685                1690                1695

Leu Gly Trp Gly Trp Trp Ser Gly Val Gly Leu Ala Thr Gly Leu Asp
            1700                1705                1710

Gly Ala Asp Ala Ala Arg Val Arg Arg Ser Gly Leu Ala Pro Leu Asp
        1715                1720                1725

Ala Gly Ala Ala Leu Asp Leu Leu Asp Arg Ala Leu Thr Arg Pro Glu
    1730                1735                1740

Pro Ala Leu Leu Pro Val Arg Leu Asp Leu Arg Ala Ala Gly Ala
1745                1750                1755                1760

Thr Ala Leu Pro Glu Val Leu Arg Asp Leu Ala Gly Val Pro Ala Asp
                1765                1770                1775

Ala Arg Ser Thr Pro Gly Ala Ala Ala Gly Thr Gly Asp Glu Asp Gly
            1780                1785                1790

Ala Val Arg Pro Ala Pro Ala Pro Ala Asp Ala Ala Gly Thr Leu Ala
        1795                1800                1805

Ala Arg Leu Ala Gly Arg Ser Ala Pro Glu Arg Thr Ala Leu Leu Leu
    1810                1815                1820

Asp Leu Val Arg Thr Glu Val Ala Ala Val Leu Gly His Gly Asp Pro
```

```
                1825                1830                1835                1840
Ala Ala Ile Gly Ala Ala Arg Thr Phe Lys Asp Ala Gly Phe Asp Ser
                    1845                1850                1855
Leu Thr Ala Val Asp Leu Arg Asn Arg Leu Asn Thr Arg Thr Gly Leu
                1860                1865                1870
Arg Leu Pro Ala Thr Leu Val Phe Asp His Pro Thr Pro Leu Ala Leu
                1875                1880                1885
Ala Glu Leu Leu Leu Asp Gly Leu Glu Ala Ala Gly Pro Ala Glu Pro
                1890                1895                1900
Ala Ala Glu Val Pro Asp Glu Ala Ala Gly Ala Glu Thr Leu Ser Gly
1905                1910                1915                1920
Val Ile Asp Arg Leu Glu Arg Ser Leu Ala Ala Thr Asp Asp Gly Asp
                1925                1930                1935
Ala Arg Val Arg Ala Ala Arg Arg Leu Arg Gly Leu Leu Asp Ala Leu
                1940                1945                1950
Pro Ala Gly Pro Gly Ala Ala Ser Gly Pro Asp Ala Gly Glu His Ala
                1955                1960                1965
Pro Gly Arg Gly Asp Val Val Ile Asp Arg Leu Arg Ser Ala Ser Asp
                1970                1975                1980
Asp Asp Leu Phe Asp Leu Leu Asp Ser Asp Phe Gln
1985                1990                1995

(2) INFORMATION FOR SEQ ID NO:4:

(i) SEQUENCE CHARACTERISTICS:
        (A) LENGTH: 3724 amino acids
        (B) TYPE: amino acid
        (D) TOPOLOGY: unknown (ii) MOLECULE TYPE: peptide (xi) SEQUENCE DESCRIPTION: SEQ ID NO:4:

Met Ser Ala Thr Asn Glu Glu Lys Leu Arg Glu Tyr Leu Arg Arg Ala
1               5                   10                  15

Met Ala Asp Leu His Ser Ala Arg Glu Arg Leu Arg Glu Val Glu Ser
                20                  25                  30

Ala Ser Arg Glu Pro Ile Ala Ile Val Gly Met Ala Cys Arg Tyr Pro
                35                  40                  45

Gly Gly Val Ala Ser Pro Glu Glu Leu Trp Asp Leu Val Ala Ala Gly
50                  55                  60

Thr Asp Ala Ile Ser Pro Phe Pro Val Asp Arg Gly Trp Asp Ala Glu
65                  70                  75                  80

Gly Leu Tyr Asp Pro Glu Pro Gly Val Pro Gly Lys Ser Tyr Val Arg
                85                  90                  95

Glu Gly Gly Phe Leu His Ser Ala Ala Glu Phe Asp Ala Glu Phe Phe
                100                 105                 110

Gly Ile Ser Pro Arg Glu Ala Ala Ala Met Asp Pro Gln Gln Arg Leu
                115                 120                 125

Leu Leu Glu Thr Ser Trp Glu Ala Leu Glu Arg Ala Gly Ile Val Pro
                130                 135                 140

Ala Ser Leu Arg Gly Thr Arg Thr Gly Val Phe Thr Gly Val Met Tyr
145                 150                 155                 160

His Asp Tyr Gly Ser His Gln Val Gly Thr Ala Ala Asp Pro Ser Gly
                165                 170                 175

Gln Leu Gly Leu Gly Thr Ala Gly Ser Val Ala Ser Gly Arg Val Ala
                180                 185                 190
```

-continued

```
Tyr Thr Leu Gly Leu Gln Gly Pro Ala Val Thr Met Asp Thr Ala Cys
        195                 200                 205

Ser Ser Ser Leu Val Ala Leu His Leu Ala Val Gln Ser Leu Arg Arg
210                 215                 220

Gly Glu Cys Asp Leu Ala Leu Ala Gly Gly Ala Thr Val Leu Ala Thr
225                 230                 235                 240

Pro Thr Val Phe Val Glu Phe Ser Arg Gln Arg Gly Leu Ala Ala Asp
                245                 250                 255

Gly Arg Cys Lys Ala Phe Ala Glu Gly Ala Asp Gly Thr Ala Trp Ala
            260                 265                 270

Glu Gly Ala Gly Val Leu Leu Val Glu Arg Leu Ser Asp Ala Arg Arg
        275                 280                 285

Asn Gly His Arg Val Leu Ala Val Arg Gly Ser Ala Val Asn Gln
    290                 295                 300

Asp Gly Ala Ser Asn Gly Leu Thr Ala Pro Ser Gly Pro Ala Gln Gln
305                 310                 315                 320

Arg Val Ile Arg Asp Ala Leu Ala Asp Ala Gly Leu Thr Pro Ala Asp
                325                 330                 335

Val Asp Ala Val Glu Ala His Gly Thr Gly Thr Pro Leu Gly Asp Pro
            340                 345                 350

Ile Glu Ala Gly Ala Leu Met Ala Thr Tyr Gly Ser Glu Arg Val Gly
        355                 360                 365

Asp Pro Leu Trp Leu Gly Ser Leu Lys Ser Asn Ile Gly His Thr Gln
370                 375                 380

Ala Ala Ala Gly Ala Ala Gly Val Ile Lys Met Val Gln Ala Leu Arg
385                 390                 395                 400

Gln Ser Glu Leu Pro Arg Thr Leu His Val Asp Ala Pro Ser Ala Lys
                405                 410                 415

Val Glu Trp Asp Ala Gly Ala Val Gln Leu Leu Thr Gly Val Arg Pro
            420                 425                 430

Trp Pro Arg Arg Glu His Arg Pro Arg Arg Ala Ala Val Ser Ala Phe
        435                 440                 445

Gly Val Ser Gly Thr Asn Ala His Val Ile Ile Glu Glu Pro Pro Ala
    450                 455                 460

Ala Gly Asp Thr Ser Pro Ala Gly Asp Thr Pro Glu Pro Gly Glu Ala
465                 470                 475                 480

Thr Ala Ser Pro Ser Thr Ala Ala Gly Pro Ser Ser Pro Ser Ala Val
                485                 490                 495

Ala Gly Pro Leu Ser Pro Ser Ser Pro Ala Val Val Trp Pro Leu Ser
            500                 505                 510

Ala Glu Thr Ala Pro Ala Leu Arg Ala Gln Ala Ala Arg Leu Arg Ala
        515                 520                 525

His Leu Glu Arg Leu Pro Gly Thr Ser Pro Thr Asp Ile Gly His Ala
    530                 535                 540

Leu Ala Ala Glu Arg Ala Ala Leu Thr Arg Arg Val Val Leu Leu Gly
545                 550                 555                 560

Asp Asp Gly Ala Pro Val Asp Ala Leu Ala Leu Ala Ala Gly Glu
                565                 570                 575

Thr Thr Pro Asp Ala Val His Gly Thr Ala Ala Asp Ile Arg Arg Val
            580                 585                 590

Ala Phe Val Phe Pro Gly Gln Gly Ser Gln Trp Ala Gly Met Gly Ala
        595                 600                 605

Glu Leu Leu Asp Thr Ala Pro Ala Phe Ala Ala Glu Leu Asp Arg Cys
    610                 615                 620
```

```
Gln Gly Ala Leu Ser Pro Tyr Val Asp Trp Asn Leu Ala Asp Val Leu
625                 630                 635                 640

Arg Gly Ala Pro Ala Ala Pro Gly Leu Asp Arg Val Asp Val Val Gln
            645                 650                 655

Pro Ala Thr Phe Ala Val Met Val Gly Leu Ala Ala Leu Trp Arg Ser
                660                 665                 670

Leu Gly Val Glu Pro Ala Ala Val Ile Gly His Ser Gln Gly Glu Ile
            675                 680                 685

Ala Ala Ala Cys Val Ala Gly Ala Leu Ser Leu Glu Asp Ala Ala Arg
690                 695                 700

Ile Val Ala Leu Arg Ser Gln Val Ile Ala Arg Glu Leu Ala Gly Arg
705                 710                 715                 720

Gly Gly Met Ala Ser Val Ala Leu Pro Ala Ala Glu Val Glu Ala Arg
                725                 730                 735

Leu Ala Gly Gly Val Glu Ile Ala Ala Val Asn Gly Pro Gly Ser Thr
                740                 745                 750

Val Val Cys Gly Glu Pro Gly Ala Leu Glu Ala Leu Leu Val Thr Leu
            755                 760                 765

Glu Ser Glu Gly Thr Arg Val Arg Arg Ile Asp Val Asp Tyr Ala Ser
770                 775                 780

His Ser His Tyr Val Glu Ser Ile Arg Ala Glu Leu Ala Thr Val Leu
785                 790                 795                 800

Gly Pro Val Arg Pro Arg Arg Gly Asp Val Pro Phe Tyr Ser Thr Val
                805                 810                 815

Glu Ala Ala Leu Leu Asp Thr Ala Thr Leu Asp Ala Asp Tyr Trp Tyr
                820                 825                 830

Arg Asn Leu Arg Leu Pro Val Arg Phe Glu Pro Thr Val Arg Ala Met
                835                 840                 845

Leu Asp Asp Gly Val Asp Ala Phe Val Glu Cys Ser Ala His Pro Val
850                 855                 860

Leu Thr Val Gly Val Arg Gln Thr Val Glu Ser Ala Gly Gly Ala Val
865                 870                 875                 880

Pro Ala Leu Ala Ser Leu Arg Arg Asp Glu Gly Gly Leu Arg Arg Phe
                885                 890                 895

Leu Thr Ser Ala Ala Glu Ala Gln Val Val Gly Val Pro Val Asp Trp
                900                 905                 910

Ala Thr Leu Arg Pro Gly Ala Gly Arg Val Asp Leu Pro Thr Tyr Ala
                915                 920                 925

Phe Gln Arg Glu Arg His Trp Val Gly Pro Ala Arg Pro Asp Ser Ala
930                 935                 940

Ala Thr Ala Ala Thr Thr Gly Asp Asp Ala Pro Glu Pro Gly Asp Arg
945                 950                 955                 960

Leu Gly Tyr His Val Ala Trp Lys Gly Leu Arg Ser Thr Thr Gly Gly
                965                 970                 975

Trp Arg Pro Gly Leu Arg Leu Leu Ile Val Pro Thr Gly Asp Gln Tyr
            980                 985                 990

Thr Ala Leu Ala Asp Thr Leu Glu Gln Ala Val Ala Ser Phe Gly Gly
            995                 1000                1005

Thr Val Arg Arg Val Ala Phe Asp Pro Ala Arg Thr Gly Arg Ala Glu
            1010                1015                1020

Leu Phe Gly Leu Leu Glu Thr Glu Ile Asn Gly Asp Thr Ala Val Thr
1025                1030                1035                1040

Gly Val Val Ser Leu Leu Gly Leu Cys Thr Asp Gly Arg Pro Asp His
```

-continued

```
                1045                1050                1055
Pro Ala Val Pro Val Ala Val Thr Ala Thr Leu Ala Leu Val Gln Ala
                    1060                1065                1070
Leu Ala Asp Leu Gly Ser Thr Ala Pro Leu Trp Thr Val Thr Cys Gly
        1075                1080                1085
Ala Val Ala Thr Ala Pro Asp Glu Leu Pro Cys Thr Ala Gly Ala Gln
    1090                1095                1100
Leu Trp Gly Leu Gly Arg Val Ala Ala Leu Glu Leu Pro Glu Val Trp
1105                1110                1115                1120
Gly Gly Leu Ile Asp Leu Pro Ala Arg Pro Asp Ala Arg Val Leu Asp
                1125                1130                1135
Arg Leu Ala Gly Val Leu Ala Glu Pro Gly Gly Glu Asp Gln Ile Ala
                    1140                1145                1150
Val Arg Met Ala Gly Val Phe Gly Arg Arg Val Leu Arg Asn Pro Ala
        1155                1160                1165
Asp Ser Arg Pro Pro Ala Trp Arg Ala Arg Gly Thr Val Leu Ile Ala
    1170                1175                1180
Gly Asp Leu Thr Thr Val Pro Gly Arg Leu Val Arg Ser Leu Leu Glu
1185                1190                1195                1200
Asp Gly Ala Asp Arg Val Val Leu Ala Gly Pro Asp Ala Pro Ala Gln
                1205                1210                1215
Ala Ala Ala Ala Gly Leu Thr Gly Val Ser Leu Val Pro Val Arg Cys
                    1220                1225                1230
Asp Val Thr Asp Arg Ala Ala Leu Ala Ala Leu Leu Asp Glu His Ala
        1235                1240                1245
Pro Thr Val Ala Val His Ala Pro Pro Leu Val Pro Leu Ala Pro Leu
    1250                1255                1260
Arg Glu Thr Ala Pro Gly Asp Ile Ala Ala Leu Ala Ala Lys Thr
1265                1270                1275                1280
Thr Ala Ala Gly His Leu Val Asp Leu Ala Pro Ala Ala Gly Leu Asp
                1285                1290                1295
Ala Leu Val Leu Phe Ser Ser Val Ser Gly Val Trp Gly Gly Ala Ala
                    1300                1305                1310
Gln Gly Gly Tyr Ala Ala Ala Ser Ala His Leu Asp Ala Leu Ala Glu
        1315                1320                1325
Arg Ala Arg Ala Ala Gly Val Pro Ala Phe Ser Val Ala Trp Ser Pro
    1330                1335                1340
Trp Ala Gly Gly Thr Pro Ala Asp Gly Ala Glu Ala Glu Phe Leu Ser
1345                1350                1355                1360
Arg Arg Gly Leu Ala Pro Leu Asp Pro Asp Gln Ala Val Arg Thr Leu
                1365                1370                1375
Arg Arg Met Leu Glu Arg Gly Ser Ala Cys Gly Ala Val Ala Asp Val
                    1380                1385                1390
Glu Trp Ser Arg Phe Ala Ala Ser Tyr Thr Trp Val Arg Pro Ala Val
        1395                1400                1405
Leu Phe Asp Asp Ile Pro Asp Val Gln Arg Leu Arg Ala Ala Glu Leu
    1410                1415                1420
Ala Pro Ser Thr Gly Asp Ser Thr Thr Ser Glu Leu Val Arg Glu Leu
1425                1430                1435                1440
Thr Ala Gln Ser Gly His Lys Arg His Ala Thr Leu Leu Arg Leu Val
                1445                1450                1455
Arg Ala His Ala Ala Ala Val Leu Gly Gln Ser Ser Gly Asp Ala Val
                    1460                1465                1470
```

-continued

```
Ser Ser Ala Arg Ala Phe Arg Asp Leu Gly Phe Asp Ser Leu Thr Ala
    1475                1480                1485

Leu Glu Leu Arg Asp Arg Leu Ser Thr Ser Thr Gly Leu Lys Leu Pro
    1490                1495                1500

Thr Ser Leu Val Phe Asp His Ser Ser Pro Ala Ala Leu Ala Arg His
1505                1510                1515                1520

Leu Gly Glu Glu Leu Leu Gly Arg Asn Asp Thr Ala Asp Arg Ala Gly
                1525                1530                1535

Pro Asp Thr Pro Val Arg Thr Asp Glu Pro Ile Ala Ile Gly Met
                1540                1545                1550

Ala Cys Arg Leu Pro Gly Gly Val Gln Ser Pro Glu Asp Leu Trp Asp
                1555                1560                1565

Leu Leu Thr Gly Gly Thr Asp Ala Ile Thr Pro Phe Pro Thr Asn Arg
    1570                1575                1580

Gly Trp Asp Asn Glu Thr Leu Tyr Asp Pro Asp Pro Asp Ser Pro Gly
1585                1590                1595                1600

His His Thr Tyr Val Arg Glu Gly Gly Phe Leu His Asp Ala Ala Glu
                1605                1610                1615

Phe Asp Pro Gly Phe Phe Gly Ile Ser Pro Arg Glu Ala Leu Ala Met
                1620                1625                1630

Asp Pro Gln Gln Arg Leu Ile Leu Glu Thr Ser Trp Glu Ser Phe Glu
                1635                1640                1645

Arg Ala Gly Ile Asp Pro Val Glu Leu Arg Gly Ser Arg Thr Gly Val
    1650                1655                1660

Phe Val Gly Thr Asn Gly Gln His Tyr Val Pro Leu Leu Gln Asp Gly
1665                1670                1675                1680

Asp Glu Asn Phe Asp Gly Tyr Ile Ala Thr Gly Asn Ser Ala Ser Val
                1685                1690                1695

Met Ser Gly Arg Leu Ser Tyr Val Phe Gly Leu Glu Gly Pro Ala Val
                1700                1705                1710

Thr Val Asp Thr Ala Cys Ser Ala Ser Leu Ala Ala Leu His Leu Ala
                1715                1720                1725

Val Gln Ser Leu Arg Arg Gly Glu Cys Asp Tyr Ala Leu Ala Gly Gly
    1730                1735                1740

Ala Thr Val Met Ser Thr Pro Glu Met Leu Val Glu Phe Ala Arg Gln
1745                1750                1755                1760

Arg Ala Val Ser Pro Asp Gly Arg Ser Lys Ala Phe Ala Glu Ala Ala
                1765                1770                1775

Asp Gly Val Gly Leu Ala Glu Gly Ala Gly Met Leu Leu Val Glu Arg
                1780                1785                1790

Leu Ser Glu Ala Gln Lys Lys Gly His Pro Val Leu Ala Val Val Arg
    1795                1800                1805

Gly Ser Ala Val Asn Gln Asp Gly Ala Ser Asn Gly Leu Thr Ala Pro
    1810                1815                1820

Ser Gly Pro Ala Gln Gln Arg Val Ile Arg Glu Ala Leu Ala Asp Ala
1825                1830                1835                1840

Gly Leu Thr Pro Ala Asp Val Asp Ala Val Glu Ala His Gly Thr Gly
                1845                1850                1855

Thr Pro Leu Gly Asp Pro Ile Glu Ala Gly Ala Leu Leu Ala Thr Tyr
                1860                1865                1870

Gly Arg Asp Arg Arg Asp Gly Pro Leu Trp Leu Gly Ser Leu Lys Ser
    1875                1880                1885

Asn Ile Gly His Thr Gln Ala Ala Ala Gly Val Ala Gly Val Ile Lys
    1890                1895                1900
```

```
Met Val Leu Ala Leu Arg His Gly Glu Leu Pro Arg Thr Leu His Ala
1905                1910                1915                1920

Ser Thr Ala Ser Ser Arg Ile Asp Trp Asp Ala Gly Ala Val Glu Leu
            1925                1930                1935

Leu Asp Glu Ala Arg Pro Trp Leu Gln Arg Ala Glu Gly Pro Arg Arg
                1940                1945                1950

Ala Gly Ile Ser Ser Phe Gly Ile Ser Gly Thr Asn Ala His Leu Val
            1955                1960                1965

Ile Glu Glu Pro Pro Glu Pro Thr Ala Pro Glu Leu Leu Ala Pro Glu
        1970                1975                1980

Pro Ala Ala Asp Gly Asp Val Trp Ser Glu Glu Trp Trp His Glu Val
1985                1990                1995                2000

Thr Val Pro Leu Met Met Ser Ala His Asn Glu Ala Ala Leu Arg Asp
                2005                2010                2015

Gln Ala Arg Arg Leu Arg Ala Asp Leu Leu Ala His Pro Glu Leu His
            2020                2025                2030

Pro Ala Asp Val Gly Tyr Thr Leu Ile Thr Thr Arg Thr Arg Phe Glu
            2035                2040                2045

Gln Arg Ala Ala Val Val Gly Glu Asn Phe Thr Glu Leu Ile Ala Ala
        2050                2055                2060

Leu Asp Asp Leu Val Glu Gly Arg Pro His Pro Leu Val Leu Arg Gly
2065                2070                2075                2080

Thr Ala Gly Thr Ser Asp Gln Val Val Phe Val Phe Pro Gly Gln Gly
            2085                2090                2095

Ser Gln Trp Pro Glu Met Ala Asp Gly Leu Leu Ala Arg Ser Ser Gly
            2100                2105                2110

Ser Gly Ser Phe Leu Glu Thr Ala Arg Ala Cys Asp Leu Ala Leu Arg
            2115                2120                2125

Pro His Leu Gly Trp Ser Val Leu Asp Val Leu Arg Arg Glu Pro Gly
            2130                2135                2140

Ala Pro Ser Leu Asp Arg Val Asp Val Val Gln Pro Val Leu Phe Thr
2145                2150                2155                2160

Met Met Val Ser Leu Ala Glu Thr Trp Arg Ser Leu Gly Val Glu Pro
                2165                2170                2175

Ala Ala Val Val Gly His Ser Gln Gly Glu Ile Ala Ala Ala Tyr Val
            2180                2185                2190

Ala Gly Ala Leu Thr Leu Asp Asp Ala Ala Arg Ile Val Ala Leu Arg
            2195                2200                2205

Ser Gln Ala Trp Leu Arg Leu Ala Gly Lys Gly Gly Met Val Ala Val
            2210                2215                2220

Thr Leu Ser Glu Arg Asp Leu Arg Pro Arg Leu Glu Pro Trp Ser Asp
2225                2230                2235                2240

Arg Leu Ala Val Ala Ala Val Asn Gly Pro Glu Thr Cys Ala Val Ser
                2245                2250                2255

Gly Asp Pro Asp Ala Leu Ala Glu Leu Val Ala Glu Leu Gly Ala Glu
            2260                2265                2270

Gly Val His Ala Arg Pro Ile Pro Gly Val Asp Thr Ala Gly His Ser
            2275                2280                2285

Pro Gln Val Asp Thr Leu Glu Ala His Leu Arg Lys Val Leu Ala Pro
        2290                2295                2300

Val Ala Pro Arg Thr Ser Asp Ile Pro Phe Tyr Ser Thr Val Thr Gly
2305                2310                2315                2320

Gly Leu Ile Asp Thr Ala Glu Leu Asp Ala Asp Tyr Trp Tyr Arg Asn
```

```
                    2325            2330            2335
Met Arg Glu Pro Val Glu Phe Glu Gln Ala Thr Arg Ala Leu Ile Ala
            2340            2345            2350

Asp Gly His Asp Val Phe Leu Glu Ser Ser Pro His Pro Met Leu Ala
            2355            2360            2365

Val Ser Leu Gln Glu Thr Ile Ser Asp Ala Gly Ser Pro Ala Ala Val
            2370            2375            2380

Leu Gly Thr Leu Arg Arg Gly Gln Gly Gly Pro Arg Trp Leu Gly Val
2385            2390            2395            2400

Ala Leu Cys Arg Ala Tyr Thr His Gly Leu Glu Ile Asp Ala Glu Ala
            2405            2410            2415

Ile Phe Gly Pro Asp Ser Arg Gln Val Glu Leu Pro Thr Tyr Pro Phe
            2420            2425            2430

Gln Arg Glu Arg Tyr Trp Tyr Ser Pro Gly His Arg Gly Asp Asp Pro
            2435            2440            2445

Ala Ser Leu Gly Leu Asp Ala Val Asp His Pro Leu Leu Gly Ser Gly
            2450            2455            2460

Val Glu Leu Pro Glu Ser Gly Asp Arg Met Tyr Thr Ala Arg Leu Gly
2465            2470            2475            2480

Ala Asp Thr Thr Pro Trp Leu Ala Asp His Ala Leu Leu Gly Ser Pro
            2485            2490            2495

Leu Leu Pro Gly Ala Ala Phe Ala Asp Leu Ala Leu Trp Ala Gly Arg
            2500            2505            2510

Gln Ala Gly Thr Gly Arg Val Glu Leu Thr Leu Ala Ala Pro Leu
            2515            2520            2525

Val Leu Pro Gly Ser Gly Gly Val Arg Leu Arg Leu Asn Val Gly Ala
            2530            2535            2540

Pro Gly Thr Asp Asp Ala Arg Arg Phe Ala Val His Ala Arg Ala Glu
2545            2550            2555            2560

Gly Ala Thr Asp Trp Thr Leu His Ala Glu Gly Leu Leu Thr Ala Gln
            2565            2570            2575

Asp Thr Ala Asp Ala Pro Asp Ala Ser Ala Ala Thr Pro Pro Pro Gly
            2580            2585            2590

Ala Glu Gln Leu Asp Ile Gly Asp Phe Tyr Gln Arg Phe Ser Glu Leu
            2595            2600            2605

Gly Tyr Gly Tyr Gly Pro Phe Phe Arg Gly Leu Val Ser Ala His Arg
            2610            2615            2620

Cys Gly Pro Asp Ile His Ala Glu Val Ala Leu Pro Val Gln Ala Gln
2625            2630            2635            2640

Gly Asp Ala Ala Arg Phe Gly Ile His Pro Ala Leu Leu Asp Ala Ala
            2645            2650            2655

Leu Gln Thr Met Ser Leu Gly Gly Phe Phe Pro Glu Asp Gly Arg Val
            2660            2665            2670

Arg Met Pro Phe Ala Leu Arg Gly Val Arg Leu Tyr Arg Ala Gly Ala
            2675            2680            2685

Asp Arg Leu His Val Arg Val Ser Pro Val Ser Glu Asp Ala Val Arg
            2690            2695            2700

Ile Arg Cys Ala Asp Gly Glu Gly Arg Pro Val Ala Glu Ile Glu Ser
2705            2710            2715            2720

Phe Ile Met Arg Pro Val Asp Pro Gly Gln Leu Leu Gly Gly Arg Pro
            2725            2730            2735

Val Gly Ala Asp Ala Leu Phe Arg Ile Ala Trp Arg Glu Leu Ala Ala
            2740            2745            2750
```

```
Gly Pro Gly Thr Arg Thr Gly Asp Gly Thr Pro Pro Val Arg Trp
        2755                2760            2765

Val Leu Ala Gly Pro Asp Ala Leu Gly Leu Ala Glu Ala Ala Asp Ala
        2770                2775            2780

His Leu Pro Ala Val Pro Gly Pro Asp Gly Ala Leu Pro Ser Pro Thr
2785                2790            2795                2800

Gly Arg Pro Ala Pro Asp Ala Val Val Phe Ala Val Arg Ala Gly Thr
            2805                2810            2815

Gly Asp Val Ala Ala Asp Ala His Thr Val Ala Cys Arg Val Leu Asp
            2820                2825            2830

Leu Val Gln Arg Arg Leu Ala Ala Pro Glu Gly Pro Asp Gly Ala Arg
            2835                2840            2845

Leu Val Val Ala Thr Arg Gly Ala Val Ala Val Arg Asp Asp Ala Glu
            2850                2855            2860

Val Asp Asp Pro Ala Ala Ala Ala Ala Trp Gly Leu Leu Arg Ser Ala
2865                2870            2875                2880

Gln Ala Glu Glu Pro Gly Arg Phe Leu Leu Val Asp Leu Asp Asp Asp
            2885                2890            2895

Pro Ala Ser Ala Arg Ala Leu Thr Asp Ala Leu Ala Ser Gly Glu Pro
            2900                2905            2910

Gln Thr Ala Val Arg Ala Gly Thr Val Tyr Val Pro Arg Leu Glu Arg
            2915                2920            2925

Ala Ala Asp Arg Thr Asp Gly Pro Leu Thr Pro Pro Asp Asp Gly Ala
            2930                2935            2940

Trp Arg Leu Gly Arg Gly Thr Asp Leu Thr Leu Asp Gly Leu Ala Leu
2945                2950            2955                2960

Val Pro Ala Pro Asp Ala Glu Ala Pro Leu Glu Pro Gly Gln Val Arg
            2965                2970            2975

Val Ala Val Arg Ala Ala Gly Val Asn Phe Arg Asp Ala Leu Ile Ala
            2980                2985            2990

Leu Gly Met Tyr Pro Gly Glu Ala Glu Met Gly Thr Glu Gly Ala Gly
            2995                3000            3005

Thr Val Val Glu Val Gly Pro Gly Val Thr Gly Val Ala Val Gly Asp
            3010                3015            3020

Arg Val Leu Gly Leu Trp Asp Gly Gly Leu Gly Pro Leu Cys Val Ala
3025                3030            3035                3040

Asp His Arg Leu Leu Ala Pro Val Pro Asp Gly Trp Ser Tyr Ala Gln
            3045                3050            3055

Ala Ala Ser Val Pro Ala Val Phe Leu Ser Ala Tyr Tyr Gly Leu Val
            3060                3065            3070

Thr Leu Ala Gly Leu Arg Pro Gly Glu Arg Val Leu Val His Ala Ala
            3075                3080            3085

Ala Gly Gly Val Gly Met Ala Ala Val Gln Ile Ala Arg His Leu Gly
            3090                3095            3100

Ala Glu Val Leu Ala Thr Ala Ser Pro Gly Lys Trp Asp Ala Leu Arg
3105                3110            3115                3120

Ala Met Gly Ile Thr Asp Asp His Leu Ala Ser Ser Arg Thr Leu Asp
            3125                3130            3135

Phe Ala Thr Ala Phe Thr Gly Ala Asp Gly Thr Ser Arg Ala Asp Val
            3140                3145            3150

Val Leu Asn Ser Leu Thr Lys Glu Phe Val Asp Ala Ser Leu Gly Leu
            3155                3160            3165

Leu Arg Pro Gly Gly Arg Phe Leu Glu Leu Gly Lys Thr Asp Val Arg
            3170                3175            3180
```

```
Asp Pro Glu Arg Ile Ala Ala Glu His Pro Gly Val Arg Tyr Arg Ala
3185                3190                3195                3200

Phe Asp Leu Asn Glu Ala Gly Pro Asp Ala Leu Gly Arg Leu Leu Arg
            3205                3210                3215

Glu Leu Met Asp Leu Phe Ala Ala Gly Val Leu His Pro Leu Pro Val
            3220                3225                3230

Val Thr His Asp Val Arg Arg Ala Ala Asp Ala Leu Arg Thr Ile Ser
            3235                3240                3245

Gln Ala Arg His Thr Gly Lys Leu Val Leu Thr Met Pro Pro Ala Trp
            3250                3255                3260

His Pro Tyr Gly Thr Val Leu Val Thr Gly Gly Thr Gly Ala Leu Gly
3265                3270                3275                3280

Ser Arg Ile Ala Arg His Leu Ala Ser Arg His Gly Val Arg Arg Leu
            3285                3290                3295

Leu Ile Ala Ala Arg Arg Gly Pro Asp Gly Glu Gly Ala Ala Glu Leu
            3300                3305                3310

Val Ala Asp Leu Ala Ala Leu Gly Ala Ser Ala Thr Val Val Ala Cys
            3315                3320                3325

Asp Val Ser Asp Ala Asp Ala Val Arg Gly Leu Leu Ala Gly Ile Pro
            3330                3335                3340

Ala Asp His Pro Leu Thr Ala Val Val His Ser Thr Gly Val Leu Asp
3345                3350                3355                3360

Asp Gly Val Leu Pro Gly Leu Thr Pro Glu Arg Met Arg Arg Val Leu
            3365                3370                3375

Arg Pro Lys Val Glu Ala Ala Val His Leu Asp Glu Leu Thr Arg Asp
            3380                3385                3390

Leu Asp Leu Ser Ala Phe Val Leu Phe Ser Ser Ala Gly Leu Leu
            3395                3400                3405

Gly Ser Pro Ala Gln Gly Asn Tyr Ala Ala Ala Asn Ala Thr Leu Asp
            3410                3415                3420

Ala Leu Ala Ala Arg Arg Arg Ser Leu Gly Leu Pro Ser Val Ser Leu
3425                3430                3435                3440

Ala Trp Gly Leu Trp Ser Asp Thr Ser Arg Met Ala His Ala Leu Asp
            3445                3450                3455

Gln Glu Ser Leu Gln Arg Arg Phe Ala Arg Ser Gly Phe Pro Pro Leu
            3460                3465                3470

Ser Ala Thr Leu Gly Ala Ala Leu Phe Asp Ala Ala Leu Arg Val Asp
            3475                3480                3485

Glu Ala Val Gln Val Pro Met Arg Phe Asp Pro Ala Ala Leu Arg Ala
            3490                3495                3500

Thr Gly Ser Val Pro Ala Leu Leu Ser Asp Leu Val Gly Ser Ala Pro
3505                3510                3515                3520

Ala Thr Gly Ser Ala Ala Pro Ala Ser Gly Pro Leu Pro Ala Pro Asp
            3525                3530                3535

Ala Gly Thr Val Gly Glu Pro Leu Ala Glu Arg Leu Ala Gly Leu Ser
            3540                3545                3550

Ala Glu Glu Arg His Asp Arg Leu Leu Gly Leu Val Gly Glu His Val
            3555                3560                3565

Ala Ala Val Leu Gly His Gly Ser Ala Ala Glu Val Arg Pro Asp Arg
            3570                3575                3580

Pro Phe Arg Glu Val Gly Phe Asp Ser Leu Thr Ala Val Glu Leu Arg
3585                3590                3595                3600

Asn Arg Met Ala Ala Val Thr Gly Val Arg Leu Pro Ala Thr Leu Val
```

```
                            3605                3610                3615
Phe Asp His Pro Thr Pro Ala Ala Leu Ser Ser His Leu Asp Gly Leu
                3620                3625                3630

Leu Ala Pro Ala Gln Pro Val Thr Thr Thr Pro Leu Leu Ser Glu Leu
                3635                3640                3645

Asp Arg Ile Glu Glu Ala Leu Ala Ala Leu Thr Pro Glu His Leu Ala
                3650                3655                3660

Glu Leu Ala Pro Ala Pro Asp Asp Arg Ala Glu Val Ala Leu Arg Leu
3665                3670                3675                3680

Asp Ala Leu Ala Asp Arg Trp Arg Ala Leu His Asp Gly Ala Pro Gly
                3685                3690                3695

Ala Asp Asp Asp Ile Thr Asp Val Leu Ser Ser Ala Asp Asp Asp Glu
                3700                3705                3710

Ile Phe Ala Phe Ile Asp Glu Arg Tyr Gly Thr Ser
                3715                3720
```

(2) INFORMATION FOR SEQ ID NO:5:

(i) SEQUENCE CHARACTERISTICS:
        (A) LENGTH: 1580 amino acids
        (B) TYPE: amino acid
        (D) TOPOLOGY: unknown (ii) MOLECULE TYPE: peptide (xi) SEQUENCE DESCRIPTION: SEQ ID NO:5:

```
Met Ala Asn Glu Glu Lys Leu Arg Ala Tyr Leu Lys Arg Val Thr Gly
1               5                   10                  15

Glu Leu His Arg Ala Thr Glu Gln Leu Arg Ala Leu Asp Arg Arg Ala
                20                  25                  30

His Glu Pro Ile Ala Ile Val Gly Ala Ala Cys Arg Leu Pro Gly Gly
                35                  40                  45

Val Glu Ser Pro Asp Asp Leu Trp Glu Leu Leu His Ala Gly Ala Asp
            50                  55                  60

Ala Val Gly Pro Ala Pro Ala Asp Arg Gly Trp Asp Val Glu Gly Arg
65                  70                  75                  80

Tyr Ser Pro Asp Pro Asp Thr Pro Gly Thr Ser Tyr Cys Arg Glu Gly
                85                  90                  95

Gly Phe Val Gln Gly Ala Asp Arg Phe Asp Pro Ala Leu Phe Gly Ile
                100                 105                 110

Ser Pro Asn Glu Ala Leu Thr Met Asp Pro Gln Gln Arg Leu Leu Leu
                115                 120                 125

Glu Thr Ser Trp Glu Ala Leu Glu Arg Ala Gly Leu Asp Pro Gln Ser
                130                 135                 140

Leu Ala Gly Ser Arg Thr Gly Val Phe Ala Gly Ala Trp Glu Ser Gly
145                 150                 155                 160

Tyr Gln Lys Gly Val Glu Gly Leu Glu Ala Asp Leu Glu Ala Gln Leu
                165                 170                 175

Leu Ala Gly Ile Val Ser Phe Thr Ala Gly Arg Val Ala Tyr Ala Leu
                180                 185                 190

Gly Leu Glu Gly Pro Ala Leu Thr Ile Asp Thr Ala Cys Ser Ser Ser
                195                 200                 205

Leu Val Ala Leu His Leu Ala Val Gln Ser Leu Arg Arg Gly Glu Cys
                210                 215                 220

Asp Leu Ala Leu Ala Gly Gly Ala Thr Val Ile Ala Asp Phe Ala Leu
225                 230                 235                 240
```

-continued

Phe Thr Gln Phe Ser Arg Gln Arg Gly Leu Ala Pro Asp Gly Arg Cys
            245                 250                 255

Lys Ala Phe Gly Glu Thr Ala Asp Gly Phe Gly Pro Ala Glu Gly Ala
            260                 265                 270

Gly Met Leu Leu Val Glu Arg Leu Ser Asp Ala Arg Arg Asn Gly His
            275                 280                 285

Pro Val Leu Ala Val Val Arg Gly Ser Ala Val Asn Gln Asp Gly Ala
290                     295                 300

Ser Asn Gly Leu Thr Ala Pro Ser Gly Pro Ala Gln Gln Arg Val Ile
305                 310                 315                 320

Arg Glu Ala Leu Ala Asp Ala Gly Leu Thr Pro Ala Asp Val Asp Ala
                325                 330                 335

Val Glu Ala His Gly Thr Gly Thr Pro Leu Gly Asp Pro Ile Glu Ala
                340                 345                 350

Gly Ala Leu Met Ala Thr Tyr Gly His Glu Arg Thr Gly Asp Pro Leu
            355                 360                 365

Trp Leu Gly Ser Leu Lys Ser Asn Ile Gly His Thr Gln Ala Ala Ala
            370                 375                 380

Gly Val Ala Gly Val Ile Lys Met Val Leu Ala Leu Arg His Gly Glu
385                 390                 395                 400

Leu Pro Arg Thr Leu His Ala Ser Thr Ala Ser Ser Arg Ile Glu Trp
                405                 410                 415

Asp Ala Gly Ala Val Glu Leu Leu Asp Glu Ala Arg Pro Trp Pro Arg
                420                 425                 430

Arg Ala Glu Gly Pro Arg Arg Ala Gly Ile Ser Ser Phe Gly Ile Ser
            435                 440                 445

Gly Thr Asn Ala His Leu Val Ile Glu Glu Pro Pro Ala Arg Pro
450                 455                 460

Glu Pro Glu Glu Ala Ala Gln Pro Pro Ala Pro Ala Thr Thr Val Leu
465                 470                 475                 480

Pro Leu Ser Ala Ala Gly Ala Arg Ser Leu Arg Glu Gln Ala Arg Arg
                485                 490                 495

Leu Ala Ala His Leu Ala Gly His Glu Glu Ile Thr Ala Ala Asp Ala
                500                 505                 510

Ala Arg Ser Ala Ala Thr Thr Arg Ala Ala Leu Ser His Arg Ala Ser
            515                 520                 525

Val Leu Ala Asp Asp Arg Arg Ala Leu Ile Asp Arg Leu Thr Ala Leu
530                 535                 540

Ala Glu Asp Arg Lys Asp Pro Gly Val Thr Val Gly Glu Ala Gly Ser
545                 550                 555                 560

Gly Arg Pro Pro Val Phe Val Phe Pro Gly Gln Gly Ser Gln Trp Thr
                565                 570                 575

Gly Met Gly Ala Glu Leu Leu Asp Arg Ala Pro Val Phe Arg Ala Lys
            580                 585                 590

Ala Glu Glu Cys Ala Arg Ala Leu Ala Ala His Leu Asp Trp Ser Val
            595                 600                 605

Leu Asp Val Leu Arg Asp Ala Pro Gly Ala Pro Ile Asp Arg Ala
610                 615                 620

Asp Val Val Gln Pro Thr Leu Phe Thr Met Met Val Ser Leu Ala Ala
625                 630                 635                 640

Leu Trp Glu Ser His Gly Val Arg Pro Ala Val Val Gly His Ser
                645                 650                 655

Gln Gly Glu Ile Ala Ala Ala His Ala Ala Gly Ala Leu Ser Leu Asp
                660                 665                 670

```
Asp Ala Ala Arg Val Ile Ala Glu Arg Ser Arg Leu Trp Lys Arg Leu
        675                 680                 685

Ala Gly Asn Gly Gly Met Leu Ser Val Met Ala Pro Ala Asp Arg Val
        690                 695                 700

Arg Glu Leu Met Glu Pro Trp Ala Glu Arg Met Ser Val Ala Ala Val
705                 710                 715                 720

Asn Gly Pro Ala Ser Val Thr Val Ala Gly Asp Ala Arg Ala Leu Glu
                725                 730                 735

Glu Phe Gly Gly Arg Leu Ser Ala Ala Gly Val Leu Arg Trp Pro Leu
                740                 745                 750

Ala Gly Val Asp Phe Ala Gly His Ser Pro Gln Val Glu Gln Phe Arg
        755                 760                 765

Ala Glu Leu Leu Asp Thr Leu Gly Thr Val Arg Pro Thr Ala Ala Arg
        770                 775                 780

Leu Pro Phe Phe Ser Thr Val Thr Ala Ala His Glu Pro Glu Gly
785                 790                 795                 800

Leu Asp Ala Ala Tyr Trp Tyr Arg Asn Met Arg Glu Pro Val Glu Phe
                805                 810                 815

Ala Ser Thr Leu Arg Thr Leu Leu Arg Glu Gly His Arg Thr Phe Val
        820                 825                 830

Glu Met Gly Pro His Pro Leu Leu Gly Ala Ala Ile Asp Glu Val Ala
        835                 840                 845

Glu Ala Glu Gly Val His Ala Thr Ala Leu Ala Thr Leu His Arg Gly
        850                 855                 860

Ser Gly Gly Leu Asp Arg Phe Arg Ser Ser Val Gly Ala Ala Phe Ala
865                 870                 875                 880

His Gly Val Arg Val Asp Trp Asp Ala Leu Phe Glu Gly Ser Gly Ala
                885                 890                 895

Arg Arg Val Pro Leu Pro Thr Tyr Ala Phe Ser Arg Asp Arg Tyr Trp
                900                 905                 910

Leu Pro Thr Ala Ile Gly Arg Arg Ala Val Glu Ala Ala Pro Val Asp
        915                 920                 925

Ala Ser Ala Pro Gly Arg Tyr Arg Val Thr Trp Thr Pro Val Ala Ser
        930                 935                 940

Asp Asp Ser Gly Arg Pro Ser Gly Arg Trp Leu Leu Val Gln Thr Pro
945                 950                 955                 960

Gly Thr Ala Pro Asp Glu Ala Asp Thr Ala Ala Ser Ala Leu Gly Ala
                965                 970                 975

Ala Gly Val Val Val Glu Arg Cys Leu Leu Asp Pro Thr Glu Ala Ala
        980                 985                 990

Arg Val Thr Leu Thr Glu Arg Leu Ala Glu Leu Asp Ala Gln Pro Glu
        995                 1000                1005

Gly Leu Ala Gly Val Leu Val Pro Gly Arg Pro Gln Ser Thr Ala
        1010                1015                1020

Pro Ala Asp Ala Ser Pro Leu Asp Pro Gly Thr Ala Ala Val Leu Leu
1025                1030                1035                1040

Val Val Gln Ala Val Pro Asp Ala Ala Pro Lys Ala Arg Ile Trp Val
                1045                1050                1055

Val Thr Arg Gly Ala Val Ala Val Gly Ser Gly Glu Val Pro Cys Ala
                1060                1065                1070

Val Gly Ala Arg Val Trp Gly Leu Gly Arg Val Ala Ala Leu Glu Val
        1075                1080                1085

Pro Val Gln Trp Gly Gly Leu Val Asp Val Ala Val Gly Ala Gly Val
```

-continued

```
         1090                1095                1100
Arg Glu Trp Arg Arg Val Val Gly Val Val Ala Gly Gly Glu Asp
1105                1110                1115                1120

Gln Val Ala Val Arg Gly Gly Gly Val Phe Gly Arg Arg Leu Val Gly
                        1125                1130                1135

Val Gly Val Arg Gly Gly Ser Gly Val Trp Arg Ala Arg Gly Cys Val
                1140                1145                1150

Val Val Thr Gly Gly Leu Gly Gly Val Gly Gly His Val Ala Arg Trp
            1155                1160                1165

Leu Ala Arg Ser Gly Ala Glu His Val Val Leu Ala Gly Arg Arg Gly
            1170                1175                1180

Gly Gly Val Val Gly Ala Val Glu Leu Glu Arg Glu Leu Val Gly Leu
1185                1190                1195                1200

Gly Ala Lys Val Thr Phe Val Ser Cys Asp Val Gly Asp Arg Ala Ser
                1205                1210                1215

Met Val Gly Leu Leu Gly Val Val Glu Gly Leu Gly Val Pro Leu Arg
            1220                1225                1230

Gly Val Phe His Ala Ala Gly Val Ala Gln Val Ser Gly Leu Gly Glu
            1235                1240                1245

Val Ser Leu Ala Glu Ala Gly Gly Val Leu Gly Gly Lys Ala Val Gly
1250                1255                1260

Ala Glu Leu Leu Asp Glu Leu Thr Ala Gly Val Glu Leu Asp Ala Phe
1265                1270                1275                1280

Val Leu Phe Ser Ser Gly Ala Gly Val Trp Gly Ser Gly Gly Gln Ser
                1285                1290                1295

Val Tyr Ala Ala Ala Asn Ala His Leu Asp Ala Leu Ala Glu Arg Arg
            1300                1305                1310

Arg Ala Gln Gly Arg Pro Ala Thr Ser Val Ala Trp Gly Leu Trp Gly
            1315                1320                1325

Gly Glu Gly Met Gly Ala Asp Glu Gly Val Thr Glu Phe Tyr Ala Glu
            1330                1335                1340

Arg Gly Leu Ala Pro Met Arg Pro Glu Ser Gly Ile Glu Ala Leu His
1345                1350                1355                1360

Thr Ala Leu Asn Glu Gly Asp Thr Cys Val Thr Val Ala Asp Ile Asp
                1365                1370                1375

Trp Glu His Phe Val Thr Gly Phe Thr Ala Tyr Arg Pro Ser Pro Leu
            1380                1385                1390

Ile Ser Asp Ile Pro Gln Val Arg Ala Leu Arg Thr Pro Glu Pro Thr
            1395                1400                1405

Val Asp Ala Ser Asp Gly Leu Arg Arg Arg Val Asp Ala Ala Leu Thr
            1410                1415                1420

Pro Arg Glu Arg Thr Lys Val Leu Val Asp Leu Val Arg Thr Val Ala
1425                1430                1435                1440

Ala Glu Val Leu Gly His Asp Gly Ile Gly Gly Ile His Asp Val
                1445                1450                1455

Ala Phe Arg Asp Leu Gly Phe Asp Ser Leu Ala Ala Val Arg Met Arg
            1460                1465                1470

Gly Arg Leu Ala Glu Ala Thr Gly Leu Val Leu Pro Ala Thr Val Ile
            1475                1480                1485

Phe Asp His Pro Thr Val Asp Arg Leu Gly Gly Ala Leu Leu Glu Arg
            1490                1495                1500

Leu Ser Ala Asp Glu Pro Ala Pro Gly Gly Ala Pro Glu Pro Ala Gly
1505                1510                1515                1520
```

```
Gly Arg Pro Ala Thr Pro Pro Ala Pro Glu Pro Ala Val His Asp
                1525                1530                1535

Ala Asp Ile Asp Glu Leu Asp Ala Asp Ala Leu Ile Arg Leu Ala Thr
            1540                1545                1550

Gly Thr Ala Gly Pro Ala Asp Gly Thr Pro Ala Asp Gly Gly Pro Asp
        1555                1560                1565

Ala Ala Ala Thr Ala Pro Asp Gly Ala Pro Glu Gln
    1570                1575                1580

(2) INFORMATION FOR SEQ ID NO:6:

(i) SEQUENCE CHARACTERISTICS:
        (A) LENGTH: 1891 amino acids
        (B) TYPE: amino acid
        (D) TOPOLOGY: unknown (ii) MOLECULE TYPE: peptide (xi) SEQUENCE DESCRIPTION: SEQ ID NO:6:

Met Ser Pro Ser Met Asp Glu Val Leu Gly Ala Leu Arg Thr Ser Val
1               5                   10                  15

Lys Glu Thr Glu Arg Leu Arg Arg His Asn Arg Glu Leu Leu Ala Gly
                20                  25                  30

Ala His Glu Pro Val Ala Ile Val Gly Met Ala Cys Arg Tyr Pro Gly
            35                  40                  45

Gly Val Ser Thr Pro Asp Asp Leu Trp Glu Leu Ala Ala Asp Gly Val
        50                  55                  60

Asp Ala Ile Thr Pro Phe Pro Ala Asp Arg Gly Trp Asp Glu Asp Ala
65                  70                  75                  80

Val Tyr Ser Pro Asp Pro Asp Thr Pro Gly Thr Thr Tyr Cys Arg Glu
                85                  90                  95

Gly Gly Phe Leu Thr Gly Ala Gly Asp Phe Asp Ala Ala Phe Phe Gly
            100                 105                 110

Ile Ser Pro Asn Glu Ala Leu Val Met Asp Pro Gln Gln Arg Leu Leu
        115                 120                 125

Leu Glu Thr Ser Trp Glu Thr Leu Glu Arg Ala Gly Ile Val Pro Ala
    130                 135                 140

Ser Leu Arg Gly Ser Arg Thr Gly Val Phe Val Gly Ala Ala His Thr
145                 150                 155                 160

Gly Tyr Val Thr Asp Thr Ala Arg Ala Pro Glu Gly Thr Glu Gly Tyr
                165                 170                 175

Leu Leu Thr Gly Asn Ala Asp Ala Val Met Ser Gly Arg Ile Ala Tyr
            180                 185                 190

Ser Leu Gly Leu Glu Gly Pro Ala Leu Thr Ile Gly Thr Ala Cys Ser
        195                 200                 205

Ser Ser Leu Val Ala Leu His Leu Ala Val Gln Ser Leu Arg Arg Gly
    210                 215                 220

Glu Cys Asp Leu Ala Leu Ala Gly Gly Val Ala Val Met Pro Asp Pro
225                 230                 235                 240

Thr Val Phe Val Glu Phe Ser Arg Gln Arg Gly Leu Ala Val Asp Gly
                245                 250                 255

Arg Cys Lys Ala Phe Ala Glu Gly Ala Asp Gly Thr Ala Trp Ala Glu
            260                 265                 270

Gly Val Gly Val Leu Leu Val Glu Arg Leu Ser Asp Ala Arg Arg Asn
        275                 280                 285

Gly His Arg Val Leu Ala Val Val Arg Gly Ser Ala Val Asn Gln Asp
    290                 295                 300
```

-continued

Gly Ala Ser Asn Gly Leu Thr Ala Pro Ser Gly Pro Ala Gln Gln Arg
305                 310                 315                 320

Val Ile Arg Glu Ala Leu Ala Asp Ala Gly Leu Thr Pro Ala Asp Val
            325                 330                 335

Asp Val Val Glu Ala His Gly Thr Gly Thr Ala Leu Gly Asp Pro Ile
            340                 345                 350

Glu Ala Gly Ala Leu Leu Ala Thr Tyr Gly Arg Glu Arg Val Gly Asp
        355                 360                 365

Pro Leu Trp Leu Gly Ser Leu Lys Ser Asn Ile Gly His Ala Gln Ala
    370                 375                 380

Ala Ala Gly Val Gly Val Ile Lys Val Val Gln Ala Met Arg His
385                 390                 395                 400

Gly Ser Leu Pro Arg Thr Leu His Val Asp Ala Pro Ser Ser Lys Val
                405                 410                 415

Glu Trp Ala Ser Gly Ala Val Glu Leu Leu Thr Glu Gly Arg Ser Trp
            420                 425                 430

Pro Arg Arg Val Glu Arg Val Arg Arg Ala Ala Val Ser Ala Phe Gly
            435                 440                 445

Val Ser Gly Thr Asn Ala His Val Val Leu Glu Glu Ala Pro Val Glu
450                 455                 460

Ala Gly Ser Glu His Gly Asp Gly Pro Gly Pro Asp Arg Pro Asp Ala
465                 470                 475                 480

Val Thr Gly Pro Leu Pro Trp Val Leu Ser Ala Arg Ser Arg Glu Ala
            485                 490                 495

Leu Arg Gly Gln Ala Gly Arg Leu Ala Ala Leu Ala Arg Gln Gly Arg
            500                 505                 510

Thr Glu Gly Thr Gly Gly Ser Gly Leu Val Val Pro Ala Ala Asp
        515                 520                 525

Ile Gly Tyr Ser Leu Ala Thr Thr Arg Glu Thr Leu Glu His Arg Ala
530                 535                 540

Val Ala Leu Val Gln Glu Asn Arg Thr Ala Gly Glu Asp Leu Ala Ala
545                 550                 555                 560

Leu Ala Ala Gly Arg Thr Pro Glu Ser Val Val Thr Gly Val Ala Arg
                565                 570                 575

Arg Gly Arg Gly Ile Ala Phe Leu Cys Ser Gly Gln Gly Ala Gln Arg
            580                 585                 590

Leu Gly Ala Gly Arg Glu Leu Arg Gly Arg Phe Pro Val Phe Ala Asp
        595                 600                 605

Ala Leu Asp Glu Ile Ala Ala Glu Phe Asp Ala His Leu Glu Arg Pro
610                 615                 620

Leu Leu Ser Val Met Phe Ala Glu Pro Ala Thr Pro Asp Ala Ala Leu
625                 630                 635                 640

Leu Asp Arg Thr Asp Tyr Thr Gln Pro Ala Leu Phe Ala Val Glu Thr
                645                 650                 655

Ala Leu Phe Arg Leu Leu Glu Ser Trp Gly Leu Val Pro Asp Val Leu
            660                 665                 670

Val Gly His Ser Ile Gly Gly Leu Val Ala Ala His Val Ala Gly Val
        675                 680                 685

Phe Ser Ala Ala Asp Ala Ala Arg Leu Val Ser Ala Arg Gly Arg Leu
    690                 695                 700

Met Arg Ala Leu Pro Glu Gly Gly Ala Met Ala Ala Val Gln Ala Thr
705                 710                 715                 720

Glu Arg Glu Ala Ala Ala Leu Glu Pro Val Ala Ala Gly Gly Ala Val

```
                    725                 730                 735
Val Ala Ala Val Asn Gly Pro Gln Ala Leu Val Leu Ser Gly Asp Glu
                740                 745                 750
Ala Ala Val Leu Ala Ala Gly Glu Leu Ala Arg Gly Arg Arg
            755                 760                 765
Thr Lys Arg Leu Arg Val Ser His Ala Phe His Ser Pro Arg Met Asp
        770                 775                 780
Ala Met Leu Ala Asp Phe Arg Ala Val Ala Asp Thr Val Asp Tyr His
785                 790                 795                 800
Ala Pro Arg Leu Pro Val Val Ser Glu Val Thr Gly Asp Leu Ala Asp
                805                 810                 815
Ala Ala Gln Leu Thr Asp Pro Gly Tyr Trp Thr Arg Gln Val Arg Gln
                820                 825                 830
Pro Val Arg Phe Ala Asp Ala Val Arg Thr Ala Ser Ala Arg Asp Ala
                835                 840                 845
Ala Thr Phe Ile Glu Leu Gly Pro Asp Ala Val Leu Cys Gly Met Ala
            850                 855                 860
Glu Glu Ser Leu Ala Ala Glu Ala Asp Val Val Phe Ala Pro Ala Leu
865                 870                 875                 880
Arg Arg Gly Arg Pro Glu Gly Asp Thr Val Leu Arg Ala Ala Ser
                885                 890                 895
Ala Tyr Val Arg Gly Ala Gly Leu Asp Trp Ala Ala Leu Tyr Gly Gly
                900                 905                 910
Thr Gly Ala Arg Arg Thr Asp Leu Pro Thr Tyr Ala Phe Gln His Ser
            915                 920                 925
Arg Tyr Trp Leu Ala Pro Ala Ser Ala Ala Val Ala Pro Ala Thr Ala
        930                 935                 940
Ala Pro Ser Val Arg Ser Val Pro Glu Ala Glu Gln Asp Gly Ala Leu
945                 950                 955                 960
Trp Ala Ala Val His Ala Gly Asp Val Ala Ser Ala Ala Arg Leu
                965                 970                 975
Gly Ala Asp Asp Ala Gly Ile Glu His Glu Leu Arg Ala Val Leu Pro
                980                 985                 990
His Leu Ala Ala Trp His Asp Arg Asp Arg Ala Thr Ala Arg Thr Ala
            995                 1000                1005
Gly Leu His Tyr Arg Val Thr Trp Gln Ala Ile Glu Ala Asp Ala Val
        1010                1015                1020
Arg Phe Ser Pro Ser Asp Arg Trp Leu Met Val Glu His Gly Gln His
1025                1030                1035                1040
Thr Glu Cys Ala Asp Ala Ala Glu Arg Ala Leu Arg Ala Ala Gly Ala
                1045                1050                1055
Glu Val Thr Arg Leu Val Trp Pro Leu Glu Gln His Thr Gly Ser Pro
                1060                1065                1070
Arg Thr Glu Thr Pro Asp Arg Gly Thr Leu Ala Ala Arg Leu Ala Glu
            1075                1080                1085
Leu Ala Arg Ser Pro Glu Gly Leu Ala Gly Val Leu Leu Pro Asp
                1090                1095                1100
Ser Gly Gly Ala Ala Val Ala Gly His Pro Gly Leu Asp Gln Gly Thr
1105                1110                1115                1120
Ala Ala Val Leu Leu Thr Ile Gln Ala Leu Thr Asp Ala Ala Val Arg
                1125                1130                1135
Ala Pro Leu Trp Val Val Thr Arg Gly Ala Val Ala Val Gly Ser Gly
                1140                1145                1150
```

Glu Val Pro Cys Ala Val Gly Ala Arg Val Trp Gly Leu Gly Arg Val
            1155                1160                1165

Ala Ala Leu Glu Val Pro Val Gln Trp Gly Gly Leu Val Asp Val Ala
1170                1175                1180

Val Gly Ala Gly Val Arg Glu Trp Arg Arg Val Val Gly Val Val Ala
1185                1190                1195                1200

Gly Gly Gly Glu Asp Gln Val Ala Arg Gly Gly Gly Val Phe Gly
            1205                1210                1215

Arg Arg Leu Val Gly Val Gly Val Arg Gly Gly Ser Gly Val Trp Arg
            1220                1225                1230

Ala Arg Gly Cys Val Val Val Thr Gly Gly Leu Gly Gly Val Gly Gly
            1235                1240                1245

His Val Ala Arg Trp Leu Ala Arg Ser Gly Ala Glu His Val Val Leu
            1250                1255                1260

Ala Gly Arg Arg Gly Gly Gly Val Val Gly Ala Val Glu Leu Glu Arg
1265                1270                1275                1280

Glu Leu Val Gly Leu Gly Ala Lys Val Thr Phe Val Ser Cys Asp Val
            1285                1290                1295

Gly Asp Arg Ala Ser Val Val Gly Leu Leu Gly Val Val Glu Gly Leu
            1300                1305                1310

Gly Val Pro Leu Arg Gly Val Phe His Ala Ala Gly Val Ala Gln Val
            1315                1320                1325

Ser Gly Leu Gly Glu Val Ser Leu Ala Glu Ala Gly Gly Val Leu Gly
            1330                1335                1340

Gly Lys Ala Val Gly Ala Glu Leu Leu Asp Glu Leu Thr Ala Gly Val
1345                1350                1355                1360

Glu Leu Asp Ala Phe Val Leu Phe Ser Ser Gly Ala Gly Val Trp Gly
            1365                1370                1375

Ser Gly Gly Gln Ser Val Tyr Ala Ala Ala Asn Ala His Leu Asp Ala
            1380                1385                1390

Leu Ala Glu Arg Arg Arg Ala Gln Gly Arg Pro Ala Thr Ser Val Ala
            1395                1400                1405

Trp Gly Pro Trp Asp Gly Asp Gly Met Gly Glu Met Ala Pro Glu Gly
            1410                1415                1420

Tyr Phe Ala Arg His Gly Val Ala Pro Leu His Pro Glu Thr Ala Leu
1425                1430                1435                1440

Thr Ala Leu His Gln Ala Ile Asp Gly Gly Glu Ala Thr Val Thr Val
            1445                1450                1455

Ala Asp Ile Asp Trp Glu Arg Phe Ala Pro Gly Phe Thr Ala Phe Arg
            1460                1465                1470

Pro Ser Pro Leu Ile Ala Gly Ile Pro Ala Ala Arg Thr Ala Pro Ala
            1475                1480                1485

Ala Gly Arg Pro Ala Glu Asp Thr Pro Thr Ala Pro Gly Leu Leu Arg
            1490                1495                1500

Ala Arg Pro Glu Asp Arg Pro Arg Leu Ala Leu Asp Leu Val Leu Arg
1505                1510                1515                1520

His Val Ala Ala Val Leu Gly His Ser Glu Asp Ala Arg Val Asp Ala
            1525                1530                1535

Arg Ala Pro Phe Arg Asp Leu Gly Phe Asp Ser Leu Ala Ala Val Arg
            1540                1545                1550

Leu Arg Arg Arg Leu Ala Glu Asp Thr Gly Leu Asp Leu Pro Gly Thr
            1555                1560                1565

Leu Val Phe Asp His Glu Asp Pro Thr Ala Leu Ala His His Leu Ala
            1570                1575                1580

-continued

```
Gly Leu Ala Asp Ala Gly Thr Pro Gly Pro Gln Glu Gly Thr Ala Arg
1585                1590                1595                1600

Ala Glu Ser Gly Leu Phe Ala Ser Phe Arg Ala Ala Val Glu Gln Arg
            1605                1610                1615

Arg Ser Ser Glu Val Val Glu Leu Met Ala Asp Leu Ala Ala Phe Arg
            1620                1625                1630

Pro Ala Tyr Ser Arg Gln His Pro Gly Ser Gly Arg Pro Ala Pro Val
            1635                1640                1645

Pro Leu Ala Thr Gly Pro Ala Thr Arg Pro Thr Leu Tyr Cys Cys Ala
        1650                1655                1660

Gly Thr Ala Val Gly Ser Gly Pro Ala Glu Tyr Val Pro Phe Ala Glu
1665                1670                1675                1680

Gly Leu Arg Gly Val Arg Glu Thr Val Ala Leu Pro Leu Ser Gly Phe
                1685                1690                1695

Gly Asp Pro Ala Glu Pro Met Pro Ala Ser Leu Asp Ala Leu Ile Glu
            1700                1705                1710

Val Gln Ala Asp Val Leu Leu Glu His Thr Ala Gly Lys Pro Phe Ala
            1715                1720                1725

Leu Ala Gly His Ser Ala Gly Ala Asn Ile Ala His Ala Leu Ala Ala
        1730                1735                1740

Arg Leu Glu Glu Arg Gly Ser Gly Pro Ala Ala Val Val Leu Met Asp
1745                1750                1755                1760

Val Tyr Arg Pro Glu Asp Pro Gly Ala Met Gly Glu Trp Arg Asp Asp
                1765                1770                1775

Leu Leu Ser Trp Ala Leu Glu Arg Ser Thr Val Pro Leu Glu Asp His
            1780                1785                1790

Arg Leu Thr Ala Met Ala Gly Tyr Gln Arg Leu Val Leu Gly Thr Arg
        1795                1800                1805

Leu Thr Ala Leu Glu Ala Pro Val Leu Leu Ala Arg Ala Ser Glu Pro
    1810                1815                1820

Leu Cys Ala Trp Pro Pro Ala Gly Gly Ala Arg Gly Asp Trp Arg Ser
1825                1830                1835                1840

Gln Val Pro Phe Ala Arg Thr Val Ala Asp Val Pro Gly Asn His Phe
                1845                1850                1855

Thr Met Leu Thr Glu His Ala Arg His Thr Ala Ser Leu Val His Glu
            1860                1865                1870

Trp Leu Asp Ser Leu Pro His Gln Pro Gly Pro Ala Pro Leu Thr Gly
        1875                1880                1885

Gly Lys His
    1890
```

PLATENOLIDE SYNTHASE GENE

This application claims the benefit of U.S. Provisional Application No. 60/012,050, filed Feb. 22, 1996.

BACKGROUND OF THE INVENTION

1. Field of the Invention

The present invention is directed to DNA molecules responsible for encoding the multi-functional proteins which direct the synthesis of the polyketide platenolide. The present invention also is directed to use of that DNA to produce compounds exhibiting antibiotic activity based on the platenolide structure, including specifically spiramycin and spiramycin analogues and derivatives.

2. Description of Related Art

Spiramycin is a macrolide antibiotic useful in both veterinary and human medicine produced by streptomycetes such as *Streptomyces ambofaciens* (ATCC 15154). Spiramycin is a 16-membered cyclic lactone, platenolide, with three attached sugar residues. Spiramycin's antibiotic activity is believed to be due to its inhibition of protein synthesis by a mechanism that involves binding of the antibiotic to a ribosome. Spiramycin is structurally similar to another antibiotic, tylosin, and the biosynthetic pathways of both are known to be similar.

The biosynthesis of tylosin has been thoroughly investigated (Baltz et al., *Antimicrobial Agents and Chemotherapy*, 20(2):214–225(1981); Beckmann et al., *Genetics and Molecular Biology of Industrial Microorganisms*, (1989) :176–186). Polyketides are synthesized via a common mechanistic scheme thought to be related to fatty acid synthesis. The cyclic lactone framework is prepared by a series of condensations involving small carboxylic acid residues. Modifications of the structure, such as ketoreduction, dehydration and enolylreduction, also occur during the processing. The synthesis is driven by a set of large multi-functional polypeptides, referred to as polyketide synthases.

PCT Publication WO 93/13663 describes the organization of the gene encoding the polyketide synthase of *Saccharapolyspora erythraea*. The gene is organized in modules, with each module effecting one condensation step. The precise sequence of chain growth and the processing of the growing chain is determined by the genetic information in each module. This PCT application describes an approach for synthesizing novel polyketide structures by manipulating in several ways the DNA governing the biosynthesis of the cyclic lactone framework. In order to adapt this methodology to other polyketides, however, the DNA molecules directing the biosynthetic processing must first be isolated.

The present invention is directed to the DNA sequence for the gene cluster responsible for encoding platenolide synthase, the building machinery of platenolide which is the basic building block of spiramycin. As a result, the present invention provides the information needed to synthesize novel spiramycin-related polyketides based on platenolide, arising from modifications of this DNA sequence designed to change the number and type of carboxylic acids incorporated into the growing polyketide chain and to change the kind of post-condensation processing that is conducted.

SUMMARY OF THE INVENTION

The present invention provides a DNA molecule comprising an isolated DNA sequence that encodes a platenolide synthase domain. Thus, the present invention provides the DNA molecule of SEQ ID NO:1 and DNA molecules that contain submodules thereof. The present invention also provides the products encoded by said DNA molecules, recombinant DNA expression vectors, and transformed microbial host cells. The present invention is further directed to a method of screening for new antibiotics based on the platenolide structure.

DETAILED DESCRIPTION OF THE INVENTION

Figure 1:
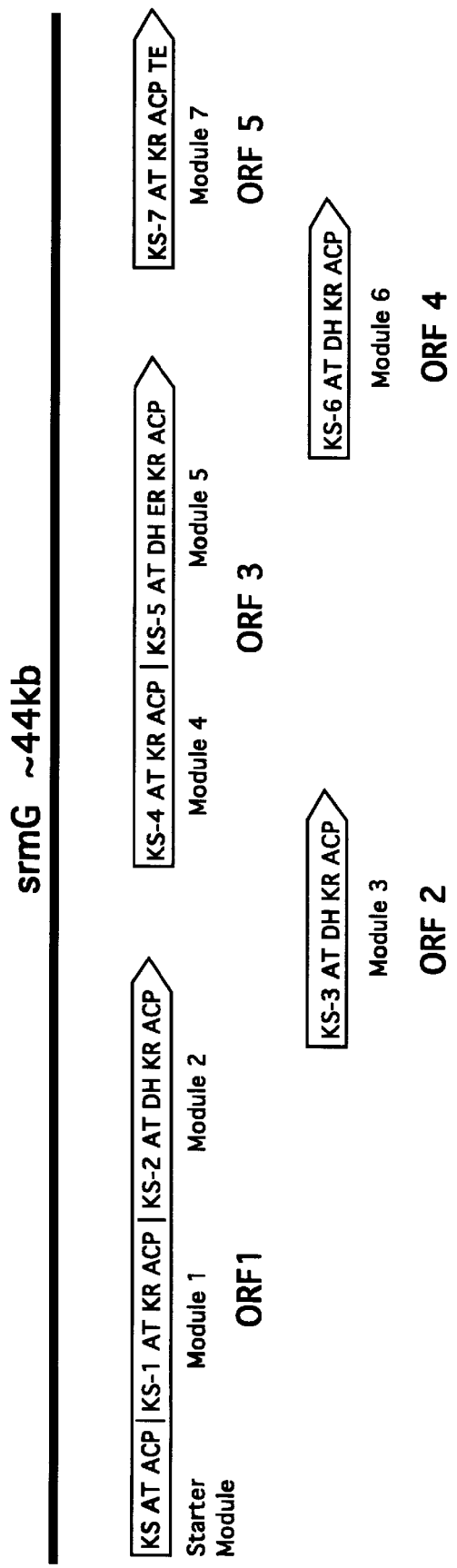
FIG. 1 shows the map of the srmg region of the *S. ambofaciens* DNA. Distances in kb are shown relative to the beginning of srmG. Open reading frames (ORF) are indicated by block arrows. The srmG DNA (0–42 kb) is the platenolide PKS region. The indicia Ap, G, E, K, P, and X denote restriction sites ApaI, BglII, EcoRI, KpnI, PstI and XhoI, respectively. Predicted domains for the srmG DNA are labeled as shown. ACP stands for acyl carrier protein; AT stands for acyltransferase; DH stands for dehydratase; ER stands for enoylreductase; KR stands for ketoreductase; KS stands for ketosynthase; and KS' stands for a ketosynthase-like domain in which a glutamine residue is present in the position occupied by an active site cysteine in a normal ketosynthase. KR' is a domain that resembles a ketoreductase but which is predicted to be inactive.

The term polyketide defines a class of molecules produced through the successive condensation of small carboxylic acids. This diverse group includes plant flavonoids, fungal aflatoxins, and hundreds of compounds of different structures that exhibit antibacterial, antifungal, antitumor, and anthelmintic properties. Some polyketides produced by fungi and bacteria are associated with sporulation or other developmental pathways; others do not yet have an ascribed function. Some polyketides have more than one pharmacological effect. The diversity of polyketide structures reflects the wide variety of their biological properties. Many cyclized polyketides undergo glycosidation at one or more sites, and virtually all are modified during their synthesis through hydroxylation, reduction, epoxidation, etc.

A common feature of compounds in this class is that their synthesis is directed by a complex of multi-functional peptides, termed a "polyketide synthase". Molecular genetic analysis of polyketide synthase genes has revealed two distinct classes of enzymes operating for different polyketides: (a) the aromatics, which are made through an essentially iterative process; (b) the complex polyketides, which comprise several repeats of the same activities arranged in few, very large polypeptides. A common feature among complex polyketide synthase genes is that they are generally arranged in several open reading frames (ORFs), each of which contains one or more repeated units, designated modules. Each module processes one condensation step and typically requires several activities accomplished by several enzymes including acyl carrier protein (ACP), β-ketosynthase (KS), and acyltransferase (AT).

Therefore a "module" is defined as the genetic element encoding a multi-functional protein segment that is responsible for all of the distinct activities required in a single round of synthesis, i.e., one condensation step and all the β-carbonyl processing steps associated therewith. Each module encodes an ACP, a KS, and an AT activity to accomplish the condensation portion of the synthesis, and selected post-condensation activities to effect β-carbonyl processing. Each module is therefore, further characterized by the inclusion of submodules that are responsible for encoding the distinct activities of a complex polyketide synthase. A "submodule" thus is defined as the portion of the polyketide synthase DNA sequence that encodes a distinct activity, or "domain". A distinct activity or domain is commonly understood to mean that part of the polyketide synthase polyprotein necessary for a given distinct activity.

The protein segments corresponding to each module are called synthase units (SUs). Each SU is responsible for one of the fatty acid-like cycles required for completing the polyketide; it carries the elements required for the condensation process, for selecting the particular extender unit (a coenzyme A thioester of a dicarboxylate) to be incorporated, and for the extent of processing that the β-carbon will undergo. After completion of the cycle, the nascent polyketide is transferred from the ACP it occupies to the KS of the next SU utilized, where the appropriate extender unit and processing level are introduced. This process is repeated, employing a new SU for each elongation cycle, until the programmed length has been reached. As in synthesis, of long chain fatty acids, the number of elongation cycles determines the length of the molecule. However, whereas fatty acid synthesis involves a single SU used iteratively, formation of complex polyketides requires participation of a different SU for each cycle, thereby ensuring that the correct molecular structure is produced.

The composition of the polyketide synthase gene modules are variable. Some carry the full complement of β-ketoreductase(KR), dehydratase(DH), and enoylreductase (ER) domains, and some encode a particular domain only or lack a functional domain, although much of the sequence is preserved.

This variable composition of the modules, which correlate with the asymmetry in the synthesis of the polyketide precursor, enable a specific step to be assigned to each module. Since each enzymatic activity is involved in a single biochemical step in the pathway, loss of any one activity should affect only a single step in the synthesis. Knowledge of the correlation between the structure of the polyketide and the organization of the polyketide synthase genes enables one to produce altered genes selectively which produce a polyketide derivative with predicted structure.

Because the degree of processing appears to depend on the presence of functional domains in a particular SU, inactivation of a KR, DH, or ER will result in a polyketide less processed at a single site, but only if the altered chain thus produced can be utilized as a substrate for the subsequent synthesis steps. Thus, the inactivation of one of these domains should result in the formation of a polyketide retaining a ketone, hydroxyl, or site of unsaturation at the corresponding position. This rationale has led to the successful production of altered erythromycin derivatives from strains in which a KR or an ER domain had been inactivated.

Thus, one can engineer polyketide pathways by genetic intervention of the polyketide synthase and by adding or eliminating modification steps. Many of the enzymes involved in postpolyketide modifications do not seem to have absolute specificity for a particular structure. In addition one can also select the desired components from a library of polyketide and postpolyketide biosynthesis genes and combine them to produce novel structures.

The present invention provides, in particular, the DNA sequence encoding the polyketide synthase responsible for biosynthesis of platenolide, i.e., platenolide synthase. Platenolicle itself is the foundation for spiramycin-related polyketides. The platenolide synthase DNA sequence, which defines the platenolide synthase gene cluster, directs biosynthesis of the platenolide polyketide by encoding the various distinct activities of platenolide synthase.

Figure 2:
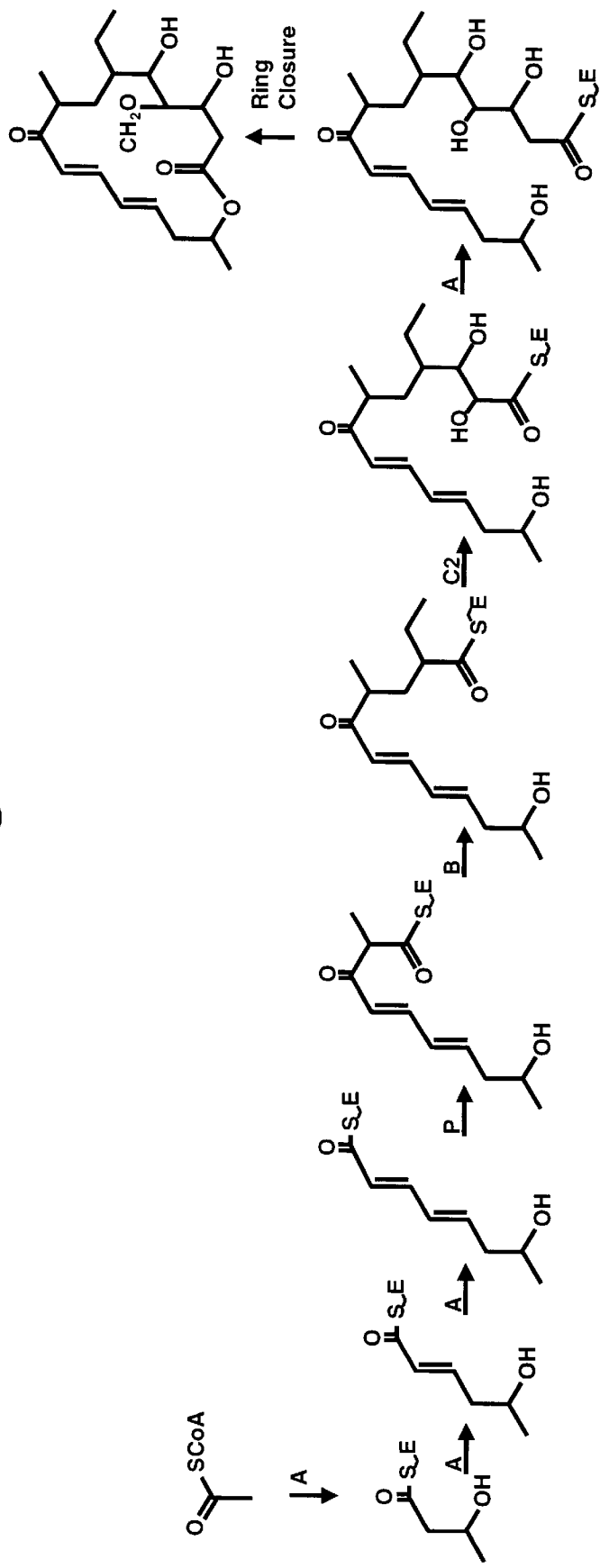
FIG. 2 demonstrates the biosynthetic pathway for platenolide synthesis. A denotes malonyl-CoA; B denotes ethylmalcnyl-CoA; P denotes methylmalonyl-CoA; C2 denotes a CoA derivative related to malonyl-CoA but of unknown structure.

The gene cluster for platenolide synthase, like other polyketide biosynthetic genes whose organization has been elucidated, is characterized by the presence of several ORFs, each of which contains one or more repeated units termed modules as defined above. Each module also further includes submodules as defined above. Organization of the platenolide synthase gene cluster derived from *Streptomyces ambofaciens* is shown in FIG. 2. The accompanying synthetic pathway and the specific carboxylic acid substrates that are used for each condensation reaction and the post-condensation activities of platenolide synthesis are indicated in FIG. 1.

A preferred DNA molecule comprising the platenolide synthase gene cluster isolated from *Streptomyces ambofaciens* is represented by SEQ ID NO: 1. Other preferred DNA molecules of the present invention include the various ORFS of SEQ ID NO: 1 that encode individual multi-functional polypeptides. These are represented by ORF1, 350 to 14002, ORF2, 14046 to 20036, ORF3, 20110 to 31284, ORF4, 31329 to 36071, and ORF5, 36155 to 41830 all in SEQ ID NO: 1. The predicted amino acid sequences of the various peptides encoded by these sequences are shown in SEQ ID NO: 2, 3, 4, 5, and 6.

Yet other preferred DNA molecules of the present invention include the modules that encode all the activities necessary for a single round of synthesis. These are represented by starter module 392 to 3424, module 1, 3527 to 8197, module 2, 8270 to 13720, module 3, 14148 to 19730, module 4, 20215 to 24678, module 5, 24742 to 31002, module 6, 31428 to 35837, and module 7, 36257 to 41395 all in SEQ ID NO: 1. The predicted amino acid sequences of the various synthase units encoded by these modules are represented by starter SU 15 to 1025, SU1, 1060 to 2616, and SU2, 2641 to 4457 in SEQ ID NO: 2; SU3, 35 to 1895 in SEQ ID NO: 3; SU4, 36 to 1523, and SU5, 1545 to 3631 in SEQ ID NO: 4; SU6, 34 to 1503 in SEQ ID NO: 5; SU7, 35 to 1747 all in SEQ ID NO: 6.

Still other preferred DNA molecules include the various submodules that encode the various domains of platenolide synthase. These submodules are represented by KS'(s), 392 to 1603, AT(s), 1922 to 2995, and ACP(s), 3173 to 3424 of starter module in SEQ ID NO:1; KS1, 3527 to 4798, AT1, 5135 to 6208, KR1, 7043 to 7597, and ACP1, 7946 to 8197 of module 1 in SEQ ID NO: 1; KS2, 8270 to 9541, AT2, 9899 to 10909, DH2, 10985 to 11530, KR2, 12596 to 13153, and ACP2, 13469 to 13720 of module 2 in SEQ ID NO: 1; KS3, 14148 to 15422, AT3, 15789 to 16844, DH3, 16914 to 17510, KR3, 18612 to 19166, and ACP3, 19479 to 19730 of module 3 in SEQ ID NO: 1; KS4, 20215 to 21486, AT4, 21889 to 22872, KR'4, 23638 to 24159, and ACP4, 24484 to 24678 of module 4 in SEQ ID NO: 1; KS5, 24742 to 26016, AT5, 26371 to 27381, DH5, 27442 to 27966, ER5, 28843 to 29892, KR5, 29905 to 30462, and ACP5, 30760 to 31002 of module 5 in SEQ ID NO: 1; KS6, 31428 to 32696, AT6, 33024 to 34022, KR6, 34770 to 35327, and ACP6, 35586 to 35837 of module 6 in SEQ ID NO: 1; KS7, 36257 to 37528, AT7, 37898 to 38905, KR7, 39851 to 40408, ACP7, 40658 to 40909, and TE, 41297 to 41395 of module 7 in SEQ ID NO: 1. The predicted amino acid sequences of the various domains encoded by these submodules are represented by KS'(s), 15 to 418, AT(s), 525 to 882, and ACP(s), 942 to 1025 of starter SU in SEQ ID NO:2; KS1, 1060 to 1483, AT1, 1596 to 1953, KR1, 2232 to 2416, and ACP1, 2533 to 2616 of SU1 in SEQ ID NO: 2; KS2, 2641 to 3064, AT2, 3184 to 3520, DH2, 3546 to 3727, KR2, 4083 to 4268, and ACP2, 4374 to 4457 of SU2 in SEQ ID NO: 2; KS3, 35 to 459, AT3, 582 to 933, DH3, 957 to 1155, KR3, 1523 to 1707, and ACP3, 1812 to 1895 of SU3 in SEQ ID NO: 3; KS4, 36 to 459, AT4, 594 to 921, $KS^04$, 1177 to 1350, and ACP4, 1459 to 1523 of SU4 in SEQ ID NO: 4; KS5, 1545 to 1969, AT5, 2088 to 2424, DH5, 2445 to 2619, ER5, 2912 to 3261, KR5, 3266 to 3451, and ACP5, 3551 to 3631 of SU5 in SEQ ID NO: 4; KS6, 34 to 456, AT6, 566 to 898, KR6, 1148 to 1333, and ACP6, 1420 to 1503 of SU6 in SEQ ID NO: 5; KS7, 35 to 458, AT7, 582 to 917, KR7, 1233 to 1418, ACP7, 1502 to 1585, and TE, 1715 to 1747 of SU7 in SEQ ID NO: 6.

Although not wishing to be bound to any particular technical explanation, a sequence similarity exists among domain boundaries in various polyketide synthase genes. Thus, one skilled in the art is able to predict the domain boundaries of newly discovered polyketide synthase genes based on the sequence information of known polyketide synthase genes. In particular, the boundaries of submodules, domains, and open reading frames in the instant application are predicted based on sequence information disclosed in this application and the locations of the domain boundaries of the erythromycin polyketide synthase (Donadio et al., *GENE*, 111 51–60 (1992)). Furthermore, the genetic organization of the platenolide synthase gene cluster appears to correspond to the order of the reactions required to complete synthesis of platenolide. This means that the polyketide synthase DNA sequence can be manipulated to generate predictable alterations in the final platenolide product.

The DNA sequence of the platenolide synthase gene can be determined from recombinant DNA clones prepared from the DNA of *Streptomyces ambofaciens*, in particular strain ATCC 15154. The platenolide synthase gene endogenous to *Streptomyces ambofaciens* (ATCC 15154) is contained in recombinant DNA vectors pKC1080 and pKC1306 (FIG. 2), which are freely available for the duration of the patent term from the National Center for Agricultural Utilization Research, 1815 North University Street, Peoria, Ill. 61604-3999, in *E. coli* DH10B under accession numbers B-21500 for pKC1080 (deposited Sep. 21, 1995) and B-21499 for pKC1306 (deposited Sep. 21, 1995) respectively.

Techniques of isolating bacterial DNA are readily available and well known in the art. Any such techniques can be employed in this invention. In particular DNA from these deposited cultures can be isolated as follows. Lyophils of *E. coli* DH10B/pKC1080 or *E. coli* DH10B/pKC1306 are plated onto L-agar (10 g tryptone, 10 g NaCl, 5 g yeast extract, and 15 g agar per liter) plates containing 100 µg/ml apramycin to obtain a single colony isolate of the strain. This colony is used to inoculate about 500 ml of L-broth (10 g tryptone, 10 g NaCl, 5 g yeast extract per liter) containing 100 µg/ml apramycin, and the resulting culture is incubated at 37° C. with aeration until the cells reach stationary phase. Cosmid DNA can be obtained from the cells in accordance with procedures known in the art (see e.g., Rao et al., 1987 in Methods in Enzymology, 153:166).

DNA of the current invention can be sequenced using any known techniques in the art such as the dideoxynucleotide chain-termination method (Sanger, et al., Proc. Natl. Acad. Sci. 74:5463 (1977)) with either radioisotopic or fluorescent labels. Double-stranded, supercoiled DNA can be used directly for templates in sequence reactions with sequence-specific oligonucleotide primers. Alternatively, fragments can be used to prepare libraries of either random, overlapping sequences in the bacteriophage M13 or nested, overlapping deletions in a plasmid vector. Individual recombinant DNA subclones are then sequenced with vector-specific oligonucleotide primers. Radioactive reaction products are electrophoresed on denaturing polyacrylamide gels and analyzed by autoradiography. Fluorescently labeled reaction products are electrophoresed and analyzed on Applied Biosystems (ABI Division, Perkin Elmer, Foster City, Calif. 94404) model 370A and 373A or Dupont (Wilmington, Del.) Genesis DNA sequencers. Sequence data are assembled and edited using Genetic Center Group (GCG, Madison, Wis.) programs GelAssemble and Seqed or the ABI model 670 Inherit Sequence Analysis system and the AutoAssembler and SeqEd programs.

Polypeptides corresponding to a domain, a submodule, a module, a synthesis unit (SU), or an open reading frame can be produced by transforming a host cell such as bacteria, yeast, or eukaryotic cell-expression system with the cDNA sequence in a recombinant DNA vector. It is well within one skilled in the art to choose among host cells and numerous recombinant DNA expression vectors to practice the instant invention. Multifunctional polypeptides of polyketide platenolide synthase can be extracted from platenolide-producing bacteria such as *Streptomyces ambofaciens* or translated in a cell-free in vitro translation system. In addition, the techniques of synthetic chemistry can be employed to synthesize some of the polypeptides mentioned above.

Procedures and techniques for isolation and purification of proteins produced in recombinant host cells are known in the art. See, for example, Roberts et al., Eur. J. Biochem. 214, 305–311, (1993) and Caffrey et al., FEBS 304, 225–228 (1992) for detailed description of polyketide synthase purification in bacteria. To achieve a homogeneous preparation of a polypeptide, proteins in the crude cell extract can be separated by size and/or charge through different columns well known in the art once or several times. In particular the crude cell extract can be applied to various cellulose columns commercially available such as DEAE-cellulose columns. Subsequently the bound proteins can be eluted and the fractions can be tested for the presence of the polyketide platenolide synthase or engineered derivative protein. Techniques for detecting the target protein are readily available in the art. Any such techniques can be employed for this invention. In particular the fractions can be analysized on Western blot using antibodies raised against a portion or portions of such polyketide platenolide synthase proteins. The fractions containing the polyketide platenolide synthase protein can be pooled and further purified by passing through more columns well known in the art such as applying the pooled fractions to a gel filtration column. When visualized on SDS-PAGE gels homogeneous preparations contain a single band and are substantially free of other proteins.

Knowledge of the platenolide synthase DNA sequence, its genetic organization, and the activities associated with particular open reading frames, modules, and submodules of the gene enables production of novel polyketides having a predicted structure that are not otherwise available. Modifications may be made to the DNA sequence that either alter the initial carboxylic acid building block used or alter the building block added at any of the condensation steps. The platenolide synthase gene may also be modified to alter the actual number of condensation steps done, thereby changing the size of the carbon backbone. Submodules that are part of the present invention may be selectively inactivated thereby giving rise to predictable, novel polyketide structures. Modifications to portions of the DNA sequence that encode the post-condensation processing activities will alter the functional groups appearing at the various condensation sites on the carbon chain backbone.

One skilled in the art is fully familiar with the degeneracy of the genetic code. Consequently, the skilled artisan can modify the specific DNA sequences provided by this disclosure to provide proteins having the same or improved characteristics compared to those polypeptides specifically provided herein. Also, one skilled in the art can modify the DNA sequences to express an identical protein to those provided, albeit expressed at higher levels. Furthermore, one skilled in the art is familiar with means to prepare synthetically, either partially, or in whole, DNA sequences which would be useful in preparing recombinant DNA vectors or coding sequences which are encompassed by the current invention. Additionally, recombinant means for modifying the DNA sequences provided may include for example site-directed deletion or site-directed mutagenesis. These techniques are well known to those skilled in the art and require no further elaboration here. Consequently, as used herein, DNA which is isolated from natural sources, prepared synthetically or semi-synthetically, or which are modified by recombinant DNA methods, are within the scope of the present invention.

Likewise, those skilled in the art will recognize that the polypeptides of the invention may be expressed recombinantly. Alternatively, these polypeptides may be synthesized as well, either in whole or in part, by conventional known non-recombinant techniques; for example, solid-phase synthesis. Thus, the present invention should not be construed as necessarily limited to any specific vector constructions or means for production of the specific polyketide synthase molecules exemplified. These alternate means for preparing the present polypeptides are meant to be encompassed by the present invention.

Many cyclized polyketides undergo glycosidation at one or more sites. Spiramycin is a 16-membered cyclic lactone, platenolide, with three attached sugar residues. The process of converting platenolide to spiramycin is well known in the art. The present invention also provides the information needed to synthesize novel spiramycin-related polyketides based on platenolide. The principles have already been described above. In addition, any product resulting from post-transcriptional or post-translational modification in vivo or in vitro based on the DNA sequence information disclosed here are meant to be encompassed by the present invention.

The following example is provided for exemplification purposes only and is not intended to limit the scope of the invention which has been described in broad terms above.

EXAMPLE 1

Figure 3:
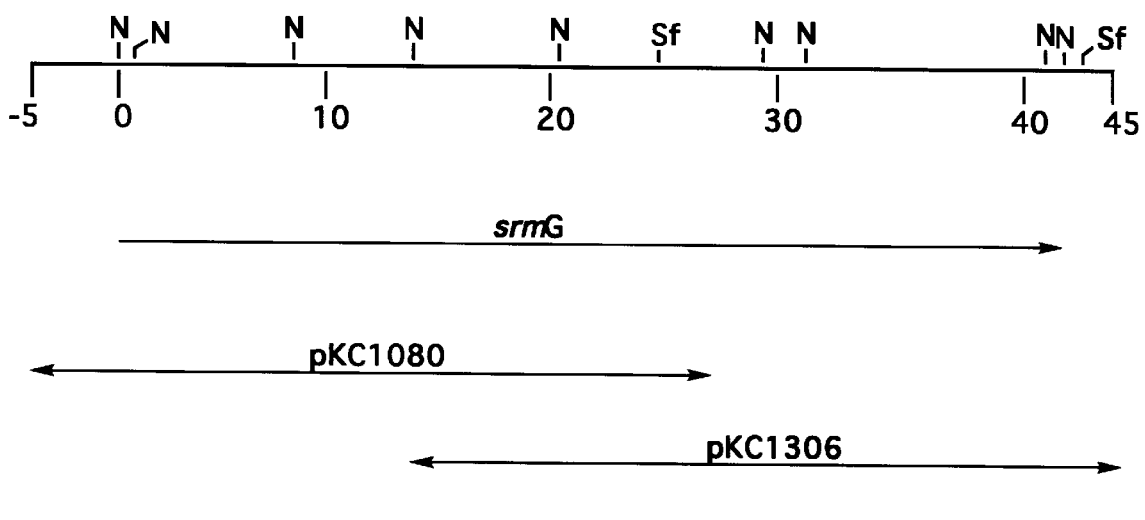
FIG. 3 shows the map of two clones that span the whole region of the srmG DNA.

Specific Experimental Details and Results from the Sequencing of Platenolide Synthase The DNA sequence of the *S. ambofaciens* platenolide synthase (srmG) gene can be obtained by sequencing inserts of recombinant DNA subclones containing contiguous or overlapping DNA segments of the region indicated in FIG. 3. All sequences representing srmG are fully contained in the overlapping cosmid clones pKC1080 and pKC1306 (FIG. 3). The sequence can be obtained by subcloning and sequencing the fragments bounded by NruI sites at position 1, 0.3 kb, 8.2 kb, 14.1 kb, 20.2 kb, 29.5 kb, 31.4 kb, 41.1 kb and 42.0 kb. In order to obtain the srmG region on a single fragment, the 25.0 kb fragment bounded by the NruI site at position 1 and the SfuI site at 25.0 kb should be isolated from a partial digestion of pKC1080 with restriction enzymes NruI and SfuI. The 17.8 kb DNA fragment bounded by the SfuI sites at 25.0 kb and 42.8 kb should be isolated from a digestion of pKC1306 with the restriction enzyme SfuI. The resulting fragments should be ligated and cloned in an appropriate recombinant DNA vector. Clones containing the correct orientation of the two ligated fragments can be identified by restriction enzyme site mapping.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. An isolated DNA molecule comprising a nucleotide sequence that encodes a polypeptide comprising a platenolide synthase domain.

2. An isolated DNA molecule comprising a nucleotide sequence that encodes a polypeptide comprising a platenolide synthase domain endogenous to a platenolide-producing organism.

3. An isolated DNA molecule comprising a nucleotide sequence that encodes a polypeptide comprising a platenolide synthase domain endogenous to a spiramycin-producing organism.

4. An isolated DNA molecule comprising a nucleotide sequence that encodes a polypeptide comprising a platenolide synthase domain endogenous to a Streptomycete.

5. An isolated DNA molecule comprising a nucleotide sequence that encodes a polypeptide comprising a platenolide synthase domain endogenous to Streptomyces ambofaciens.

6. The isolated DNA molecule of claim 2 wherein the nucleotide sequence is selected from the group consisting of: nucleotides 392 to 1603, 1922 to 2995, 3173 to 3424, 3527 to 4798, 5135 to 6208, 7043 to 7597, 7946 to 8197, 8270 to 9541, 9899 to 10909, 10985 to 11530, 12596 to 13153, 13469 to 13720, 14148 to 15422, 15789 to 16844, 16914 to 17510, 18612 to 19166, 19479 to 19730, 20215 to 21486, 21889 to 22872, 23638 to 24159, 24484 to 24678, 24742 to 26016, 26371 to 27381, 27442 to 27966, 28843 to 29892, 29905 to 30462, 30760 to 31002, 31428 to 32696, 33024 to 34022, 34770 to 35327, 35586 to 35837, 36257 to 37528, 37898 to 38905, 39851 to 40408, 40658 to 40909, and 41297 to 41395 all in SEQ ID NO: 1.

7. The isolated DNA molecule of claim 2 wherein the nucleotide sequence is selected from the group consisting of:

nucleotides 392 to 3424, 3527 to 8197, 8270 to 13720, 14148 to 19730, 20215 to 24678, 24742 to 31002, 31428 to 35837, and 36257 to 41395 all in SEQ ID NO: 1.

8. The isolated DNA molecule of claim 2 wherein the nucleotide sequence is selected from the group consisting of:

nucleotides 350 to 14002, 14046 to 20036, 20110 to 31284, 31329 to 36071, and 36155 to 41830 all in SEQ ID NO: 1.

9. An isolated DNA molecule consisting of nucleotide sequence of SEQ ID NO: 1.

10. A recombinant DNA vector comprising the DNA molecule of claim 2.

11. A recombinant DNA vector comprising the DNA molecule of claim 6.

12. A recombinant DNA vector comprising the DNA molecule of claim 7.

13. A recombinant DNA vector comprising the DNA molecule of claim 8.

14. A recombinant DNA vector comprising the DNA molecule of claim 9.

15. The recombinant DNA vector deposited under accession number NRRL B-21500.

16. The recombinant DNA vector deposited under accession number NRRL B-21499.

17. A host cell transformed with a recombinant DNA vector of claim 10.

18. A host cell transformed with a recombinant DNA vector of claim 11.

19. A host cell transformed with a recombinant DNA vector of claim 12.

20. A host cell transformed with a recombinant DNA vector of claim 13.

21. A host cell transformed with a recombinant DNA vector of claim 14.

22. An isolated polypeptide comprising an amino acid sequence wherein said polypeptide comprises a platenolide synthase domain.

23. An isolated polypeptide of claim 22 wherein the amino acid sequence is selected from the group consisting of:

(a) amino acids 15 to 418, 525 to 882, 942 to 1025, 1060 to 1483, 1596 to 1953, 2232 to 2416, 2533 to 2616, 2641 to 3064, 3184 to 3520, 3546 to 3727, 4083 to 4268, and 4374 to 4457 all in SEQ ID NO: 2;

(b) amino acids 35 to 459, 582 to 933, 957 to 1155, 1523 to 1707, and 1812 to 1895 all in SEQ ID NO: 3;

(c) amino acids 36 to 459, 594 to 921, 1177 to 1350, 1459 to 1523, 1545 to 1969, 2088 to 2424, 2445 to 2619, 2912 to 3261, 3266 to 3451, and 3551 to 3631 all in SEQ ID NO: 4;

(d) amino acids 34 to 456, 566 to 898, 1148 to 1333, and 1420 to 1503 all in SEQ ID NO: 5; and (e) amino acids 35 to 458, 582 to 917, 1233 to 1418, 1502 to 1585, 1715 to 1747 all in SEQ ID NO: 6.

24. An isolated polypeptide of claim 2 wherein the amino acid sequence is selected from the group consisting of:

(a) amino acids 15 to 1025, 1060 to 2616, and 2641 to 4457 all in SEQ ID NO: 2;

(b) amino acids 35 to 1895 in SEQ ID NO: 3;

(c) amino acids 36 to 1523, and 1545 to 3631 all in SEQ ID NO: 4;

(d) amino acids 34 to 1503 in SEQ ID NO: 5; and (e) amino acids 35 to 1747 in SEQ ID NO: 6.

25. A homogenous preparation of a polypeptide having an amino acid sequence selected from the group consisting of SEQ ID NO: 2, 3, 4, 5, and 6.

* * * * *